(12) United States Patent
Colletti et al.

(10) Patent No.: US 11,225,471 B2
(45) Date of Patent: Jan. 18, 2022

(54) ANTIDIABETIC BICYCLIC COMPOUNDS

(71) Applicants: Steven L. Colletti, Princeton, NJ (US);
Duane DeMong, Hanover, MA (US);
Kevin D. Dykstra, West Milford, NJ
(US); Zhiyong Hu, Livingston, NJ
(US); Michael Miller, Scotch Plains,
NJ (US); **Merck Sharp & Dohme
Corp.**, Rahway, NJ (US)

(72) Inventors: Steven L. Colletti, Princeton, NJ (US);
Duane DeMong, Hanover, MA (US);
Kevin D. Dykstra, West Milford, NJ
(US); Zhiyong Hu, Livingston, NJ
(US); Michael Miller, Scotch Plains,
NJ (US)

(73) Assignee: Merck Sharp & Dohme Corp.,
Rahway, NJ (US)

( * ) Notice: Subject to any disclaimer, the term of this patent is extended or adjusted under 35 U.S.C. 154(b) by 112 days.

(21) Appl. No.: 15/733,056

(22) PCT Filed: Nov. 12, 2018

(86) PCT No.: PCT/US2018/060244
§ 371 (c)(1),
(2) Date: May 1, 2020

(87) PCT Pub. No.: WO2019/099315
PCT Pub. Date: May 23, 2019

(65) Prior Publication Data
US 2021/0094938 A1    Apr. 1, 2021

Related U.S. Application Data

(60) Provisional application No. 62/587,119, filed on Nov. 16, 2017.

(51) Int. Cl.
*C07D 405/14*    (2006.01)
*A61P 3/10*    (2006.01)

(52) U.S. Cl.
CPC ............. *C07D 405/14* (2013.01); *A61P 3/10* (2018.01)

(58) Field of Classification Search
CPC .................................................. C07D 405/14
See application file for complete search history.

(56) References Cited

U.S. PATENT DOCUMENTS

| | | | |
|---|---|---|---|
| 9,840,512 B2* | 12/2017 | Brockunier | A61K 45/06 |
| 10,968,193 B2* | 4/2021 | Chen | C07D 487/04 |
| 2016/0002255 A1 | 1/2016 | Brockunier et al. | |
| 2016/0009662 A1* | 1/2016 | Meegalla | A61P 3/08 |
| | | | 514/210.2 |
| 2017/0210727 A1 | 7/2017 | Chen et al. | |
| 2017/0217918 A1 | 8/2017 | Chen | |

FOREIGN PATENT DOCUMENTS

| | | |
|---|---|---|
| EP | 1630152 A1 | 3/2006 |
| EP | 1698624 B1 | 6/2012 |
| GB | 2498976 A | 7/2013 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007033002 A1 | 3/2007 |
| WO | WO2007106469 A2 | 9/2007 |
| WO | WO2007123225 A1 | 11/2007 |

(Continued)

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.

Brown, S. P. et al., Discovery of AM-1638: A Potent and Orally Bioavailable GPR40/FFA1 Full Agonist, American Chemical Society, 2012, p. 726-730, vol. 3.

Houze, J. B. et al., 265-AMG 837: A potent, orally bioavailable, partial allosteric agonist of GPR40, MEDI, 2012, p. 1. Abstracts of Papers, 243rd ACS National Meeting & Exposition, San Diego, CA, Mar. 25-29, 2012.

Houze, J. B. et al., AMG 837: A potent, orally bioavailable GPR40 agonist, Bioorganic & Medicinal Chemistry Letters, 2012, p. 1267-1270, vol. 22.

(Continued)

*Primary Examiner* — Daniel R Carcanague
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia Formula (I).

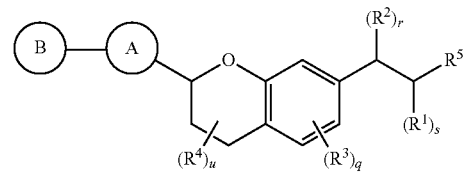

24 Claims, No Drawings

(56) References Cited

FOREIGN PATENT DOCUMENTS

| WO | WO2007136572 A2 | 11/2007 |
|---|---|---|
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009111056 A1 | 9/2009 |
| WO | WO2010004347 A1 | 1/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2015176267 A1 | 8/2010 |
| WO | WO2010143733 A1 | 12/2010 |
| WO | WO2012072691 A1 | 6/2012 |
| WO | WO2013122028 A1 | 8/2013 |
| WO | WO2013122029 A1 | 8/2013 |
| WO | 2014019186 A1 | 2/2014 |
| WO | WO2014022528 A1 | 2/2014 |
| WO | WO2014130608 A1 | 8/2014 |
| WO | 2015024448 A1 | 2/2015 |
| WO | WO2015051496 A1 | 4/2015 |
| WO | WO2015051725 A1 | 4/2015 |
| WO | WO2015073342 A1 | 5/2015 |
| WO | WO2015084692 A1 | 6/2015 |
| WO | WO2015089809 A1 | 6/2015 |
| WO | WO2015095256 A1 | 6/2015 |
| WO | WO2015119899 A1 | 8/2015 |
| WO | WO2015176640 A1 | 11/2015 |
| WO | 2016019863 A1 | 2/2016 |
| WO | 2016022446 A1 | 2/2016 |
| WO | 2016022448 A1 | 2/2016 |
| WO | WO2016019587 A1 | 2/2016 |
| WO | WO2016022742 A1 | 2/2016 |

OTHER PUBLICATIONS

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS One, 2011, p. 1-10, vol. 6, No. 11.

Lou, J. et al., A Potent Class of GPR40 Full Agonist Engages the EnteroInsular Axis to Promote Glucose Control in Rodents, PLOS One, 2012, p. 6-12, vol. 7, Issue 10.

PCT Search Report of International Application No. PCT/US2018/060244, dated Feb. 27, 2019, pp. 1-14.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25, 2010.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

* cited by examiner

ANTIDIABETIC BICYCLIC COMPOUNDS

CROSS-REFERENCE TO RELATED APPLICATIONS

This application is a U.S. National Phase application under 35 U.S.C. § 371 of PCT Application No. PCT/US2018/060244, filed on Nov. 12, 2018, which claims priority from and the benefit of U.S. Provisional Application No. 62/587,119, filed Nov. 16, 2017.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results induction and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); (5) inhibitors of incretin hormone degradation (DPP-4 inhibitors, such as sitagliptin, alogliptin, vildagliptin, linagliptin, denagliptin and saxagliptin); and SGLT2 inhibitors (canagliflozin, dapagliflozin and empagliflozin).

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/072691, WO 2013/122028, WO2013/122029, WO2014/019186, WO2014/130608, WO2014/022528, WO 2015/024448, WO2015/073342, WO2015/051725, WO2015/051496, WO2015/089809, WO2015/095256, WO2015/084692, WO2015/119899, WO2015/176640, WO2015/176267, WO2016/022446, WO2016/022742, WO2016/022448, WO2016/019863, WO2016/019587 and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; Houze et al., Abstracts of Papers, 243rd ACS National Meeting & Exposition, San Diego, Calif., USA Mar. 25-29, 2012, MEDI-265; and Plummer et al., ACS Med. Chem. Lett., 2017, 8(2), pp 221-226.

SUMMARY OF THE INVENTION

Compounds of structural formula I:

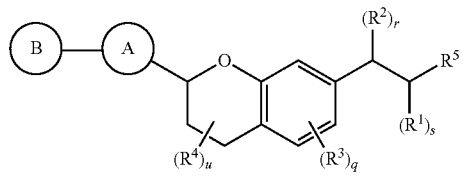

and pharmaceutically acceptable salts thereof, are disclosed. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

Disclosed are compounds of structural Formula I:

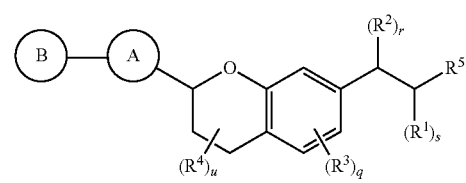

or a pharmaceutically acceptable salt thereof, wherein
A is pyrazine, wherein pyrazine is unsubstituted or substituted with one to two substituents selected from $R^a$, provided that one of $R^a$ and $R^4$ is not hydrogen;
B is selected from the group consisting of:
    (1) aryl, and
    (2) heteroaryl,
wherein B is unsubstituted or substituted with one to five substituents selected from $R^b$;
each $R^1$ is independently selected from the group consisting of:
    (1) —$C_{1-10}$alkyl,
    (2) —$C_{2-10}$ alkenyl,
    (3) —$C_{2-10}$alkynyl, and
    (4) —$C_{3-6}$cycloalkyl,
wherein each alkyl, alkenyl, alkynyl and cycloalkyl is unsubstituted or substituted with 1-4 substituents selected from $C_{1-6}$alkyl, halogen, and —$OC_{1-6}$alkyl;
each $R^2$ is independently selected from the group consisting of:
    (1) —$C_{1-10}$alkyl,
    (2) —$C_{2-10}$ alkenyl,
    (3) —$C_{2-10}$alkynyl,
    (4) —$C_{3-6}$cycloalkyl,
    (5) —$C_{2-6}$cycloheteroalkyl, (6) aryl, and
(7) heteroaryl,
wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;

$R^3$ is selected from the group consisting of:
(1) hydrogen,
(2) halogen, and
(3) —$C_{1-6}$alkyl;

$R^4$ is selected from the group consisting of:
(1) hydrogen,
(2) $C_{1-6}$alkyl, and
(3) $C_{1-6}$alkyl-O—;

$R^5$ is selected from the group consisting of:
(1) —$CO_2R^6$, and
(2) —$C(O)NR^cR^d$;

$R^6$ is selected from the group consisting of:
(1) hydrogen,
(2) —$C_{1-6}$alkyl,
(3) —$C_{3-6}$cycloalkyl, and
(4) aryl-$C_{1-6}$alkyl,
wherein each alkyl, cycloalkyl and aryl is unsubstituted or substituted with one to three substituents selected from $R^h$;

$R^a$ is selected from the group consisting of:
(1) hydrogen,
(2) —$C_{1-3}$alkyl,
(3) —$CF_3$, and
(4) —$C_{3-6}$cycloalkyl,
wherein each alkyl and cycloalkyl is unsubstituted or substituted with one to three substituents selected from: —$C_{1-3}$ alkyl, halogen and —$CF_3$;

$R^b$ is independently selected from the group consisting of:
(1) —$C_{1-10}$alkyl,
(2) —$CF_3$,
(3) halogen,
(4) —CN,
(5) —OH,
(6) —$OC_{1-10}$alkyl,
(7) —$O(CH_2)pOC_{1-10}$alkyl,
(8) —$O(CH_2)pC_{3-6}$cycloalkyl,
(9) —$O(CH_2)pC_{2-5}$cycloheteroalkyl,
(10) —$O(CH_2)pNR^cR^d$,
(11) —$O(CH_2)pO$—$C_{3-6}$cycloalkyl,
(12) —$OCF_3$,
(13) —$OCHF_2$,
(14) —$(CH_2)pC_{3-6}$cycloalkyl, and
(15) —$(CH_2)pC_{2-5}$cycloheteroalkyl,
wherein each CH, $CH_2$, alkyl, alkenyl, cycloalkyl, cycloheteroalkyl, aryl and heteroaryl is unsubstituted or substituted with one to five substituents selected from: —$C_{1-6}$ alkyl, halogen, —O—$C_{1-6}$alkyl and —$CF_3$;

$R^c$ and $R^d$ are each independently selected from the group consisting of:
(1) hydrogen,
(2) $C_{1-10}$alkyl,
(3) $C_{3-6}$cycloalkyl,
(4) $C_{3-6}$ cycloalkyl-$C_{1-10}$alkyl-,
(5) $C_{2-5}$cycloheteroalkyl,
(6) aryl-$C_{1-10}$alkyl-, and
(7) heteroaryl-$C_{1-10}$alkyl-,
wherein each alkyl, cycloalkyl, cycloheteroalkyl, aryl and heteroaryl is unsubstituted or substituted with one to three substituents independently selected from $R^f$,
or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$;

each $R^e$ is independently selected from the group consisting of:
(1) hydrogen,
(2) —$C_{1-10}$alkyl,
(3) —$C_{3-6}$ cycloalkyl, and
(4) —$C_{2-5}$cycloheteroalkyl;

each $R^f$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, and $C_{1-6}$alkyl;

each $R^g$ is selected from the group consisting of:
(1) hydrogen, and
(2) —$C_{1-10}$alkyl,
wherein each alkyl is unsubstituted or substituted with one to five halogens;

$R^h$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

each m is independently selected from: 0, 1 and 2;
each p is independently selected from: 0, 1, 2, 3, 4, 5 and 6;
each q is independently selected from 0, 1, 2 and 3;
each u is independently selected from 0, 1 and 2;
each r is independently selected from 0 and 1; and
each s is independently selected from 0 and 1.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is pyrazine, wherein pyrazine is unsubstituted or substituted with one to two substituents selected from $R^a$, provided that one of $R^a$ and $R^4$ is not hydrogen.

In another embodiment of the present invention, A is pyrazine, wherein pyrazine is unsubstituted or substituted with one to two substituents selected from $R^a$.

In another embodiment of the present invention, A is pyrazine, wherein pyrazine is substituted with one to two substituents selected from $R^a$, provided that one of $R^a$ and $R^4$ is not hydrogen.

In another embodiment of the present invention, A is pyrazine, wherein pyrazine is substituted with one to two substituents selected from $R^a$.

In another embodiment of the present invention, A is pyrazine, wherein pyrazine is substituted with one substituent selected from $R^a$.

In another embodiment of the present invention, B is heteroaryl, wherein heteroaryl is unsubstituted or substituted with one to five substituents selected from $R^b$.

In another embodiment of the present invention, B is heteroaryl, wherein heteroaryl is substituted with one to five substituents selected from $R^b$.

In another embodiment of the present invention, B is pyridine, wherein pyridine is unsubstituted or substituted with one to five substituents selected from $R^b$.

In another embodiment of the present invention, B is pyridine, wherein pyridine is substituted with one to five substituents selected from $R^b$.

In another embodiment of the present invention, B is pyridine, wherein pyridine is substituted with two substituents selected from $R^b$.

In another embodiment of the present invention, each $R^1$ is independently selected from the group consisting of —$C_{1-10}$alkyl, —$C_{2-10}$ alkenyl, —$C_{2-10}$alkynyl and —$C_{3-6}$cycloalkyl, wherein each alkyl, alkenyl, alkynyl and cycloalkyl is unsubstituted or substituted with 1-4 substituents selected from $C_{1-6}$alkyl, halogen, and —$OC_{1-6}$alkyl.

In another embodiment of the present invention, each $R^1$ is independently selected from the group consisting of —$C_{1-10}$alkyl, —$C_{2-10}$ alkenyl and —$C_{2-10}$alkynyl, wherein each alkyl, alkenyl and alkynyl is unsubstituted or substituted with 1-4 substituents selected from $C_{1-6}$alkyl, halogen, and —$OC_{1-6}$alkyl.

In another embodiment of the present invention, each $R^1$ is independently selected from the group consisting of —$C_{1-10}$alkyl and —$C_{2-10}$ alkenyl, wherein each alkyl and alkenyl is unsubstituted or substituted with 1-4 substituents selected from $C_{1-6}$alkyl, halogen, and —$OC_{1-6}$alkyl.

In another embodiment of the present invention, each $R^1$ is —$C_{1-10}$alkyl, wherein each alkyl is unsubstituted or substituted with 1-4 substituents selected from $C_{1-6}$alkyl, halogen, and —$OC_{1-6}$alkyl. In a class of this embodiment, each —$C_{1-10}$alkyl is unsubstituted or substituted with 1-4 substituents selected from $C_{1-3}$alkyl, and halogen. In another class of this embodiment, each $R^1$ is —$C_{1-10}$alkyl.

In another embodiment of the present invention, each $R^1$ is —$C_{1-6}$alkyl, wherein each alkyl is unsubstituted or substituted with 1-4 substituents selected from $C_{1-6}$alkyl, halogen, and —$OC_{1-6}$alkyl. In a class of this embodiment, each —$C_{1-6}$alkyl is unsubstituted or substituted with 1-4 substituents selected from $C_{1-3}$alkyl, and halogen. In another class of this embodiment, each $R^1$ is —$C_{1-6}$alkyl.

In another embodiment of the present invention, each $R^1$ is —$C_{1-3}$alkyl, wherein each alkyl is unsubstituted or substituted with 1-4 substituents selected from $C_{1-3}$alkyl, halogen, and —$OC_{1-6}$alkyl. In a class of this embodiment, each —$C_{1-3}$alkyl is unsubstituted or substituted with 1-4 substituents selected from $C_{1-3}$alkyl, and halogen. In another class of this embodiment, each $R^1$ is —$C_{1-3}$alkyl.

In another embodiment of the present invention, each $R^1$ is —$CH_3$, wherein each —$CH_3$ is unsubstituted or substituted with 1-4 substituents selected from $C_{1-6}$alkyl, halogen, and —$OC_{1-6}$alkyl. In a class of this embodiment, each —$CH_3$ is unsubstituted or substituted with 1-4 substituents selected from $C_{1-3}$alkyl, and halogen. In another class of this embodiment, each $R^1$ is —$CH_3$.

In another embodiment of the present invention, $R^2$ is independently selected from the group consisting of —$C_{1-10}$alkyl, —$C_{2-10}$ alkenyl, —$C_{2-10}$alkynyl, —$C_{3-6}$cycloalkyl, —$C_{2-6}$cycloheteroalkyl, aryl, and heteroaryl, wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl.

In another embodiment of the present invention, $R^2$ is independently selected from the group consisting of —$C_{1-10}$ alkyl, —$C_{2-10}$ alkenyl, —$C_{2-10}$alkynyl, —$C_{3-6}$cycloalkyl and —$C_{2-6}$cycloheteroalkyl, wherein each alkyl, alkenyl, alkynyl, cycloalkyl and cycloheteroalkyl is unsubstituted or substituted with 1-4 substituents selected from $C_{1-6}$alkyl, halogen, and —$OC_{1-6}$alkyl.

In another embodiment of the present invention, $R^2$ is independently selected from the group consisting of —$C_{1-10}$ alkyl, —$C_{3-6}$cycloalkyl, and —$C_{2-6}$cycloheteroalkyl, wherein each alkyl, cycloalkyl and cycloheteroalkyl is unsubstituted or substituted with 1-4 substituents selected from $C_{1-6}$alkyl, halogen, and —$OC_{1-6}$alkyl.

In another embodiment of the present invention, $R^2$ is independently selected from the group consisting of —$C_{1-10}$ alkyl, and —$C_{3-6}$cycloalkyl, wherein each alkyl and cycloalkyl is unsubstituted or substituted with 1-4 substituents selected from $C_{1-6}$alkyl, halogen, and —$OC_{1-6}$alkyl.

In another embodiment of the present invention, $R^2$ is —$C_{1-10}$alkyl, unsubstituted or substituted with 1-4 substituents selected from $C_{1-6}$alkyl, halogen, and —$OC_{1-6}$alkyl.

In another embodiment of the present invention, $R^2$ is —$C_{3-6}$cycloalkyl, unsubstituted or substituted with 1-4 substituents selected from $C_{1-6}$alkyl, halogen, and —$OC_{1-6}$alkyl. In a class of this embodiment, $R^2$ is —$C_{3-6}$cycloalkyl, unsubstituted or substituted with 1-4 substituents selected from $C_{1-6}$alkyl and halogen. In another class of this embodiment, $R^2$ is —$C_{3-6}$cycloalkyl.

In another embodiment of the present invention, $R^2$ is —$C_{3-5}$cycloalkyl, unsubstituted or substituted with 1-4 substituents selected from $C_{1-6}$alkyl, halogen, and —$OC_{1-6}$alkyl. In a class of this embodiment, $R^2$ is —$C_{3-5}$cycloalkyl, unsubstituted or substituted with 1-4 substituents selected from $C_{1-6}$alkyl and halogen. In another class of this embodiment, $R^2$ is —$C_{3-5}$cycloalkyl.

In another embodiment of the present invention, $R^2$ is —$C_{3-4}$cycloalkyl, wherein each cycloalkyl is unsubstituted or substituted with 1-4 substituents selected from $C_{1-6}$alkyl, halogen, and —$OC_{1-6}$alkyl. In a class of this embodiment, $R^2$ is —$C_{3-4}$cycloalkyl, unsubstituted or substituted with 1-4 substituents selected from $C_{1-6}$alkyl and halogen. In another class of this embodiment, $R^2$ is: —$C_{3-4}$cycloalkyl.

In another embodiment of the present invention, $R^2$ is cyclopropyl, unsubstituted or substituted with 1-4 substituents selected from $C_{1-6}$alkyl, halogen, and —$OC_{1-6}$alkyl. In a class of this embodiment, $R^2$ is cyclopropyl, unsubstituted or substituted with 1-4 substituents selected from $C_{1-6}$alkyl and halogen. In another class of this embodiment, $R^2$ is cyclopropyl.

In another embodiment of the present invention, $R^3$ is selected from the group consisting of hydrogen, halogen and —$C_{1-6}$alkyl.

In another embodiment of the present invention, $R^3$ is selected from the group consisting of —$C_{1-6}$alkyl.

In another embodiment of the present invention, $R^3$ is selected from the group consisting of hydrogen and halogen. In another class of this embodiment, $R^3$ is hydrogen.

In another embodiment of the present invention, $R^3$ is halogen. In a class of this embodiment, $R^3$ is selected from the group consisting of: F and Cl. In another class of this embodiment, $R^3$ is Cl. In another class of this embodiment, $R^3$ is F.

In another embodiment of the present invention, $R^4$ is selected from the group consisting of hydrogen, —$C_{1-6}$alkyl, and $C_{1-6}$alkyl-O—.

In another embodiment of the present invention, $R^4$ is selected from the group consisting of hydrogen and $C_{1-6}$alkyl-O—.

In another embodiment of the present invention, $R^4$ is hydrogen.

In another embodiment of the present invention, $R^4$ is hydrogen or $C_{1-6}$alkyl-O—. In a class of this embodiment, $R^4$ is hydrogen or $C_{1-3}$alkyl-O—. In another class of this embodiment, $R^4$ is hydrogen or $CH_3O$—. In another class of this embodiment, $R^4$ is hydrogen. In another class of this embodiment, $R^4$ is $CH_3O$—.

In another embodiment of the present invention, $R^4$ is $C_{1-6}$alkyl-O—. In a class of this embodiment, $R^4$ is $C_{1-3}$alkyl-O—. In another class of this embodiment, $R^4$ is $CH_3O$—.

In another embodiment of the present invention, $R^5$ is selected from the group consisting of —$CO_2R^6$ and —$C(O)NR^cR^d$.

In another embodiment of the present invention, $R^5$ is —$C(O)NR^cR^d$. In a class of this embodiment, $R^5$ is —$C(O)NH_2$.

In another embodiment of the present invention, $R^5$ is —$CO_2R^6$. In a class of this embodiment, $R^5$ is —$CO_2H$.

In another embodiment of the present invention, $R^6$ is selected from the group consisting of hydrogen, —$C_{1-6}$alkyl, —$C_{3-6}$cycloalkyl, and aryl-$C_{1-6}$alkyl, wherein each alkyl, cycloalkyl and aryl is unsubstituted or substituted with one to three substituents selected from $R^h$.

In another embodiment of the present invention, $R^6$ is selected from the group consisting of hydrogen, and —$C_{1-6}$alkyl, wherein each alkyl is unsubstituted or substituted with one to three substituents selected from $R^h$.

In another embodiment of the present invention, $R^6$ is —$C_{1-6}$alkyl, wherein each alkyl is unsubstituted or substituted with one to three substituents selected from $R^h$.

In another embodiment of the present invention, $R^6$ is selected from the group consisting of hydrogen, —$C_{1-6}$alkyl and —$C_{3-6}$cycloalkyl, wherein each alkyl and cycloalkyl is unsubstituted or substituted with one to three substituents selected from $R^h$. In a class of this embodiment, $R^6$ is selected from the group consisting of: hydrogen and —$C_{1-6}$alkyl, wherein each alkyl is unsubstituted or substituted with one to three substituents selected from $R^h$. In another class of this embodiment, $R^6$ is —$C_{1-6}$alkyl, wherein each alkyl is unsubstituted or substituted with one to three substituents selected from $R^h$. In another class of this embodiment, $R^6$ is hydrogen.

In another embodiment of the present invention, $R^a$ is selected from the group consisting of hydrogen, —$C_{1-3}$alkyl, —$CF_3$, and —$C_{3-6}$cycloalkyl, wherein each alkyl and cycloalkyl is unsubstituted or substituted with one to three substituents selected from: —$C_{1-3}$alkyl, halogen and —$CF_3$.

In another embodiment of the present invention, $R^a$ is selected from the group consisting of hydrogen, —$C_{1-3}$alkyl, and —$CF_3$, wherein each alkyl and cycloalkyl is unsubstituted or substituted with one to three substituents selected from: —$C_{1-3}$alkyl, halogen and —$CF_3$.

In another embodiment of the present invention, $R^a$ is selected from the group consisting of hydrogen, and —$C_{1-3}$alkyl, wherein each alkyl is unsubstituted or substituted with one to three substituents selected from: —$C_{1-3}$alkyl, halogen and —$CF_3$.

In another embodiment of the present invention, $R^a$ is selected from the group consisting of hydrogen, and —$C_{1-3}$alkyl. In a class of this embodiment, $R^a$ is selected from the group consisting of: hydrogen, —$CH_3$ and —$CH_2CH_3$, wherein each alkyl is unsubstituted or substituted with —$C_{1-6}$alkyl, halogen, —O—$C_{1-6}$alkyl and —$CF_3$. In another class of this embodiment, $R^a$ is selected from the group consisting of: hydrogen, —$CH_3$ and —$CH_2CH_3$.

In another embodiment of the present invention, $R^a$ is hydrogen.

In another embodiment of the present invention, $R^a$ is selected from the group consisting of —$C_{1-3}$alkyl, wherein each alkyl is unsubstituted or substituted with —$C_{1-6}$alkyl, halogen, —O—$C_{1-6}$alkyl and —$CF_3$. In a class of this embodiment, $R^a$ is selected from the group consisting of: —$C_{1-3}$alkyl.

In another embodiment of the present invention, $R^a$ is selected from the group consisting of —$C_{1-2}$alkyl, wherein each alkyl is unsubstituted or substituted with —$C_{1-6}$alkyl, halogen, —O—$C_{1-6}$alkyl and —$CF_3$. In a class of this embodiment, $R^a$ is selected from the group consisting of: —$C_{1-2}$alkyl.

In another embodiment of the present invention, $R^a$ is selected from the group consisting of —$CH_3$ and —$CH_2CH_3$, wherein each alkyl is unsubstituted or substituted with —$C_{1-6}$alkyl, halogen, —O—$C_{1-6}$alkyl and —$CF_3$. In a class of this embodiment, $R^a$ is selected from the group consisting of: —$CH_3$ and —$CH_2CH_3$. In another class of this embodiment, $R^a$ is —$CH_2CH_3$. In another class of this embodiment, $R^a$ is —$CH_3$.

In another embodiment of the present invention, $R^b$ is independently selected from the group consisting of —$C_{1-10}$alkyl, —$CF_3$, halogen, —CN, —OH, —$OC_{1-10}$alkyl, —O($CH_2$)p$OC_{1-10}$alkyl, —O($CH_2$)p$C_{3-6}$cycloalkyl, —O($CH_2$)p$C_{2-5}$cycloheteroalkyl, —O($CH_2$)p$NR^cR^d$, —O($CH_2$)pO—$C_{3-6}$cycloalkyl, —$OCF_3$, —$OCHF_2$, —($CH_2$)p$C_{3-6}$cycloalkyl, and —($CH_2$)p$C_{2-5}$cycloheteroalkyl, wherein each CH, $CH_2$, alkyl, alkenyl, cycloalkyl, cycloheteroalkyl, aryl and heteroaryl is unsubstituted or substituted with one to five substituents selected from: —$C_{1-6}$alkyl, halogen, —O—$C_{1-6}$alkyl and —$CF_3$.

In another embodiment of the present invention, $R^b$ is independently selected from the group consisting of —$C_{1-10}$alkyl, —$CF_3$, halogen, —CN, —OH, —$OC_{1-10}$alkyl, —$OCF_3$, —$OCHF_2$, —($CH_2$)p$C_{3-6}$cycloalkyl, and —($CH_2$)p$C_{2-5}$cycloheteroalkyl, wherein each CH, $CH_2$, alkyl, cycloalkyl and cycloheteroalkyl is unsubstituted or substituted with one to five substituents selected from: —$C_{1-6}$alkyl, halogen, —O—$C_{1-6}$alkyl and —$CF_3$.

In another embodiment of the present invention, $R^b$ is independently selected from the group consisting of —$C_{1-10}$alkyl, halogen, —$OC_{1-10}$alkyl, —($CH_2$)p$C_{3-6}$cycloalkyl and —($CH_2$)p$C_{2-5}$cycloheteroalkyl, wherein each $CH_2$, alkyl, cycloalkyl and cycloheteroalkyl is unsubstituted or substituted with one to five substituents selected from: —$C_{1-6}$alkyl, halogen, —O—$C_{1-6}$alkyl and —$CF_3$.

In another embodiment of the present invention, $R^b$ is independently selected from the group consisting of: —$C_{1-10}$alkyl, halogen, —$OC_{1-10}$alkyl and —($CH_2$)p$C_{3-6}$cycloalkyl, wherein each $CH_2$, alkyl and cycloalkyl is unsubstituted or substituted with one to five substituents selected from: —$C_{1-6}$alkyl, halogen, —O—$C_{1-6}$alkyl and —$CF_3$. In a class of this embodiment, each $CH_2$, alkyl and cycloalkyl is unsubstituted or substituted with one to five substituents selected from: halogen. In another class of this embodiment, each $CH_2$, alkyl and cycloalkyl is unsubstituted or substituted with one to five substituents selected from: F.

In another embodiment of the present invention, $R^b$ is —$C_{1-10}$alkyl, wherein each alkyl is unsubstituted or substituted with one to five substituents selected from: —$C_{1-6}$ alkyl, halogen, —O—$C_{1-6}$alkyl and —$CF_3$. In a class of this embodiment, $R^b$ is —$C_{1-10}$alkyl.

In another embodiment of the present invention, $R^b$ is independently selected from the group consisting of: halogen, —$OC_{1-10}$alkyl, and —$(CH_2)pC_{3-6}$cycloalkyl, wherein each $CH_2$, alkyl, and cycloalkyl is unsubstituted or substituted with one to five substituents selected from: —$C_{1-6}$ alkyl, halogen, —O—$C_{1-6}$alkyl and —$CF_3$.

In a class of this embodiment, $R^b$ is independently selected from the group consisting of: halogen, —$OC_{1-10}$ alkyl, and —$(CH_2)pC_{3-6}$cycloalkyl, wherein each $CH_2$, alkyl, and cycloalkyl is unsubstituted or substituted with one to five substituents selected from: halogen.

In another class of this embodiment, $R^b$ is independently selected from the group consisting of: halogen, —$OC_{1-10}$ alkyl, and —$(CH_2)pC_{3-6}$cycloalkyl, wherein each $CH_2$, alkyl, and cycloalkyl is unsubstituted or substituted with one to five substituents selected from: F.

In another class of this embodiment, $R^b$ is independently selected from the group consisting of: halogen, —$OC_{1-10}$ alkyl, and —$C_{3-6}$cycloalkyl, wherein each alkyl, and cycloalkyl is unsubstituted or substituted with one to five substituents selected from: —$C_{1-6}$alkyl, halogen, —O—$C_{1-6}$ alkyl and —$CF_3$.

In another class of this embodiment, $R^b$ is independently selected from the group consisting of: halogen, —$OC_{1-10}$ alkyl, and —$C_{3-6}$cycloalkyl, wherein each alkyl, and cycloalkyl is unsubstituted or substituted with one to five substituents selected from: halogen.

In another class of this embodiment, $R^b$ is independently selected from the group consisting of: halogen, —$OC_{1-10}$ alkyl, and —$C_{3-6}$cycloalkyl, wherein each alkyl, and cycloalkyl is unsubstituted or substituted with one to five substituents selected from: F.

In another class of this embodiment, $R^b$ is independently selected from the group consisting of: Cl, F, —$OCH_3$, —$OCH_2CH_3$, and cyclopropyl, wherein $R^b$ is unsubstituted or substituted with one to five substituents selected from: —$C_{1-6}$alkyl, halogen, —O—$C_{1-6}$alkyl and —$CF_3$.

In another class of this embodiment, $R^b$ is independently selected from the group consisting of: Cl, F, —$OCH_3$, —$OCH_2CH_3$, and cyclopropyl, wherein $R^b$ is unsubstituted or substituted with one to five substituents selected from: halogen.

In another class of this embodiment, $R^b$ is independently selected from the group consisting of: Cl, F, —$OCH_3$, —$OCH_2CH_3$, and cyclopropyl, wherein $R^b$ is unsubstituted or substituted with one to five substituents selected from: F.

In another embodiment of the present invention, $R^b$ is independently selected from the group consisting of: halogen and —$OC_{1-10}$alkyl, wherein alkyl is unsubstituted or substituted with one to five substituents selected from: —$C_{1-6}$alkyl, halogen, —O—$C_{1-6}$alkyl and —$CF_3$. In a class of this embodiment, $R^b$ is independently selected from the group consisting of halogen and —$OC_{1-10}$alkyl, wherein alkyl is unsubstituted or substituted with one to five substituents selected from: halogen. In another class of this embodiment, $R^b$ is independently selected from the group consisting of halogen, and —$OC_{1-10}$alkyl, wherein alkyl is unsubstituted or substituted with one to five substituents selected from: F.

In another class of this embodiment, $R^b$ is independently selected from the group consisting of: Cl, F, —$OCH_3$, and —$OCH_2CH_3$.

In another class of this embodiment, $R^b$ is independently selected from the group consisting of: Cl, and —$OCH_3$.

In another embodiment of the present invention, $R^c$ and $R^d$ are each independently selected from the group consisting of: hydrogen, $C_{1-10}$alkyl, $C_{3-6}$cycloalkyl, $C_{3-6}$ cycloalkyl-$C_{1-10}$alkyl-, $C_{2-5}$cycloheteroalkyl, aryl-$C_{1-10}$alkyl-, and heteroaryl-$C_{1-10}$alkyl-,
wherein each alkyl, cycloalkyl, cycloheteroalkyl, aryl and heteroaryl is unsubstituted or substituted with one to three substituents independently selected from $R^f$,
or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$.

In another embodiment of the present invention, $R^c$ and $R^d$ are each independently selected from the group consisting of: hydrogen, $C_{1-10}$alkyl, $C_{3-6}$cycloalkyl, $C_{3-6}$ cycloalkyl-$C_{1-10}$alkyl-, $C_{2-5}$cycloheteroalkyl, aryl-$C_{1-10}$alkyl-, and heteroaryl-$C_{1-10}$alkyl-, wherein each alkyl, cycloalkyl, cycloheteroalkyl, aryl and heteroaryl is unsubstituted or substituted with one to three substituents independently selected from $R^f$.

In another embodiment of the present invention, $R^c$ and $R^d$ are each independently selected from the group consisting of: hydrogen, $C_{1-10}$alkyl, $C_{3-6}$cycloalkyl, and $C_{2-5}$cycloheteroalkyl, wherein each alkyl, cycloalkyl and cycloheteroalkyl is unsubstituted or substituted with one to three substituents independently selected from $R^f$.

In another embodiment of the present invention, $R^c$ and $R^d$ are each independently selected from the group consisting of: hydrogen, and $C_{1-10}$alkyl, wherein each alkyl is unsubstituted or substituted with one to three substituents independently selected from $R^f$.

In another embodiment of the present invention, $R^c$ and $R^d$ are $C_{1-10}$alkyl, wherein each alkyl is unsubstituted or substituted with one to three substituents independently selected from $R^f$.

In another embodiment of the present invention, $R^c$ and $R^d$ are hydrogen.

In another embodiment of the present invention, $R^c$ is selected from the group consisting of: hydrogen, $C_{1-10}$alkyl, $C_{3-6}$cycloalkyl, $C_{3-6}$ cycloalkyl-$C_{1-10}$alkyl-, $C_{2-5}$cycloheteroalkyl, aryl-$C_{1-10}$alkyl-, and heteroaryl-$C_{1-10}$alkyl-, wherein each alkyl, cycloalkyl, cycloheteroalkyl, aryl and heteroaryl is unsubstituted or substituted with one to three substituents independently selected from $R^f$.

In another embodiment of the present invention, $R^c$ is selected from the group consisting of: hydrogen, $C_{1-10}$alkyl, $C_{3-6}$cycloalkyl, and $C_{2-5}$cycloheteroalkyl, wherein each alkyl, cycloalkyl and cycloheteroalkyl is unsubstituted or substituted with one to three substituents independently selected from $R^f$.

In another embodiment of the present invention, $R^c$ is selected from the group consisting of: hydrogen, and $C_{1-10}$alkyl, wherein each alkyl is unsubstituted or substituted with one to three substituents independently selected from $R^f$.

In another embodiment of the present invention, $R^c$ is $C_{1-10}$alkyl, wherein each alkyl is unsubstituted or substituted with one to three substituents independently selected from $R^f$.

In another embodiment of the present invention, $R^c$ is hydrogen.

In another embodiment of the present invention, $R^d$ is selected from the group consisting of: hydrogen, $C_{1-10}$alkyl, $C_{3-6}$cycloalkyl, $C_{3-6}$ cycloalkyl-$C_{1-10}$alkyl-, $C_{2-5}$cycloheteroalkyl, aryl-$C_{1-10}$alkyl-, and heteroaryl-$C_{1-10}$alkyl-, wherein each alkyl, cycloalkyl, cycloheteroalkyl, aryl and heteroaryl is unsubstituted or substituted with one to three substituents independently selected from $R^f$.

In another embodiment of the present invention, $R^d$ is selected from the group consisting of: hydrogen, $C_{1-10}$alkyl, $C_{3-6}$cycloalkyl, and $C_{2-5}$cycloheteroalkyl, wherein each alkyl, cycloalkyl and cycloheteroalkyl is unsubstituted or substituted with one to three substituents independently selected from $R^f$.

In another embodiment of the present invention, $R^d$ is selected from the group consisting of: hydrogen, and $C_{1-10}$alkyl, wherein each alkyl is unsubstituted or substituted with one to three substituents independently selected from $R^f$.

In another embodiment of the present invention, $R^d$ is $C_{1-10}$alkyl, wherein each alkyl is unsubstituted or substituted with one to three substituents independently selected from $R^f$.

In another embodiment of the present invention, $R^d$ is hydrogen.

In another embodiment of the present invention, each $R^e$ is independently selected from the group consisting of: hydrogen, —$C_{1-10}$alkyl, —$C_{3-6}$ cycloalkyl and —$C_{2-5}$cycloheteroalkyl.

In another embodiment of the present invention, each $R^e$ is independently selected from the group consisting of: hydrogen and —$C_{1-10}$alkyl.

In another embodiment of the present invention, each $R^e$ is —$C_{1-10}$alkyl.

In another embodiment of the present invention, each $R^e$ is hydrogen.

In another embodiment of the present invention, each $R^f$ is selected from the group consisting of: halogen, $C_{1-10}$alkyl, —OH, —O—$C_{1-4}$alkyl, —S(O)$_m$—$C_{1-4}$alkyl, —CN, —CF$_3$, —OCHF$_2$, and —OCF$_3$, wherein each alkyl is unsubstituted or substituted with one to three substituents independently selected from: —OH, halogen, and $C_{1-6}$alkyl.

In another embodiment of the present invention, each $R^f$ is selected from the group consisting of: halogen, $C_{1-10}$alkyl, —OH, —O—$C_{1-4}$alkyl, —CN, —CF$_3$, —OCHF$_2$, and —OCF$_3$, wherein each alkyl is unsubstituted or substituted with one to three substituents independently selected from: —OH, halogen, and $C_{1-6}$alkyl.

In another embodiment of the present invention, each $R^f$ is selected from the group consisting of: halogen, $C_{1-10}$alkyl, —OH, —O—$C_{1-4}$alkyl, —CN, and —CF$_3$, wherein each alkyl is unsubstituted or substituted with one to three substituents independently selected from: —OH, halogen, and $C_{1-6}$alkyl.

In another embodiment of the present invention, each $R^f$ is selected from the group consisting of: halogen, $C_{1-10}$alkyl, —OH, and —O—$C_{1-4}$alkyl, wherein each alkyl is unsubstituted or substituted with one to three substituents independently selected from: —OH, halogen, and $C_{1-6}$alkyl.

In another embodiment of the present invention, each $R^f$ is selected from the group consisting of: halogen, and $C_{1-10}$alkyl, wherein each alkyl is unsubstituted or substituted with one to three substituents independently selected from: —OH, halogen, and $C_{1-6}$alkyl.

In another embodiment of the present invention, each $R^f$ is $C_{1-10}$alkyl, wherein each alkyl is unsubstituted or substituted with one to three substituents independently selected from: —OH, halogen, and $C_{1-6}$alkyl.

In another embodiment of the present invention, each $R^f$ is halogen.

In another embodiment of the present invention, each $R^g$ is selected from the group consisting of: hydrogen and —$C_{1-10}$alkyl, wherein each alkyl is unsubstituted or substituted with one to five halogens.

In another embodiment of the present invention, each $R^g$ is —$C_{1-10}$alkyl, unsubstituted or substituted with one to five halogens.

In another embodiment of the present invention, each $R^g$ is hydrogen.

In another embodiment of the present invention, $R^h$ is independently selected from the group consisting of: —$C_{1-6}$ alkyl, —OR$^e$, —NR$^c$S(O)$_m$R$^e$, halogen, —S(O)$_m$R$^e$, —S(O)$_m$ NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$, —OCHF$_2$, —$C_{3-6}$cycloalkyl and —$C_{2-5}$cycloheteroalkyl.

In another embodiment of the present invention, $R^h$ is independently selected from the group consisting of —$C_{1-6}$ alkyl, —OR$^e$, —NR$^c$S(O)$_m$R$^e$, halogen, —S(O)$_m$R$^e$, —S(O)$_m$ NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$, and —OCHF$_2$.

In another embodiment of the present invention, $R^h$ is independently selected from the group consisting of —$C_{1-6}$ alkyl, —OR$^e$, halogen, —S(O)$_m$R$^e$, —NR$^c$R$^d$, —C(O)R$^e$, —OC(O)R$^e$, —CO$_2$R$^e$, —CN, —CF$_3$, —OCF$_3$, and —OCHF$_2$.

In another embodiment of the present invention, $R^h$ is independently selected from the group consisting of —$C_{1-6}$ alkyl, —OR$^e$, halogen, —CN, —CF$_3$, —OCF$_3$ and —OCHF$_2$.

In another embodiment of the present invention, $R^h$ is independently selected from the group consisting of —$C_{1-6}$ alkyl, halogen, —CN and —CF$_3$.

In another embodiment of the present invention, $R^h$ is independently selected from the group consisting of —$C_{1-6}$ alkyl and halogen.

In another embodiment of the present invention, $R^h$ is —$C_{1-6}$alkyl.

In another embodiment of the present invention, $R^h$ is halogen.

In another embodiment of the present invention, n is 0, 1 or 2.

In another embodiment of the present invention, m is 0, 1 or 2. In a class of this embodiment, m is 1 or 2. In another class of this embodiment, m is 0 or 1. In another class of this embodiment, m is 0 or 2. In another class of this embodiment, m is 0. In another class of this embodiment, m is 1. In another class of this embodiment, m is 2.

In another embodiment of the present invention, each p is independently selected from: 0, 1, 2, 3, 4, 5 or 6. In a class of this embodiment, each p is independently selected from: 1, 2, 3, 4, or 6. In another class of this embodiment, p is 1, 2, 3, 4 or 5. In another class of this embodiment, p is 1, 2, 3 or 4. In another class of this embodiment, p is 1, 2 or 3. In another class of this embodiment, p is 1 or 2. In another class of this embodiment, p is 1 or 3. In another class of this embodiment, p is 2 or 3. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6.

In another embodiment of the present invention, each q is 0, 1, 2 or 3. In a class of this embodiment, q is 0, 1 or 2. In a class of this embodiment, q is 1, 2 or 3. In a class of this embodiment, q is 1 or 2. In another class of this embodiment, q is 2 or 3. In another class of this embodiment, q is 0 or 1. In another class of this embodiment, q is 0 or 2. In another class of this embodiment, q is 0. In another class of this embodiment, q is 1. In another class of this embodiment, q is 2. In another class of this embodiment, q is 3.

In another embodiment of the present invention, u is 0, 1 or 2. In a class of this embodiment, u is 1 or 2. In another class of this embodiment, u is 0 or 1. In another class of this embodiment, u is 0 or 2. In another class of this embodiment, u is 0. In another class of this embodiment, u is 1. In another class of this embodiment, u is 2.

In another embodiment of the present invention, r is 0 or 1. In a class of this embodiment, r is 0. In another class of this embodiment, r is 1.

In another embodiment of the present invention, s is 0 or 1. In a class of this embodiment, s is 0. In another class of this embodiment, s is 1.

In another embodiment of the present invention, the invention relates to compounds of structural formula Ia:

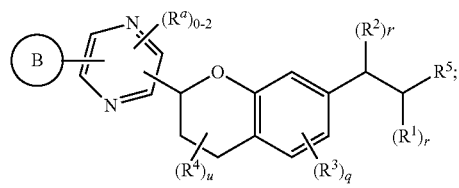

Ia or a pharmaceutically acceptable salt thereof.

In another embodiment of the present invention, the invention relates to compounds of structural formula Ib:

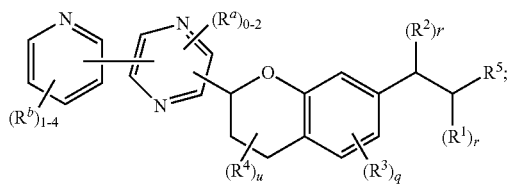

Ib or a pharmaceutically acceptable salt thereof.

In another embodiment of the present invention, the invention relates to compounds of structural formula Ic:

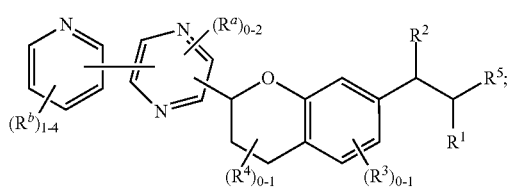

Ic or a pharmaceutically acceptable salt thereof.

In another embodiment of the present invention, the invention relates to compounds of structural formula Id:

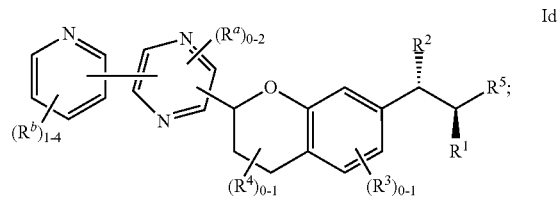

Id or a pharmaceutically acceptable salt thereof.

In another embodiment of the present invention, the invention relates to compounds of structural formula Ie:

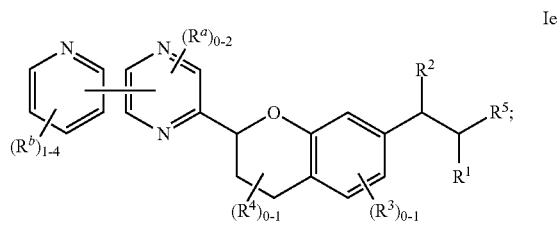

Ie or a pharmaceutically acceptable salt thereof.

In another embodiment of the present invention, the invention relates to compounds of structural formula If:

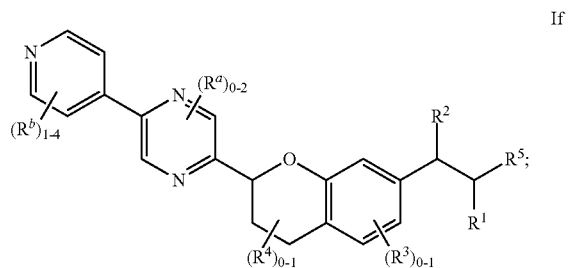

If or a pharmaceutically acceptable salt thereof.

In another embodiment of the present invention, the invention relates to compounds of structural formula Ig:

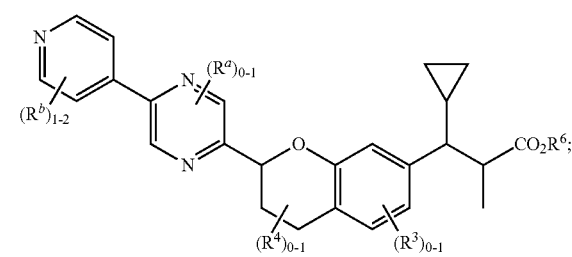

Ig or a pharmaceutically acceptable salt thereof.

In another embodiment of the present invention, the invention relates to compounds of structural formula Ih:

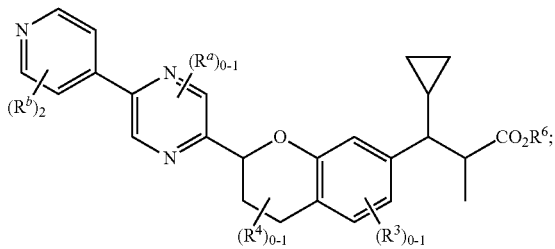

Ih or a pharmaceutically acceptable salt thereof.

In another embodiment of the present invention, the invention relates to compounds of structural formula Ii:

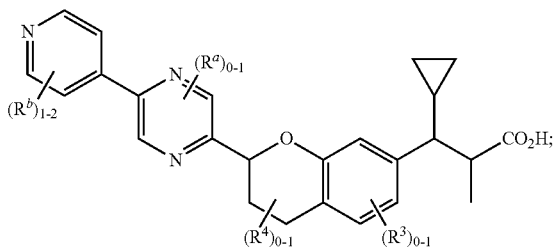

Ii or a pharmaceutically acceptable salt thereof.

In another embodiment of the present invention, the invention relates to compounds of structural formula-Ij:

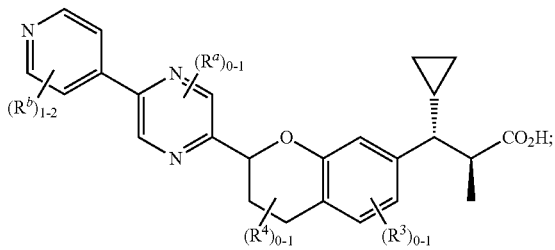

Ij or a pharmaceutically acceptable salt thereof.

In another embodiment of the present invention, the invention relates to compounds of structural formula Ik:

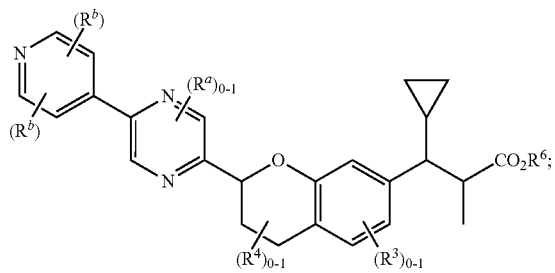

Ik or a pharmaceutically acceptable salt thereof.

In another embodiment of the present invention, the invention relates to compounds of structural formula Il:

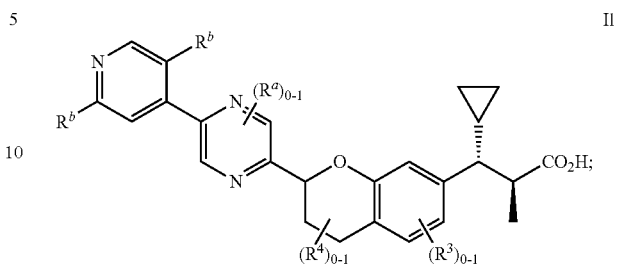

Il or a pharmaceutically acceptable salt thereof.

In another embodiment of the present invention, the invention relates to compounds of structural formula Im:

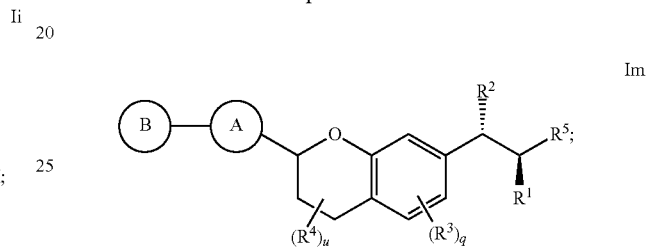

Im or a pharmaceutically acceptable salt thereof.

The compound of structural formula I includes the compounds of structural formulas Ia, Ib, Ic, Id, Ie, If, Ig, Ih, Ii, Ij, Ik, Il and Im, and pharmaceutically acceptable salts, hydrates and solvates thereof.

Another embodiment of the present invention relates to compounds of structural formula Ik:

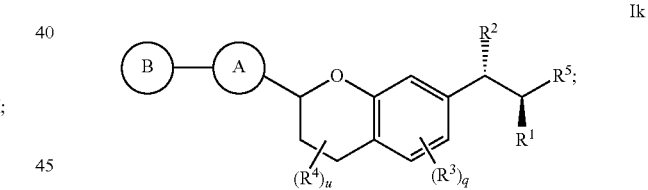

Ik wherein
A is pyrazine, wherein pyrazine is unsubstituted or substituted with one to two substituents selected from $R^a$;
B is heteroaryl, wherein heteroaryl is unsubstituted or substituted with one to five substituents selected from $R^b$;
$R^1$ is —$C_{1-10}$alkyl, wherein alkyl is unsubstituted or substituted with 1-4 substituents selected from $C_{1-6}$alkyl, halogen, and —$OC_{1-6}$alkyl;
$R^2$ is independently selected from the group consisting of: —$C_{3-6}$cycloalkyl, wherein cycloalkyl is unsubstituted or substituted with 1-4 substituents selected from $C_{1-6}$alkyl, halogen, and —$OC_{1-6}$alkyl;
$R^3$ is selected from the group consisting of: hydrogen and halogen;
$R^4$ is hydrogen or $C_{1-6}$alkylO—; or a pharmaceutically acceptable salt thereof.
$R^5$ is —$CO_2R^6$;
$R^6$ is selected from the group consisting of: hydrogen and —$C_{1-6}$alkyl, wherein each alkyl is unsubstituted or substituted with one to three substituents selected from $R^h$; and $R^a$, $R^b$, $R^h$, q, and u are as defined above;
or a pharmaceutically acceptable salt thereof.

Another embodiment of the present invention relates to compounds of structural formula Ik:

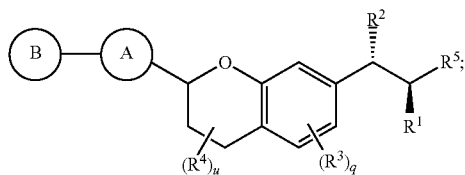

Ik wherein
A is pyrazine, wherein pyrazine is substituted with one to two substituents selected from $R^a$; B is heteroaryl, wherein heteroaryl is unsubstituted or substituted with one to five substituents selected from $R^b$;
$R^1$ is —$C_{1-10}$alkyl, wherein alkyl is unsubstituted or substituted with 1-4 substituents selected from $C_{1-6}$alkyl, halogen, and —$OC_{1-6}$alkyl;
$R^2$ is independently selected from the group consisting of:
—$C_{3-6}$cycloalkyl, wherein cycloalkyl is unsubstituted or substituted with 1-4 substituents selected from $C_{1-6}$alkyl, halogen, and —$OC_{1-6}$alkyl;
$R^3$ is selected from the group consisting of: hydrogen and halogen;
$R^4$ is hydrogen or $C_{1-6}$alkylO—; or a pharmaceutically acceptable salt thereof.
$R^5$ is —$CO_2R^6$;
$R^6$ is selected from the group consisting of: hydrogen and —$C_{1-6}$alkyl, wherein each alkyl is unsubstituted or substituted with one to three substituents selected from $R^h$; and
$R^a$, $R^b$, $R^h$, q, and u are as defined above;
or a pharmaceutically acceptable salt thereof.

Another embodiment of the present invention relates to compounds of structural formula Ik:

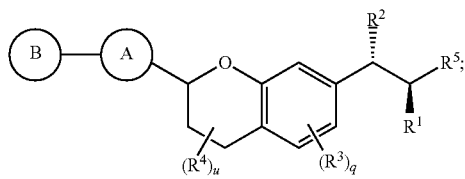

Ik wherein
A is pyrazine, wherein pyrazine is unsubstituted or substituted with one substituent selected from $R^a$;
B is pyridine, wherein pyridine is unsubstituted or substituted with one to five substituents selected from $R^b$;
$R^1$ is —$C_{1-3}$alkyl;
$R^2$ is cyclopropyl, wherein cycloalkyl is unsubstituted or substituted with 1-4 substituents selected from $C_{1-6}$alkyl, halogen, and —$OC_{1-6}$alkyl;
$R^3$ is halogen;
$R^4$ is hydrogen or $C_{1-6}$alkyl-O—;
$R^5$ is —$CO_2R^6$;
$R^6$ is hydrogen; and
$R^a$, $R^b$, q, and u are as defined above;
or a pharmaceutically acceptable salt thereof.

Another embodiment of the present invention relates to compounds of structural formula Ik:

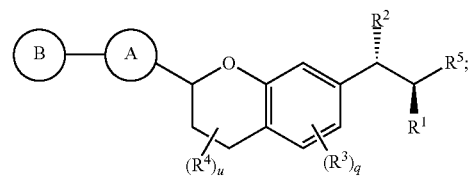

Ik wherein
A is pyrazine, wherein pyrazine is substituted with one substituent selected from $R^a$;
B is pyridine, wherein pyridine is unsubstituted or substituted with one to five substituents selected from $R^b$;
$R^1$ is —$C_{1-3}$alkyl;
$R^2$ is cyclopropyl, wherein cycloalkyl is unsubstituted or substituted with 1-4 substituents selected from $C_{1-6}$alkyl, halogen, and —$OC_{1-6}$alkyl;
$R^3$ is halogen;
$R^4$ is hydrogen or $C_{1-6}$alkyl-O—;
$R^5$ is —$CO_2R^6$;
$R^6$ is hydrogen; and
$R^a$, $R^b$, q, and u are as defined above;
or a pharmaceutically acceptable salt thereof.

Illustrative, but non-limiting, examples of the compounds of the present invention that are useful as agonists of G-protein-coupled receptor 40 (GPR40) are the following compounds:

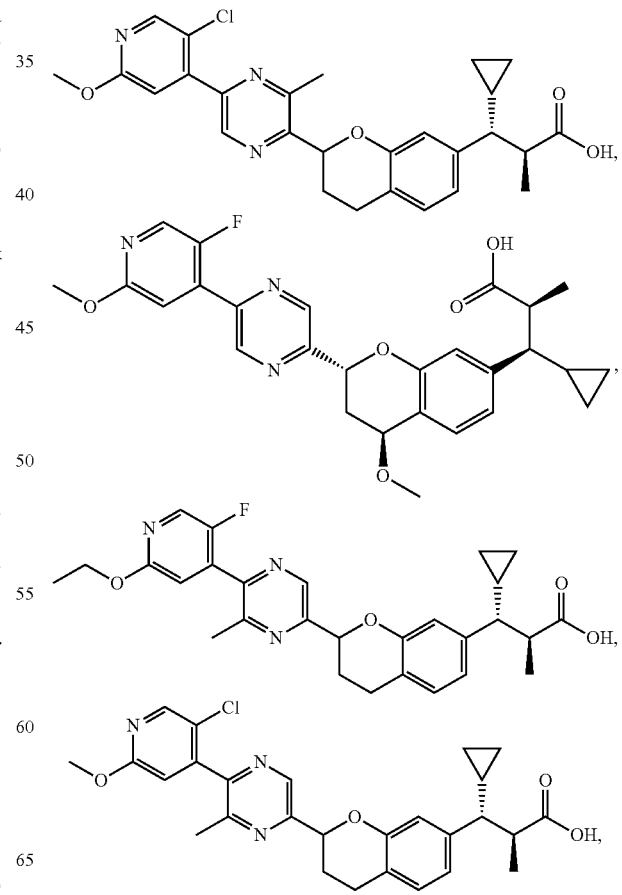

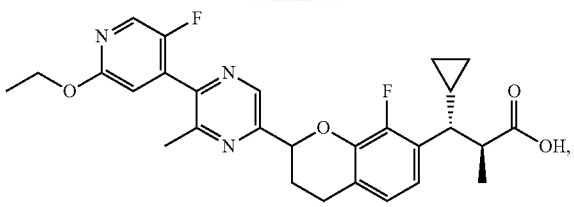
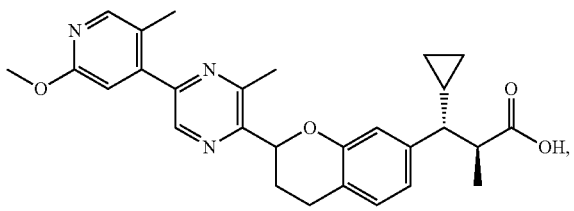
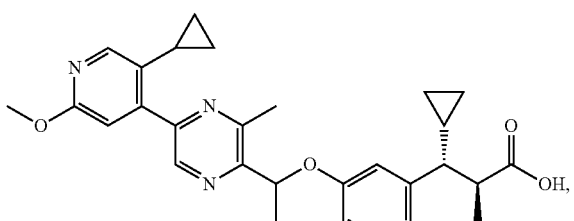
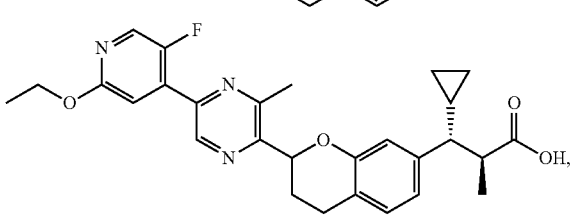
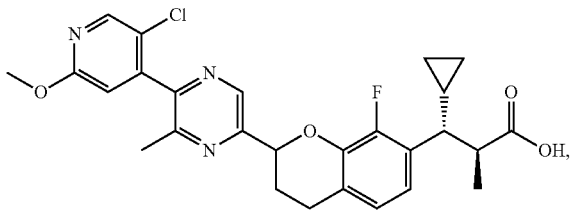
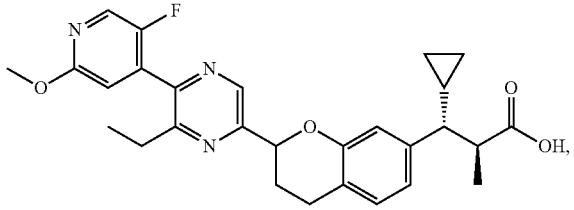
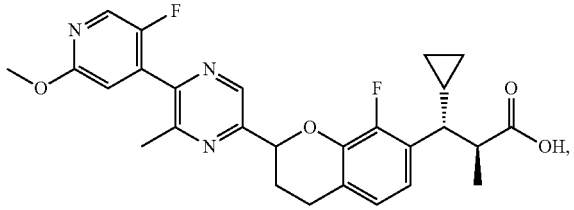
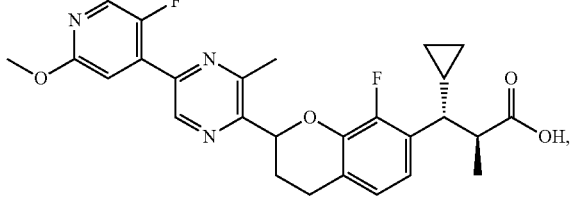

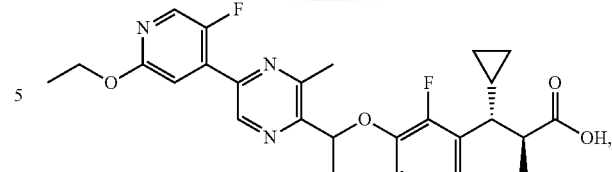
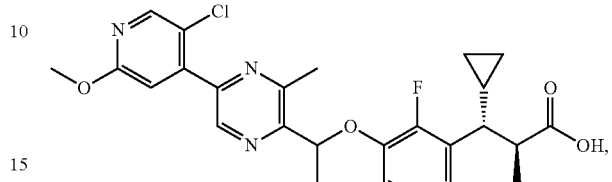
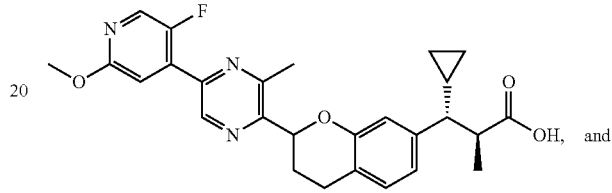

and pharmaceutically acceptable salts thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is selected from methyl and ethyl. In another embodiment of the present invention, alkyl is methyl. In another embodiment of the present invention, alkyl is ethyl.

"Alkenyl" means carbon chains which contain at least one carbon-carbon double bond, and which may be linear or branched, or combinations thereof, unless otherwise defined.

Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is cyclopropyl.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" means a saturated or partly unsaturated non-aromatic monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1, 4:3,6-dianhydromannitol, 1, 4:3,6-dianhydro[D]mannitol, hexahydrofuro[3,2-b]furan, and 2,3,3a,5,6,6a-hexahydrofuro[3,2-b]furan.

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is pyrazine. In another embodiment of the present invention, heteroaryl is pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

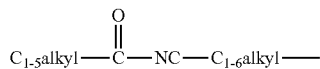

For example, —$NR^cC(O)R^e$ is equivalent to —$N(R^c)C(O)R^e$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment.

Also, the compounds of the present invention may be used for the manufacture of a medicament which may be useful for treating one or more of these diseases:
(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapo-B liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:
(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The compounds of the present invention in which A is pyrazine, optionally substituted with alkyl, and B is optionally substituted pyridine, such as compounds A-1, A-2, A-3, A-4, A-5 and A-6 in Table A, have the unexpected benefit of a 2 to 5-fold decrease in unbound human hepatocyte clearance compared to the compounds in which A is pyrazine and B is phenyl, and compared to the compounds in which A is pyridine or phenyl and B is pyridine, such as compounds B-1, B-2 and B-3 in Table B.

Due to their decreased unbound human hepatocyte clearance, the compounds of the present invention in which A is pyrazine, optionally substituted with alkyl, and B is optionally substituted pyridine, such as compounds A-1, A-2, A-3, A-4, A-5 and A-6 in Table A, are expected to require a lower human dose than the compounds in which A is pyrazine and B is phenyl, and a lower human dose than the compounds in which A is pyridine or phenyl and B is pyridine, such as compounds B-1, B-2 and B-3 in Table B.

TABLE A

Human unbound hepatocyte clearance for compounds of the present invention.

| Compound | Structure | Unbound Human Hepatocyte Clearance |
|---|---|---|
| A-1 Diastereoisomer 1* | 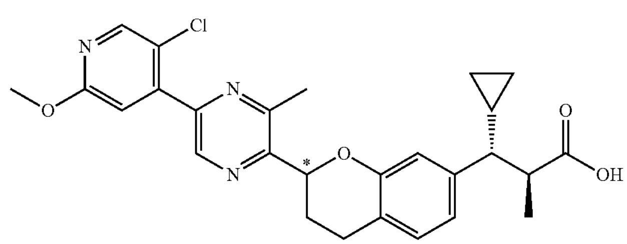 [SMILES: COc1cc(-c2cnc(C3CCc4ccc([C@H](C5CC5)[C@H](C)C(=O)O)cc4O3)c(C)n2)c(Cl)cn1] | 25 |

TABLE A-continued

Human unbound hepatocyte clearance for compounds of the present invention.

| Compound | Structure | Unbound Human Hepatocyte Clearance |
|---|---|---|
| A-1 Diastereoisomer 2* | 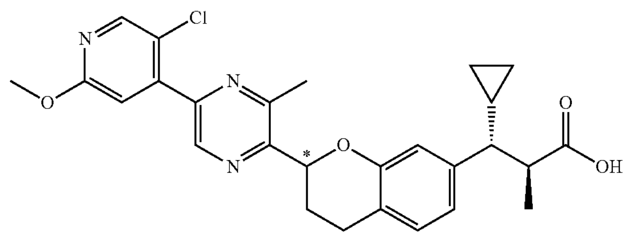 [SMILES: COc1cc(-c2cnc(C3CCc4ccc([C@H](C5CC5)[C@H](C)C(=O)O)cc4O3)c(C)n2)c(Cl)cn1] | 50 |
| A-2 Diastereoisomer 1* | 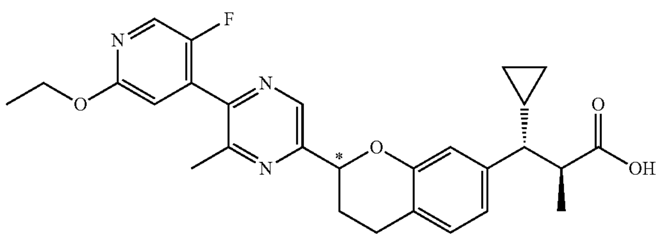 [SMILES: CCOc1cc(-c2ncc(C3CCc4ccc([C@H](C5CC5)[C@H](C)C(=O)O)cc4O3)nc2C)c(F)cn1] | 31 |
| A-2 Diastereoisomer 2* | 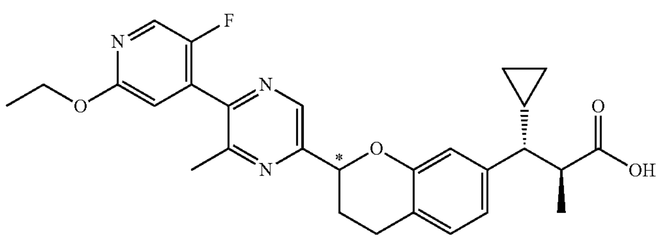 [SMILES: CCOc1cc(-c2ncc(C3CCc4ccc([C@H](C5CC5)[C@H](C)C(=O)O)cc4O3)nc2C)c(F)cn1] | 25 |
| A-3 Diastereoisomer 1* | 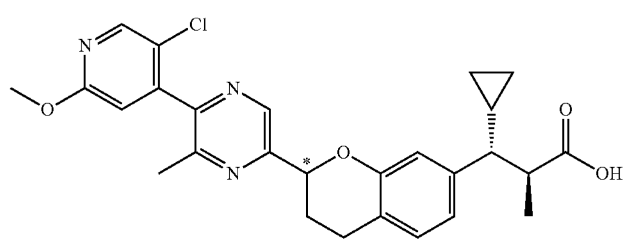 [SMILES: COc1cc(-c2ncc(C3CCc4ccc([C@H](C5CC5)[C@H](C)C(=O)O)cc4O3)nc2C)c(Cl)cn1] | 23 |
| A-3 Diastereoisomer 2* | 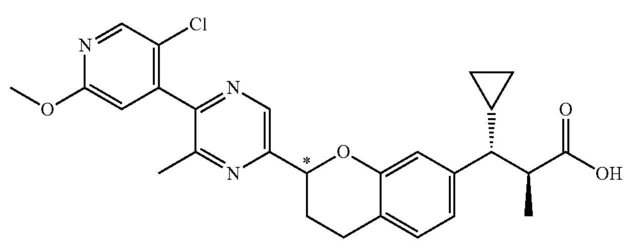 [SMILES: COc1cc(-c2ncc(C3CCc4ccc([C@H](C5CC5)[C@H](C)C(=O)O)cc4O3)nc2C)c(Cl)cn1] | 39 |
| A-4 | 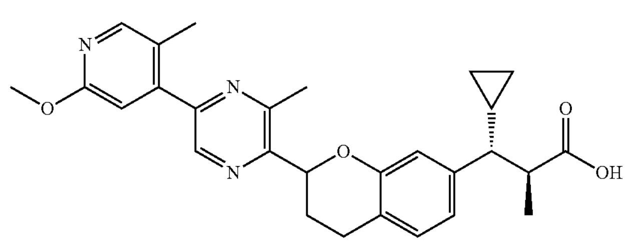 [SMILES: COc1cc(-c2cnc(C3CCc4ccc([C@H](C5CC5)[C@H](C)C(=O)O)cc4O3)c(C)n2)c(C)cn1] | 15 |

TABLE A-continued
Human unbound hepatocyte clearance for compounds of the present invention.
| Compound | Structure | Unbound Human Hepatocyte Clearance |
|---|---|---|
| A-5 | 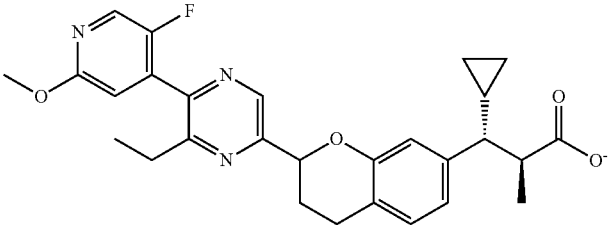 [SMILES: CCc1nc(C2CCc3ccc([C@H](C4CC4)[C@H](C)C(=O)[O-])cc3O2)cnc1-c1cc(OC)ncc1F] | 83 |
| A-6 Diastereoisomer 1* | 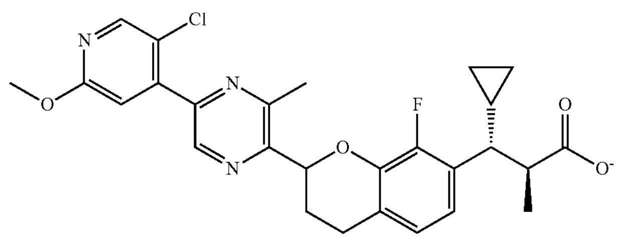 | 66 |
| A-6 Diastereoisomer 2* | 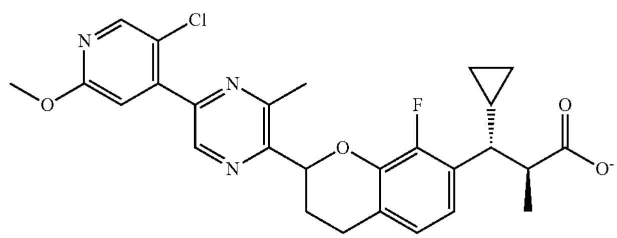 [SMILES: COc1cc(-c2cnc(C3CCc4ccc([C@H](C5CC5)[C@H](C)C(=O)[O-])c(F)c4O3)c(C)n2)c(Cl)cn1] | 71 |
TABLE B
Human unbound hepatocyte clearance for compounds B-1, B-2 and B-3
| Compound | Structure | Unbound Human Hepatocyte Clearance |
|---|---|---|
| B-1 Diastereoisomer 1* | 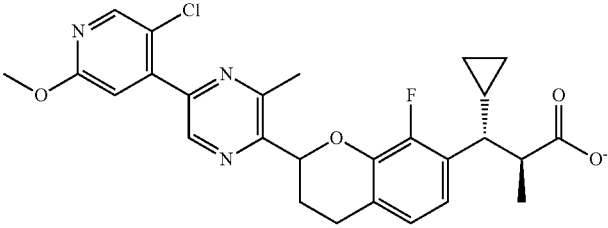 [SMILES: COc1cc(-c2cnc(C3CCc4ccc([C@H](C5CC5)[C@H](C)C(=O)[O-])c(F)c4O3)c(C)n2)c(Cl)cn1] | 183 |
| B-1 Diastereoisomer 2* | 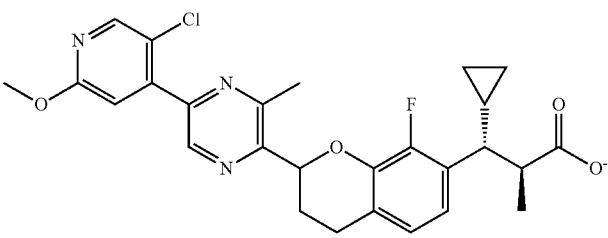 | 206 |

TABLE B-continued

Human unbound hepatocyte clearance for compounds B-1, B-2 and B-3

| Compound | Structure | Unbound Human Hepatocyte Clearance |
|---|---|---|
| B-2 Diastereoisomer 1* | [structure] | 1405 |
| B-2 Diastereoisomer 2* | [structure] | 645 |
| B-3 Diastereoisomer 1* | [structure] | 122 |
| B-3 Diastereoisomer 2* | [structure] | 182 |

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated ($\geq$140 mmHg/$\geq$90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e., cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia- Pacific, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese;

glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-NH2) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), 5-23521, and compounds disclosed in WO 04/022004, and WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATl-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl) phenyl)-methoxy)phenyl)iso, 5-(4-((3-(2-methyl-6-(3-hydroxypropoxy)pyridine-3-yl)-2-methylphenyl)methoxy) phenyl)-isothiazole-3-ol 1-oxide, and 5-[4-[[3-[4-(3-aminopropoxy)-2,6-dimethylphenyl]phenyl]-methoxy] phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARa agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GaxoSmithkline), SR 103912, QRX401, LN-6691 (Lion Bioscience), and those disclosed in WO 02/064125, WO 04/045511, and the like; (11) LXR receptor modulators such as GW 3965 (GaxoSmithkline), T9013137, and XTCO179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14)

PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; lisinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, F16828K, and RNH6270, and the like; (9) a/O adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XENO10, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CBT (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vemalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and 0-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GaxoSmithkline), A224940 (Abbott), A798 (Abbott), ATC0175/AR224349 (Arena Pharmaceuticals), GW803430 (GaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 1/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman LaRoche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) 3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 1/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2)inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone Ragonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TSO21, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7™ Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) McSr (melanocortin 5 receptor) modulators, such as those disclosed in WO 97/19952, WO 00/15826, WO 00/15790, US 20030092041, and the like; (50) Brain derived neutotropic factor (BDNF), (51) MeIr (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GaxoSmithkline), SB271046 (GaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55)C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-diabetic compounds, anti-obesity compounds and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI). LCMS analyses of the examples were performed using one of the following two methods: Method A (Instrument: Waters Acquity UPLC system, Column: Waters BEH C18 column, 1.0×50 mm, 1.7 um; column temperature: 50° C.; Mobile phases: A: $H_2O$ with 0.05% (v/v) TFA, and B: MeCN with 0.05% (v/v) TFA; Gradient: 0-2 min, 10% to 99% B; Mass Spectrometer: Waters SQD MS detector, Electrospray positive ion mode); and Method B (Instrument: Agilent 1200 Series HPLC; Column: Agilent TC-C18, 50×2.1 mm, 5 μm, 50° C.; Flow Rate: 0.8 mL/min; Mobile Phases: A: $H_2O$ with 0.04% (v/v) TFA, and B: MeCN with 0.02% (v/v) TFA; Gradient: Time 0 min: 90% A and 10% B; Time 0.4 min: 90% A and 10% B; Time 3.4 min: 0% A and 100% B; Time 4 min: 0% A and 100% B; and Time 4.01 min: 90% A and 10% B; Flow Rate: 0.8 mL/min; and Detector: Agilent 6110 or 6140 or 1956 single quadrupole MSD and ELSD, Electrospray positive ion mode.

List of Abbreviations

Ac is acetyl; AcO is acetoxy; $Ac_2O$ is acetic anhydride; Alk is alkyl; APCI is atmospheric pressure chemical ionization; aq or aq. is aqueous; Ar is aryl; atm is atmosphere; Boc or BOC is tert-butoxycarbonyl; Bn—O is phenyl-$CH_2$—O or benzyloxy; Br is broad; BuLi is n-butyllithium; $Bu_3P$ is tributylphosphine; t-BuOK is potassium tert-butoxide; ° C. is degrees celsius; Cbz is benzyloxycarbonyl; $CH_2Cl_2$ is dichloromethane; conc or conc. is concentrated; d is doublet; DAST is (diethylamino)sulfur trifluoride; DBU is 1,8-Diazabicyclo(5.4.0)undec-7-ene; DIAD is diisopropyl azodicarboxylate; DCM is dichloromethane; DIPEA is N,N-diisopropyl-ethylamine; DMAP is 4-dimethylaminopyridine; DMF is N,N-dimethyl-formamide; DMSO is dimethylsulfoxide; dppf is 1,1'-Bis(diphenyl-phosphino)ferrocene; ESI is electrospray ionization; EA or EtOAc is ethyl acetate; Et is ethyl; EtMgBr is ethyl magnesium bromide; EtOH is ethanol; eq or equiv is equivalent; g is gram(s); h or hr or hrs is hour(s); hex is hexanes; HPLC is high pressure liquid chromatography; HOAc or AcOH is acetic acid; HTP is high throughput purification; kg is kilogram(s); IPA is isopropanol; IPAc is isopropyl acetate; KOH is potassium hydroxide; KOAc is potassium acetate; KOTMS is potassium trimethylsilanolate; L is liter; LAH is lithium aluminum hydride; LC-M is molar; MS is liquid chromatography-mass spectroscopy; LDA is lithium diisopropyl amide; LiOH is lithium hydroxide; m is multiplet; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeMgBr is methyl magnesium bromide; MeCN is acetonitrile; MeOH is methyl alcohol or methanol; $MgSO_4$ is magnesium sulfate; MPLC is medium pressure liquid chromatography; MS is mass spectroscopy; MsCl or Ms-Cl is methane sulfonyl chloride; N is normal; $Na(AcO)_3BH$ is sodium triacetoxy borohydride; NaOH is sodium hydroxide; NaOtBu is sodium tert-butoxide; $Na_2SO_4$ is sodium sulfate; $NH_4OAc$ is ammonium acetate; NBS is N-bromo succinamide; NIS is N-iodo succinamide; nM is nanomolar; nm is nanometer; NMO is 4-methyl morpholine N-oxide; NMP is 1-methyl-2-pyrrolidinone; NMR is nuclear magnetic resonance spectroscopy; paraform is para-formaldehyde; PE is petroleum ether; PG is protecting group; $P(Cy)_3$ is tricyclohexyl phosphine; $Pd_2(dba)3$ is tris(dibenzylideneacetone)-dipalladium(0); $Pd[P(t-Bu)_3]_2$ is bis(tri-tert-butylphosphine) palladium (0); $Pd(dppf)Cl_2$ is [1,1'-bis(diphenyl-phosphino)-ferrocene]dichloro-palladium (II); PMB is para-methoxybenzyl; PMBCl is para-methoxybenzyl chloride; precat is precatalyst; prep is preparative; prep. TLC or prep-TLC, or prep TLC is preparative thin layer chromatography; RBF is round bottom flask; RCM is ring closing metathesis reaction; rt or r.t. or RT is room temperature; s is singlet; sat or sat. is saturated; SFC is supercritical fluid chromatography; S-Phos is 2-Dicyclohexylphosphino-2',6'-dimethoxybiphenyl; S-Phos(Pd) is chloro(2-dicyclohexyl-phosphino-2',6'-dimethoxy-1,1'-biphenyl)[2-(2-aminoethylphenyl)]-palladium(II) [CAS-No. 1028206-58-7]; S-Phos precatalyst 2nd generation is Chloro(2-dicyclohexyl-phosphino-2',6'-dimethoxy-1,1'-biphenyl)[2-(2'-amino-1,1'-biphenyl)]palladium(II), SPhos-Pd-G2) [CAS-No. 1375325-64-6]; tis triplet; TBAF is tetrabutylammonium fluoride; TBSC is tert-butyl dimethylsilyl chloride; TBPA is tertiary butyl hydrogen peroxide; TBTU is N,N,N',N'-Tetramethyl-O-(benzotriazol-1-yl)uronium tetrafluoroborate; TEA is triethyl amine; THF is tetra-hydrofuran; $Ti(OiPr)_4$ is titanium isopropoxide; TFA is trifluoroacetic acid; $Tf_2O$ is trifluoromethanesulfonic anhydride; TLC is thin-layer chromatography; TosCl is p-toluene sulfonyl chloride; pTSA, pTsOH and TsOH is p-toluenesulfonic acid; RuCl[(S,S)-TsDPEN] (mesitylene) is [N-[(1S,2S)-2-(Amino-κN)-1,2-diphenyl-ethyl]-4-methylbenzenesulfonamidato-xN]chloro[(1,2,3,4,5,6-η)-1,3,5-trimethylbenzene]-ruthenium; xphos or XPhos is 2-Dicyclohexylphosphino-2',4',6'-triisopropylbiphenyl; v/v is volume/volume; t-butyl x-phos palladacycle G1 is Chloro[2-(di-tert-butylphosphino)-2',4',6'-triisopropyl-1,1'-biphenyl][2-(2-aminoethyl)phenyl)-]palladium(II) and $2^{nd}$ generation XPhos pre catalyst is chloro(2-dicyclohexylphos-phino-2',4',6'-triisopropyl-1,1'-biphenyl)[2-(2'-amino-1,1'-biphenyl)]palladium(II).

Several methods for preparing the compounds of this invention are illustrated in the following Schemes, Intermediates and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided for the purpose of illustration only and are not to be construed as limitations on the disclosed invention. All temperatures are degrees Celsius unless otherwise noted.

The compounds of the present invention may be prepared according to the synthetic route provided in the General Scheme below. Compound i, wherein X can be a leaving group such as chloro, bromo, iodo and triflyl, can undergo Suzuki cross coupling with boronic acid iia or boronate iib to afford intermediate iii. A single-step Dibal-H reduction or two-step sodium borohydride reduction, followed by oxidation with Dess-Martin periodinane will afford aldehyde iv. Addition of a vinyl Grignard solution or a solution of vinyl Grignard in the presence of zinc chloride to aldehyde iv will provide the allylic alcohol v. Heck cross-coupling of v and iodophenol vi in refluxing toluene with t-butyl x-phos palladacycle G1 and dicyclohexylmethyl-amine will provide either vii, viii or a mixture of the two. Compound viii can be converted to vii by treatment with a base such as DBU in toluene. Ketone vii can be reduced to alcohol ix using reagents such as sodium borohydride or asymmetrically using a Noyori reduction or a ketoreductase. Alternatively, compound viii can be treated with a hydrogen atmosphere in the presence of platinum (IV) oxide to afford alcohol ix. Mitsonobu cyclization of compound ix will afford chroman x. Ester hydrolysis of chroman x with aqueous LiOH in MeOH or MeOH/THF mixtures will afford acid xi. Separation of the mixture of chroman isomers present in xi via chiral chromatography will afford the desired diastereomers xia and xib.

General Scheme

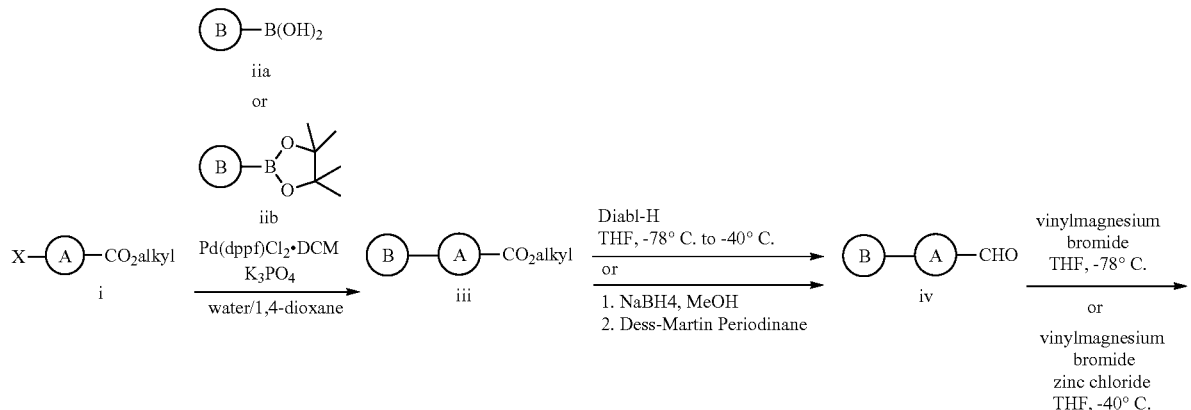

-continued

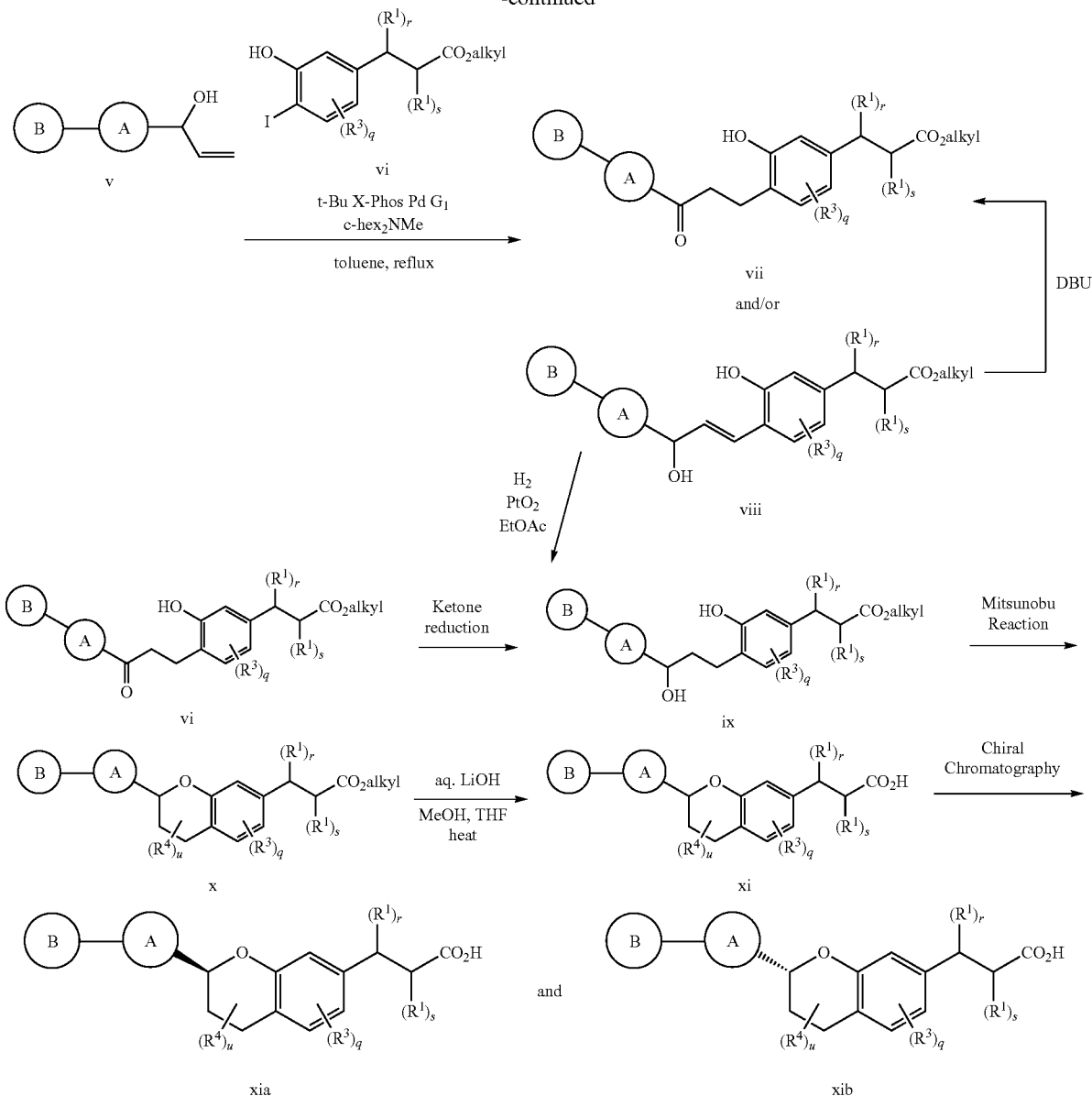

Intermediate 1

Methyl 5-bromo-3-methylpyrazine-2-carboxylate

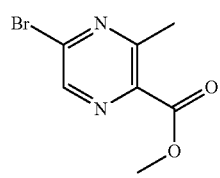

Step 1: diethyl 2-(6-chloropyrazin-2-yl)malonate

A 20-L, 4-necked round-bottom flask was charged with sodium hydride (550 g, 13.75 mol, 2.03 equiv), tetrahydrofuran (10 L) and 2,6-dichloropyrazine (1000 g, 6.76 mol, 1.00 equiv). To the reaction was added diethyl malonate (1800 g, 11.25 mol, 2.31 equiv) dropwise with stirring at <15° C. The resulting solution was heated at reflux for 12 h and then cooled to room temperature. The reaction was then quenched by the addition of ice water (500 mL). The resulting solution was then extracted with ethyl acetate (3×2000 mL) and the combined organic layers were dried over anhydrous sodium sulfate, filtered and concentrated under vacuum to give the title compound, which was used in the subsequent step without further purification.

Step 2: 2-(6-chloropyrazin-2-yl)acetic Acid

A 20-L, 4-necked round-bottom flask was charged with water (12 L) and sodium hydroxide (1200 g, 30.00 mol, 4.33 equiv). To this mixture was added dropwise diethyl 2-(6-chloropyrazin-2-yl)malonate (2000 g, 7.35 mol, 1 equiv) at <10° C. The reaction mixture was stirred for 12 h at room temperature, then the pH was adjusted to 6-7 with HCl (2M, aqueous). The resulting mixture was extracted with ethyl acetate (3×5000 mL). The combined organic layers were dried over anhydrous sodium sulfate, filtered and concentrated under vacuum to give the title compound, which was used in the next step without further purification

Step 3: 2-chloro-6-methylpyrazine

A 5-L pressure tank reactor was charged with water (3.5 L) and 2-(6-chloropyrazin-2-yl)acetic acid (850 g, 4.94 mol, 1.00 equiv). The reaction mixture was stirred for 24 h at 130° C., and then cooled to room temperature. The reaction mixture was extracted with ethyl acetate (3×3000 mL). The combined organic layers were dried over anhydrous sodium sulfate, filtered and concentrated under vacuum to give the title compound, which was used in the next step without further purification.

Step 4: 6-methylpyrazin-2-amine

A 5-L pressure tank reactor was charged with 2-chloro-6-methylpyrazine (400 g, 3.11 mol, 1.00 equiv) and ammonium hydroxide (concentrated, 3500 mL). The reaction mixture was stirred for 1 day at 130° C. and then cooled to room temperature and extracted with ethyl acetate (6×1 L). The combined organic layers were dried over anhydrous sodium sulfate, filtered and concentrated under vacuum to give the title compound, which was used in the next step without further purification.

Step 5: 5-bromo-6-methylpyrazin-2-amine

A 10-L, 4-necked round-bottom flask was charged with 6-methylpyrazin-2-amine (590 g, 5.41 mol, 1.00 equiv), chloroform (7 L) and NBS (960 g, 5.39 mol, 1.29 equiv). The reaction mixture was stirred for 12 h at room temperature. The resulting solid was filtered out and the filtrate was concentrated under vacuum to give the title compound, which was used in the next step without further purification.

Step 6: methyl 5-amino-3-methylpyrazine-2-carboxylate

A 5 L pressure tank reactor was charged with 5-bromo-6-methylpyrazin-2-amine (510 g, 2.71 mol, 1.00 equiv), triethylamine (830 g, 8.22 mol, 3.02 equiv), methanol (3.5 L) and Pd(dppf)Cl₂ (60 g). The reactor was pressurized with CO gas (10 atm) and was stirred for 24 h at 70° C. The pressure was then released; and the resulting solid was filtered off. The filtrate was concentrated under vacuum. Water was added to the resulting residue and the mixture was extracted with ethyl acetate (6×1 L). The combined organic layers were dried over anhydrous sodium sulfate and concentrated under vacuum to give the title compound, which was used in the next step without further purification.

Step 7: methyl 5-hydroxy-3-methylpyrazine-2-carboxylate

A 5 L beaker was charged with water (2 L), sulfuric acid (concentrated, 180 mL) and methyl 5-amino-3-methylpyrazine-2-carboxylate (50 g, 299.11 mmol, 1.00 equiv). Then a solution of NaNO₂ (64 g, 927.54 mmol, 2.83 equiv) in water (100 mL) was added dropwise with stirring at <5° C. The reaction was stirred for 3 h at <5° C., then the pH was adjusted to pH 7 with sodium hydroxide. The resulting mixture was concentrated under vacuum. The resulting residue was washed with methanol (3×1 L). The methanol filtrate was concentrated under vacuum to give the title compound, which was used in the next step without further purification.

Step 8: methyl, 5-bromo-3-methylpyrazine-2-carboxylate

A 2 L, 3-necked round-bottom flask was charged with phosphoryl tribromide (100 g, 348.81 mmol, 1.96 equiv), 1,4-dioxane (1 L) and methyl 5-hydroxy-3-methylpyrazine-2-carboxylate (30 g, 178.41 mmol, 1.00 equiv). The reaction mixture was heated to reflux for 12 h, then cooled to room temperature, and quenched by the addition of ice water (200 mL). The resulting solution was extracted with ethyl acetate (4×1 L). The combined organic layers were dried over anhydrous sodium sulfate, filtered and concentrated under vacuum. The resulting residue was purified by silica gel chromatography eluting with ethyl acetate:petroleum ether (1:20) to give the title compound.

Intermediate 2

Methyl 5-chloro-6-methylpyrazine-2-carboxylate

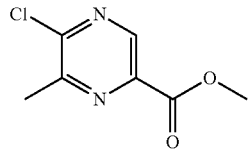

Step 1. 5-methyl-6-oxo-1,6-dihydropyrazine-2,3-dicarbonitrile

To a stirred solution of 2,3-diaminofumaronitrile 1 (80 g, 0.740 mol) in methanol (800 mL) was added methyl pyruvate (66.85 mL, 0.740 mol) at room temperature. The reaction mixture was heated at 75° C. for 3 h, then charcoal (12 g) was added and the reaction was heated at 70° C. for 15 min. The reaction mixture was then filtered through a Celite™ pad; and the pad was rinsed with methanol. The combined filtrates were concentrated under reduced pressure to afford the title compound, which was used in the next step without further purification.

Step 2. 6-methyl-5-oxo-4,5-dihydropyrazine-2-carboxylic Acid

A stirred suspension of 5-methyl-6-oxo-1,6-dihydropyrazine-2,3-dicarbonitrile (95 g, 0.593 mol) in concentrated HCl (950 mL) was heated at 100° C. for 8 h. Then the reaction mixture was cooled to 5° C. to 10° C. The precipitated solid was filtered and dried to give the title compound, which was used in the next step without further purification.

Step 3. methyl 6-methyl-5-oxo-4,5-dihydropyrazine-2-carboxylate

To a stirred solution of 6-methyl-5-oxo-4,5-dihydropyrazine-2-carboxylic acid (70 g, 0.454 mol) in methanol (2.1 L)

was added dropwise thionyl chloride (131.78 mL, 1.817 mol) at 0° C. over 1 h. The reaction mixture was then heated at 70° C. for 18 h, then concentrated to dryness to afford a crude residue. The residue was stirred with ethyl acetate, filtered and dried under vacuum to give the title compound.

Step 4. methyl 5-chloro-6-methylpyrazine-2-carboxylate

To a stirred solution of methyl 6-methyl-5-oxo-4,5-dihydropyrazine-2-carboxylate (75 g, 0.446 mol) in phosphorous oxychloride (375 mL) was added DMF (5 mL) at 5-10° C. The reaction mixture was heated to 110° C. for 3 h. Then the POCl₃ was distilled off from the reaction mixture. The resulting residue was quenched with ice-cold water (300 mL) and extracted with dichloromethane (3×500 mL). The combined organic layers were washed with water (500 mL), brine (300 mL), dried over anhydrous sodium sulfate and concentrated to afford a crude residue. The crude residue was adsorbed on 150 g of 100-200 silica gel, which was then loaded over a pre-packed column with silica gel and gradient eluted with 12% ethyl acetate/petroleum ether to 18% ethyl acetate/petroleum ether to give the title compound.

Intermediate 3 Methyl 5-(5-chloro-2-methoxypyridin-4-yl)-3-methylpyrazine-2-carboxylate

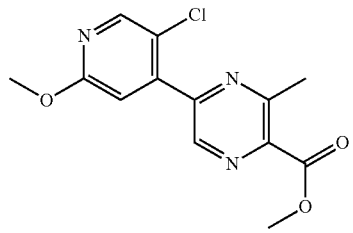 [SMILES: COC(=O)c1ncc(-c2cc(OC)ncc2Cl)nc1C]

To a nitrogen-purged solution of methyl 5-bromo-3-methylpyrazine-2-carboxylate (Intermediate 1, 18 g, 78 mmol), (5-chloro-2-methoxypyridin-4-yl)boronic acid (17.52 g, 93 mmol) and PdCl₂(dppf) (5.70 g, 7.79 mmol) in THF (200 ml) and water (40.0 ml) was added K₃PO₄ (49.6 g, 234 mmol) under a nitrogen atmosphere. The reaction mixture was heated to a vigorous reflux at 100° C. for 2h. Then the reaction was allowed to slowly cool to room temperature overnight with stirring. The reaction was stirred at room temperature for 72h, then partitioned between ethyl acetate (150 ml) and water (150 ml) and stirred for 30 min. The layers were separated, and the aqueous layer was extracted with ethyl acetate. The organic layers were combined, washed with brine, dried over anhydrous Na₂SO₄, filtered and evaporated to afford a crude residue. The residue was purified via column chromatography on silica gel (ISCO RediSep Gold 220 g silica gel column, gradient elution with 0% to 100% EtOAc in hexanes) to give the title compound.

TABLE 1

Intermediates 4-8 were prepared utilizing a method similar to that outlined in the Intermediate 3 from the appropriate starting materials

| Intermediate | Structure |
| --- | --- |
| 4 | (5-fluoro-2-methoxypyridin-4-yl connected to 3-methylpyrazine-2-carboxylate methyl ester) |
| 5 | (5-fluoro-2-ethoxypyridin-4-yl connected to 3-methylpyrazine-2-carboxylate methyl ester) |
| 6 | (5-fluoro-2-methoxypyridin-4-yl connected to 6-methylpyrazine-2-carboxylate methyl ester) |
| 7 | (5-fluoro-2-ethoxypyridin-4-yl connected to 6-methylpyrazine-2-carboxylate methyl ester) |
| 8 | (5-chloro-2-methoxypyridin-4-yl connected to 6-methylpyrazine-2-carboxylate methyl ester) |

Intermediate 9

(5-(5-chloro-2-methoxypyridin-4-yl)-3-methylpyrazin-2-yl)methanol

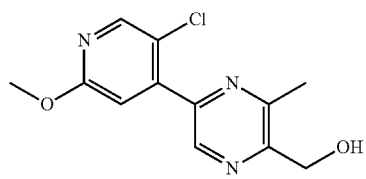 [SMILES: COc1cc(-c2cnc(CO)c(C)n2)c(Cl)cn1]

Sodium borohydride (7.73 g, 204 mmol) was added over 3 minutes to a stirred, 0° C. suspension of methyl 5-(5-chloro-2-methoxypyridin-4-yl)-3-methylpyrazine-2-carboxylate (15 g, 51.1 mmol) in MeOH (218 ml). The reaction mixture was stirred at 0° C. for 90 min, then MeOH (100 mL) was added. The reaction mixture was poured into a solution of NH$_4$C(saturated, aqueous, 600 mL). Then EtOAc (500 mL) and water (100 mL) were added and the biphasic mixture was stirred until it went clear. The layers were separated and the aqueous layer was extracted with ethyl acetate (400 mL). The organic layers were combined, washed with brine, dried over anhydrous Na$_2$SO$_4$, filtered and evaporated to a minimal volume. The resulting precipitate was collected via filtration, washed with cold EtOAc and dried under vacuum to give the title compound. The filtration mother liquors were combined and concentrated to afford a crude orange residue, which was purified via column chromatography on silica gel (ISCO RediSep Gold 220 g silica gel column, gradient elution with 0% to 100% EtOAc in hexanes) to afford an additional amount of the title compound.

Intermediate 10

(5-(5-fluoro-2-methoxypyridin-4-yl)-6-methylpyrazin-2-yl)methanol

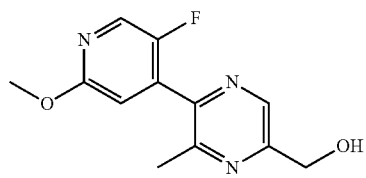 [SMILES: COc1cc(-c2ncc(CO)nc2C)c(F)cn1]

A mixture of Intermediate 6 (4 g, 14.43 mmol) in THF (100 ml) was cooled to −78° C. and stirred for 5 min. Then diisobutylaluminum hydride (1 M in THF, 21.64 ml, 21.64 mmol) was added over 5 min. The reaction mixture was slowly warmed up to 0° C. and stirred at 0° C. for 1 h. To the mixture was added additional diisobutylaluminum hydride (1 M in THF, 10.10 ml, 10.10 mmol), and the reaction was stirred for 30 min at 0° C. Then the reaction mixture was quenched with water and NH$_4$Cl (saturated, aqueous) and with CH$_2$Cl$_2$ (2×). The organic layers were combined, dried over anhydrous MgSO$_4$, filtered and evaporated. The resulting residue was re-dissolved in DCM and purified by silica gel chromatography (80 g ISCO RediSep Rf column, gradient elution, 0 to 100% EtOAc in hexanes) to give the title compound.

TABLE 2

Intermediates 11-12 were prepared utilizing a method similar to that outlined in the Intermediate 10 from the appropriate starting materials

| Intermediate | Structure |
|---|---|
| 11 | 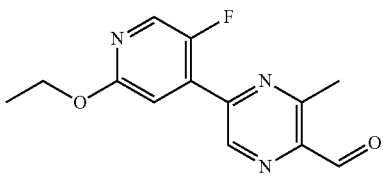 [SMILES: CCOc1cc(-c2cnc(C=O)c(C)n2)c(F)cn1] |
| 12 | 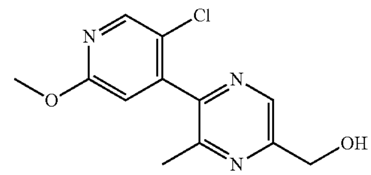 |

Intermediate 13

5-(2-ethoxy-5-fluoropyridin-4-yl)-3-methylpyrazine-2-carbaldehyde

Diisobutylaluminum hydride (1 M in THF, 9.89 ml, 9.89 mmol) was added to a stirred, −40° C. mixture of methyl 5-(2-ethoxy-5-fluoropyridin-4-yl)-3-methylpyrazine-2-carboxylate (Intermediate 5, 1.44 g, 4.94 mmol) in THF (49.4 ml). The reaction mixture was stirred at −40° C. for 2h, then poured into a solution of sodium potassium tartrate (100 mL, 30% aqueous). Then ethyl acetate (100 mL) was added and the reaction mixture was stirred for 1 h. Then the reaction mixture layers were separated and the aqueous layer was extracted with ethyl acetate. The organic layers were combined, washed with brine, dried over anhydrous Na$_2$SO$_4$, filtered and evaporated. The resulting residue was purified via column chromatography on silica gel (ISCO RediSep Gold 40 g silica gel column, gradient elution with 0% to 70% EtOAc in hexanes) to give the title compound.

Intermediate 14

(5-(2-(2,2-difluoroethoxy)-5-fluoropyridin-4-yl)-3-methylpyrazin-2-yl)methanol

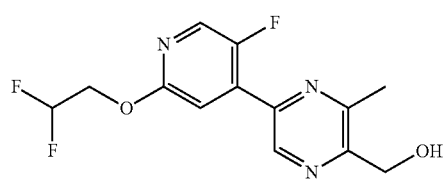 [SMILES: Cc1nc(-c2cc(OCC(F)F)ncc2F)cnc1CO]

Step 1: 2-(2,2-difluoroethoxy)-5-fluoropyridine 2,2-Difluoroethanol (7.13 g, 87 mmol) was added to a solution of NaH (3.48 g, 87 mmol) in THF (80 ml) at 0° C. The reaction was stirred for 30 minutes, followed by the dropwise addition of 2,5-difluoropyridine (10 g, 87 mmol). The reaction mixture was poured into water (20 mL), and extracted with petroleum ether (30 mL×3). The combined organic layers were washed with brine (saturated, 50 mL), dried over anhydrous $Na_2SO_4$, filtered and concentrated to give the title compound, which was used in the next step without further purification.

Step 2: (2-(2,2-difluoroethoxy)-5-fluoropyridin-4-yl)boronic Acid

Lithium diisopropylamide (2 M in THF, 14.68 ml, 29.4 mmol) was added to a solution of 2-(2,2-difluoroethoxy)-5-fluoropyridine (4 g, 22.58 mmol) in THF (20 ml) at −78° C. The reaction mixture was stirred for 30 minutes, then triisopropyl borate (5.52 g, 29.4 mmol) was added dropwise. The reaction mixture was then stirred at −78° C. for 1 hour, then aqueous NaOH (1 M, 10 mL) was added, followed by water (20 mL). The reaction mixture was washed with ethyl acetate (20 mL×3). The aqueous layer was neutralized with HCl (aqueous, 6N) to pH=5-6, then extracted with DCM (30 mL×3). The organic layers were combined, dried over anhydrous $MgSO_4$, filtered and purified by column chromatography ($SiO_2$, gradient elution, petroleum ether:EtOAc 20:1 to 1:1) to give the title compound.

Step 3: methyl 5-(2-(2,2-difluoroethoxy)-5-fluoropyridin-4-yl)-3-methylpyrazine-2-carboxylate To a solution of (2-(2,2-difluoroethoxy)-5-fluoropyridin-4-yl)boronic acid (2.104 g, 9.52 mmol), methyl 5-bromo-3-methylpyrazine-2-carboxylate (Intermediate 1, 2 g, 8.66 mmol) and $K_2CO_3$ (3.59 g, 26.0 mmol) in 1,4-dioxane (20 ml) and water (5 ml), was added Pd(dppf)$Cl_2$ (0.317 g, 0.433 mmol). The reaction mixture was stirred at 80° C. for 1.5 h, then cooled and poured into water (20 mL). The mixture was extracted with ethyl acetate (30 mL×3). The organic layers were combined, washed with brine (saturated, 50 mL), dried over anhydrous $Na_2SO_4$, filtered and concentrated. The resulting residue was purified by column chromatography ($SiO_2$, gradient elution, 40:1 to 20:1 petroleum ether:EtOAc) to give the title compound. MS (ESI) m/z: 328.1 [M+H+]

Step 4: (5-(2-(2,2-difluoroethoxy)-5-fluoropyridin-4-yl)-3-methylpyrazin-2-yl)methanol Sodium borohydride (0.532 g, 14.06 mmol) was added to a solution of methyl 5-(2-(2,2-difluoroethoxy)-5-fluoropyridin-4-yl)-3-methylpyrazine-2-carboxylate (2.3 g, 7.03 mmol) in MeOH (20 ml). The resulting mixture was stirred at 70° C. for 1h. Then water (20 mL) was poured into the mixture and the mixture was reduced in volume. The resulting solution was extracted with ethyl acetate (30 mL×3). The organic layers were combined, washed with brine (saturated, 50 mL), dried over anhydrous $Na_2SO_4$, filtered and concentrated to give the title compound, which was used in the next step without further purification.

Intermediate 15

1-(5-(5-chloro-2-methoxypyridin-4-yl)-3-methylpyrazin-2-yl)prop-2-en-1-ol

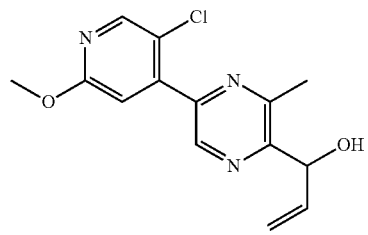 [SMILES: C=CC(O)c1ncc(-c2cc(OC)ncc2Cl)nc1C]

Step 1: 5-(5-chloro-2-methoxypyridin-4-yl)-3-methylpyrazine-2-carbaldehyde

Dess-Martin Periodinane (7.8 g, 18.39 mmol) was added to a stirred, room temperature mixture of (5-(5-chloro-2-methoxypyridin-4-yl)-3-methylpyrazin-2-yl)methanol (3.68 g, 13.85 mmol) in $CH_2Cl_2$ (139 ml). The reaction mixture was stirred at room temperature for 90 min, then 1M aqueous sodium thiosulfate (100 mL) and saturated aqueous $NaHCO_3$ (100 mL) were added. The reaction was stirred for 30 min, then the layers were separated. The aqueous layer was extracted with dichloromethane (50 mL). The organic layers were combined, dried over anhydrous $Na_2SO_4$, filtered and evaporated. The resulting residue was dissolved in $CH_2Cl_2$ and loaded onto a dry ISCO RediSep Gold 220 g silica gel column. A stream of nitrogen was blown through the column to evaporate the $CH_2Cl_2$. The residue was eluted via gradient elution with 0% to 70% EtOAc in hexanes) to give the title compound.

Step 2: 1-(5-(5-chloro-2-methoxypyridin-4-yl)-3-methylpyrazin-2-yl)prop-2-en-1-ol Zinc chloride (7.24 g, 53.1 mmol) was put in a 500 mL flask and placed under high vacuum. The flask was heated with a heat gun for 3 minutes, then cooled to room temperature and backfilled with nitrogen. THF (150 mL) was added under a nitrogen atmosphere with stirring. The resulting zinc chloride solution was cooled to −40° C. and vinylmagnesium bromide (1M in THF, 45.5 ml, 45.5 mmol) was added dropwise with stirring. A solution of 5-(5-chloro-2-methoxypyridin-4-yl)-3-methylpyrazine-2-carbaldehyde (10 g, 37.9 mmol) in THF (379 ml) was cooled to −40° C. The previously formed vinyl zinc mixture was added dropwise to the aldehyde solution. THF (20 mL) was added to the vinylzinc flask and the resulting mixture was added dropwise to the aldehyde solution. The reaction mixture was stirred at −40° C. for 1 h, then sodium citrate tribasic dehydrate (20% aqueous solution, 500 mL) and EtOAc (500 mL) were added and the mixture was stirred. The layers were separated and the aqueous layer was extracted with ethyl acetate. The organic layers were combined, washed with brine, dried over anhydrous $MgSO_4$, filtered and evaporated. The resulting residue was purified via column chromatography on silica gel (ISCO 220 g, gradient elution with 0% to 100% EtOAc in hexanes) to give the title compound.

TABLE 3

Intermediates 16-20 were prepared according to the procedure of Step 1 of Intermediate 15 from the appropriate starting materials

| Intermediate | Structure |
| --- | --- |
| 16 | (structure) |
| 17 | (structure) |
| 18 | (structure) |
| 19 | (structure) |
| 20 | (structure) |

Intermediate 21

1-(5-(2-(2,2-difluoroethoxy)-5-fluoropyridin-4-yl)-3-methylpyrazin-2-yl)prop-2-en-1-ol

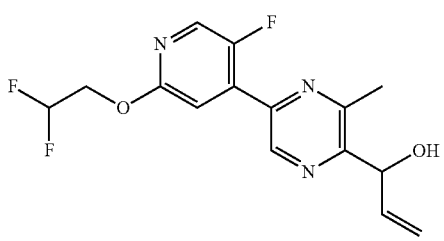 [SMILES: C=CC(O)c1ncc(-c2cc(OCC(F)F)ncc2F)nc1C]

Zinc chloride (3.20 ml, 3.20 mmol) was added to a solution of vinylmagnesium bromide (1M in THF, 9.59 ml, 9.59 mmol) in THF (20 mL). The mixture was stirred at 25° C. for 30 minutes. Then the mixture was then cooled to −78° C. and 5-(2-(2,2-difluoroethoxy)-5-fluoropyridin-4-yl)-3-methylpyrazine-2-carbaldehyde (Intermediate 16, 1.9 g, 6.39 mmol) in THF (10 mL) was added dropwise. The reaction mixture was stirred at −78° C. for 1 h, then poured into water (20 mL) and saturated aqueous NH$_4$Cl (20 mL), and extracted with ethyl acetate (30 mL×3). The combined organic fractions were washed with brine (saturated, 50 mL), dried over anhydrous Na$_2$SO$_4$, filtered and concentrated to afford a residue, which was purified by column chromatography (SiO$_2$, gradient elution, 40:1 to 15:1 petroleum ether:EtOAc) to give the title compound.

Intermediate 22

1-(5-(2-ethoxy-5-fluoropyridin-4-yl)-6-methylpyrazin-2-yl)prop-2-en-1-ol

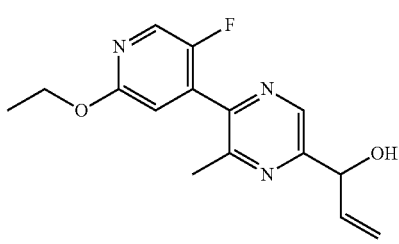 [SMILES: C=CC(O)c1cnc(-c2cc(OCC)ncc2F)c(C)n1]

To a solution of 5-(2-ethoxy-5-fluoropyridin-4-yl)-6-methylpyrazine-2-carbaldehyde (Intermediate 18, 860 mg, 3.29 mmol) in THF (20 mL) was added vinylmagnesium bromide (4.94 mL, 4.94 mmol) dropwise at −78° C. The reaction mixture was stirred for 30 min at −78° C. Then the reaction mixture was quenched by the addition of saturated aqueous NH$_4$Cl and extracted with EtOAc. The combined organic layers were dried over anhydrous MgSO$_4$ and filtered. The filtrate was concentrated in vacuo to give a residue, which was purified by silica gel flash column (24 g, ISCO RediSep Rf, gradient elution, 0% to 100% EtOAc in hexanes) to give the title compound.

TABLE 4

Intermediates 23-26 were prepared according to the procedure of Intermediate 22 from the appropriate starting materials

| Number | Structure |
| --- | --- |
| 23 | (structure) |
| 24 | (structure) |

TABLE 4-continued

Intermediates 23-26 were prepared according to the procedure of Intermediate 22 from the appropriate starting materials

| Number | Structure |
|---|---|
| 25 | ![structure 25] |
| 26 | ![structure 26] |

Examples 1 and 2

(2S,3R)-3-((S)-2-(5-(5-chloro-2-methylpyridin-4-yl)-3-methylpyrazin-2-yl)chroman-7-yl)-3-cyclopropyl-2-methylpropanoic Acid, and (2S,3R)-3-((R)-2-(5-(5-chloro-2-methoxy-pyridin-4-yl)-3-methylpyrazin-2-yl)chroman-7-yl)-3-cyclopropyl-2-methylpropanoic Acid

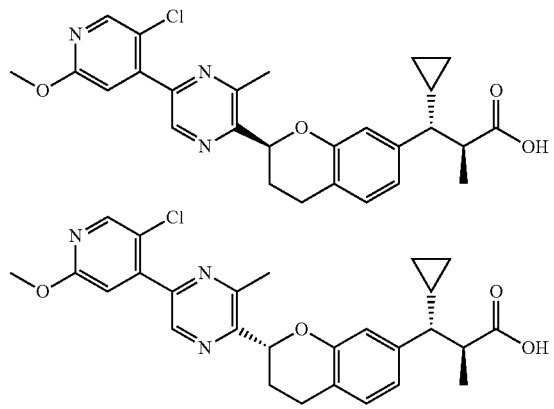

Step 1: (2S,3R)-methyl 3-(4-(3-(5-(5-chloro-2-methoxypyridin-4-yl)-3-methylpyrazin-2-yl)-3-oxopropyl)-3-hydroxyphenyl)-3-cyclopropyl-2-methylpropanoate To a stirred, room temperature, nitrogen-purged mixture of (2S,3R)-methyl 3-cyclopropyl-3-(3-hydroxy-4-iodophenyl)-2-methylpropanoate (1.85 g, 5.14 mmol), 1-(5-(5-chloro-2-methoxypyridin-4-yl)-3-methylpyrazin-2-yl)prop-2-en-1-ol (1.7 g, 5.83 mmol) and chloro[2-(di-tert-butylphosphino)-2',4',6'-triisopropyl-1,1'-biphenyl][2-(2-aminoethyl)phenyl)]palladium(II) (0.529 g, 0.770 mmol) in toluene (51.4 ml) was added N,N-dicyclohexylmethylamine (2.181 ml, 10.27 mmol). The mixture was stirred at 100° C. under a nitrogen atmosphere for 4.5 h, then cooled to room temperature and concentrated. The resulting residue was purified via column chromatography on silica gel (ISCO RediSep Gold 80 g silica gel column, gradient elution with 0% to 100% EtOAc in hexanes) to give the title compound.

Step 2: (2S,3R)-methyl 3-(4-(3-(5-(5-chloro-2-methoxypyridin-4-yl)-3-methylpyrazin-2-yl)-3-hydroxypropyl)-3-hydroxyphenyl)-3-cyclopropyl-2-methylpropanoate Sodium borohydride (0.058 g, 1.527 mmol) was added to a stirred, room temperature mixture of (2S,3R)-methyl 3-(4-(3-(5-(5-chloro-2-methoxypyridin-4-yl)-3-methylpyrazin-2-yl)-3-oxopropyl)-3-hydroxyphenyl)-3-cyclopropyl-2-methylpropanoate (0.8 g, 1.527 mmol) in EtOH (15.27 ml). The reaction mixture was stirred at room temperature for 1 h, then quenched with $NH_4Cl$ (20 mL sat. aq.). The quenched reaction mixture was partitioned between ethyl acetate (30 mL) and water (15 mL). The layers were separated and the aqueous layer was extracted with ethyl acetate. The organic layers were combined, washed with brine, dried over anhydrous $Na_2SO_4$, filtered and evaporated. The resulting residue was purified via column chromatography on silica gel (ISCO RediSep Gold 40 g silica gel column, gradient elution with 0% to 100% EtOAc in hexanes) to give the title compound.

Step 3: (2S,3R)-methyl 3-(2-(5-(5-chloro-2-methoxypyridin-4-yl)-3-methylpyrazin-2-yl)chroman-7-yl)-3-cyclopropyl-2-methylpropanoate Diisopropylazodicarboxylate (185 µl, 0.952 mmol) in 3 mL $CH_2Cl_2$ was added to a stirred, 0° C. mixture of (2S,3R)-methyl 3-(4-(3-(5-(5-chloro-2-methoxypyridin-4-yl)-3-methylpyrazin-2-yl)-3-hydroxypropyl)-3-hydroxyphenyl)-3-cyclopropyl-2-methylpropanoate (334 mg, 0.635 mmol) and $PPh_3$ (250 mg, 0.952 mmol) in $CH_2Cl_2$ (6350 µl). The reaction mixture was stirred at 0° C. for 1 h, then concentrated to a minimal volume and loaded onto a hexanes pre-equilibrated 24 g ISCO RediSep Rf Gold silica gel column and eluted via gradient elution with 0% to 70% EtOAc in hexanes to give the title compound.

Step 4: (2S,3R)-3-(2-(5-(5-chloro-2-methoxypyridin-4-yl)-3-methylpyrazin-2-yl)chroman-7-yl)-3-cyclopropyl-2-methylpropanoic Acid 2M LiOH (aq., 4 ml, 8.00 mmol) was added to a stirred, room temperature mixture of (2S,3R)-methyl 3-(2-(5-(5-chloro-2-methoxypyridin-4-yl)-3-methylpyrazin-2-yl)chroman-7-yl)-3-cyclopropyl-2-methylpropanoate (295 mg, 0.581 mmol) in MeOH (4 ml) and THF (8 ml). The reaction mixture was stirred at 55° C. for 24 h, then cooled to room temperature and partitioned between ethyl acetate (40 mL) and water (40 mL). The pH of the mixture was adjusted to ~pH 1 with HCl (2N aq.). The resulting layers were separated and the aqueous layer was extracted with ethyl acetate. The organic layers were combined, washed with brine, dried over anhydrous $Na_2SO_4$, filtered and evaporated. The resulting residue was purified via column chromatography on silica gel (ISCO RediSep Gold 24 g silica gel column, gradient elution with 0% to 100% EtOAc in hexanes) to give the title compound as a diastereomeric mixture.

Step 5: (2S,3R)-3-((S)-2-(5-(5-chloro-2-methoxy-pyridin-4-yl)-3-methylpyrazin-2-yl)-chroman-7-yl)-3-cyclopropyl-2-methylpropanoic acid, and (2S,3R)-3-((R)-2-(5-(5-chloro-2-methoxy-pyridin-4-yl)-3-methylpyrazin-2-yl)chroman-7-yl)-3-cyclopropyl-2-methyl-propanoic Acid The diastereomeric mixture of (2S,3R)-3-(2-(5-(5-chloro-2-methoxypyridin-4-yl)-3-methylpyrazin-2-yl)chroman-7-yl)-3-cyclopropyl-2-methylpropanoic acid (product of Step 4) was separated via chiral SFC (Chiralcel OJ-H 21 mm×50 mm column, 40° C., 50 mL/min, 120 bar, 25% MeOH co-solvent, 0.5 mL injection, 3.5 mg/mL loading concentration, UV detection at 210 nm) to give the title compounds: Example 1 (peak 1—the earlier eluting peak); and Example 2 (peak 2—the later eluting peak). The fractions from each peaks were separately concentrated and subjected to silica gel chromatography (ISCO RediSep Gold 12 g silica gel column, gradient elution with 0% to 100% EtOAc in hexanes) to give the title compounds: Example 1 and Example 2 as the free acids.

Sodium salt of Example 1

To a solution of Example 1 (9 mg, 0.0182 mmol) in MeCN (0.3 mL) in a 1 dram vial was added aq. NaOH (0.18 mL, 0.1M). The vial was agitated to ensure a uniform solution, then frozen in a dry ice/isopropanol bath. The frozen reaction mixture was lyophilized to afford the sodium salt of Example 1.

Example 1

(m/z M+H+=494.2); $^1$H NMR (400 MHz, Chloroform-d) δ 8.87 (s, 1H), 8.30 (s, 1H), 7.13-7.05 (m, 2H), 6.83-6.73 (m, 2H), 5.40 (dd, J=10.8, 2.1 Hz, 1H), 4.00 (s, 3H), 3.16-2.92 (m, 2H), 2.82 (m, 4H), 2.60-2.44 (m, 1H), 2.39-2.28 (m, 1H), 1.95 (t, J=9.9 Hz, 1H), 1.12 (m, 1H), 1.03 (d, J=6.8 Hz, 3H), 0.64 (dtd, J=11.0, 8.2, 5.1 Hz, 1H), 0.38 (dq, J=8.1, 4.4, 3.8 Hz, 2H), 0.12-0.03 (m, 1H).

Example 2

(m/z M+H+=494.2); $^1$H NMR (500 MHz, Chloroform-d) δ 8.87 (s, 1H), 8.29 (s, 1H), 7.17-7.02 (m, 1H), 6.75 (dd, J=9.8, 2.1 Hz, 1H), 5.40 (dd, J=10.9, 2.1 Hz, 1H), 4.00 (s, 3H), 3.09 (ddd, J=17.6, 12.4, 6.2 Hz, 1H), 2.98 (dd, J=16.6, 3.2 Hz, 1H), 2.91-2.76 (m, 4H), 2.66-2.43 (m, 1H), 2.43-2.16 (m, 1H), 1.95 (t, J=10.0 Hz, 1H), 1.25-1.04 (m, 1H), 1.02 (d, J=6.9 Hz, 3H), 0.64 (q, J=5.9 Hz, 1H), 0.38 (dd, J=6.5, 4.9 Hz, 1H), 0.17-−0.03 (m, 1H)

TABLE 5

The compounds of Examples 3-10 were prepared using a method similar to the procedure of Examples 1 and 2 from the appropriate starting materials

| Example | SFC conditions | Structure | m/z |
| --- | --- | --- | --- |
| 3 | Earlier eluting isomer 0.5 mL in Vol; 120 bar; 50% EtOH; 40 C.; 280 mg in 32 ml; AD-H 21 × 250 mm; 50 g/min | 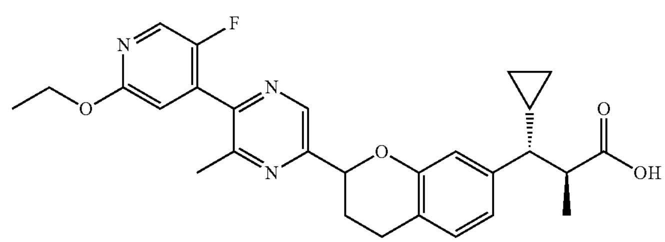 [SMILES: CCOc1cc(-c2ncc(C3CCc4ccc([C@H](C5CC5)[C@H](C)C(=O)O)cc4O3)nc2C)c(F)cn1] | 492.3 |
| 4 | Later eluting isomer 0.5 mL inj. Vol; 120 bar; 50% EtOH; 40 C; 280 mg in 32 ml; AD-H 21 × 250 mm; 50 g/min | 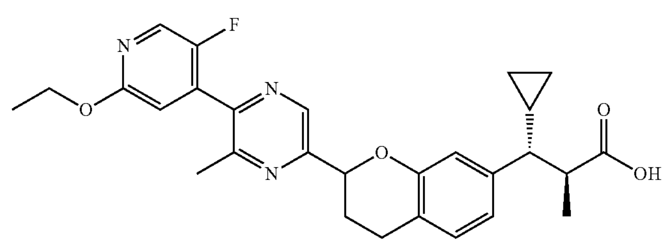 [SMILES: CCOc1cc(-c2ncc(C3CCc4ccc([C@H](C5CC5)[C@H](C)C(=O)O)cc4O3)nc2C)c(F)cn1] | 492.2 |
| 5 | Earlier eluting isomer 0.5 mL inj. Vol; 120 bar; 40% iPrOH; 40 C; 250 mg in 40 ml MeOH; AD-H 21 × 250 mm; 50 g/min | 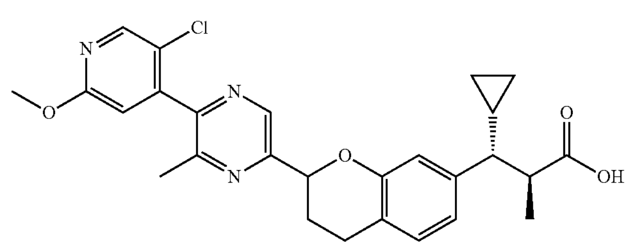 [SMILES: COc1cc(-c2ncc(C3CCc4ccc([C@H](C5CC5)[C@H](C)C(=O)O)cc4O3)nc2C)c(Cl)cn1] | 494.2 |

TABLE 5-continued

The compounds of Examples 3-10 were prepared using a method similar to the procedure of Examples 1 and 2 from the appropriate starting materials

| Example | SFC conditions | Structure | m/z |
|---|---|---|---|
| 6 | Later eluting isomer 0.5 mL in Vol; 120 bar; 40% iPrOH; 40 C; 250 mg in 40 ml MeOH; AD-H 21 × 250 mm; 50 g/min | 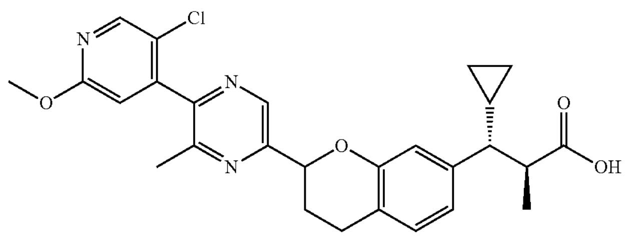 [SMILES: COc1cc(-c2ncc(C3CCc4ccc([C@H](C5CC5)[C@H](C)C(=O)O)cc4O3)nc2C)c(Cl)cn1] | 494.2 |
| 7 | Earlier eluting isomer SFC conditions: Chiralpak AD-3 150 × 4.6 mm I.D., 3 um Mobile phase: A: CO2 B: isopropanol (0.05% DEA) Gradient: from 5% to 40% of B in 5 min and hold 40% for 2.5 min, then 5% of B for 2.5 min Flow rate: 2.5 mL/min Column temp.: 35° C. | 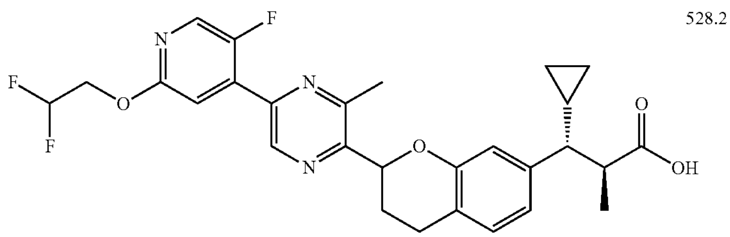 | 528.2 |
| 8 | Later eluting isomer SFC conditions: Chiralpak AD-3 150 × 4.6 mm I.D., 3 um Mobile phase: A: CO2 B: isopropanol (0.05% DEA) Gradient: from 5% to 40% of B in 5 min and hold 40% for 2.5 min, then 5% of B for 2.5 min Flow rate: 2.5 mL/min Column temp.: 35° C. | 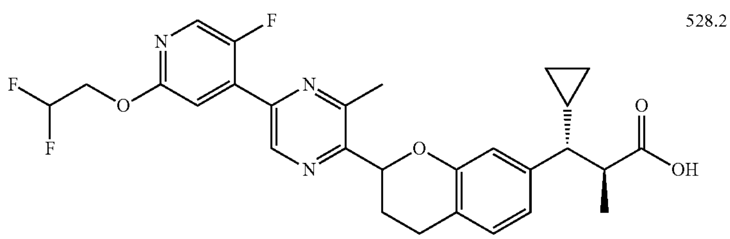 | 528.2 |
| 9 | Later eluting isomer SFC conditions: Chiralpak AS-H (2 cm × 25 cm), isocratic elution: 25% isopropanol in CO2 with 0.1% diethylamine, 100 bar, 60 ml/min, 220 nm detection, injection volume: 0.5 mL (7 mg/ml in 2:1 MeOH:DCM) | 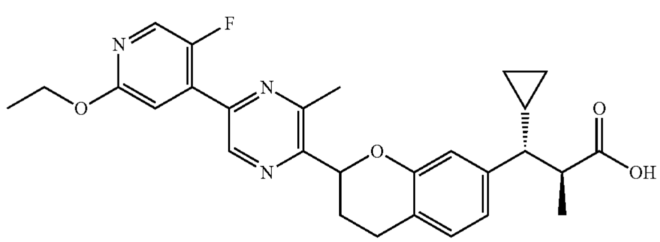 [SMILES: CCOc1cc(-c2cnc(C3CCc4ccc([C@H](C5CC5)[C@H](C)C(=O)O)cc4O3)c(C)n2)c(F)cn1] | 492.3 |
| 10 | Later eluting isomer SFC conditions: Chiralpak AS-H (2 cm × 25 cm), isocratic elution: 40% 1:1 MeOH:MeCN in CO2, 120 bar, 50 ml/min, 40° C., injection volume: 1 mL (100 mg in 20 mL MeOH) | 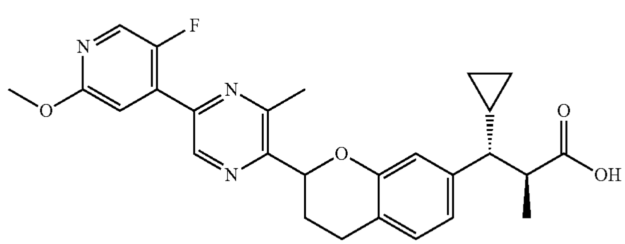 [SMILES: COc1cc(-c2cnc(C3CCc4ccc([C@H](C5CC5)[C@H](C)C(=O)O)cc4O3)c(C)n2)c(F)cn1] | 478.4 |

Examples 11 and 12

(2S,3R)-3-cyclopropyl-3-((R)-2-(5-(2-ethoxy-5-fluoropyridin-4-yl)-6-methylpyrazin-2-yl)-8-fluorochroman-7-yl)-2-methylpropanoic acid, and (2S,3R)-3-cyclopropyl-3-((S)-2-(5-(2-ethoxy-5-fluoropyridin-4-yl)-6-methylpyrazin-2-yl)-8-fluorochroman-7-yl)-2-methylpropanoic Acid

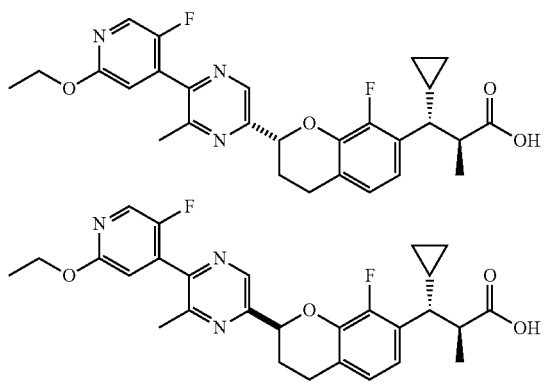

Step 1: methyl (2S,3R)-3-cyclopropyl-3-(4-(3-(5-(2-ethoxy-5-fluoropyridin-4-yl)-6-methyl-pyrazin-2-yl)-3-oxopropyl)-2-fluoro-3-hydroxyphenyl)-2-methylpropanoate A solution of (2S,3R)-methyl 3-cyclopropyl-3-(2-fluoro-3-hydroxy-4-iodophenyl)-2-methylpropanoate (200 mg, 0.529 mmol, prepared in WO 2016022742), 1-(5-(2-ethoxy-5-fluoropyridin-4-yl)-6-methylpyrazin-2-yl)prop-2-en-1-ol (207 mg, 0.714 mmol) and t-butyl x-phos palladacycle Gi (36.3 mg, 0.053 mmol) in toluene (5 mL) was treated with N,N-dicyclohexylmethyl-amine (0.225 mL, 1.058 mmol). The reaction mixture was degassed with nitrogen for 5 min, then heated at 100° C. overnight. The reaction mixture was cooled to RT, evaporated, re-dissolved in DCM and purified by silica gel chromatography (24 g ISCO RediSep, gradient elution 0 to 50% EtOAc in hexanes) to give the title compound.

Step 2: methyl (2S,3R)-3-cyclopropyl-3-(4-(3-(5-(2-ethoxy-5-fluoropyridin-4-yl)-6-methylpyrazin-2-yl)-3-hydroxypropyl)-2-fluoro-3-hydroxyphenyl)-2-methylpropanoate (2S,3R)-methyl 3-cyclopropyl-3-(4-(3-(5-(2-ethoxy-5-fluoropyridin-4-yl)-6-methylpyrazin-2-yl)-3-oxopropyl)-2-fluoro-3-hydroxyphenyl)-2-methylpropanoate (223 mg, 0.413 mmol) was dissolved in EtOH (6 ml), and NaBH$_4$ (31.3 mg, 0.827 mmol) was added at 0° C. The reaction mixture was stirred at 0° C. for 1 h, then quenched with NH$_4$Cl (sat., aq.) and extracted with EtOAc (2×). The organic layers were dried over anhydrous MgSO$_4$, and evaporated. The resulting residue was purified by silica gel chromatography (12 g ISCO RediSep, gradient elution 0 to 100% EtOAc in hexanes) to give the title compound

Step 3: methyl (2S,3R)-3-cyclopropyl-3-(2-(5-(2-ethoxy-5-fluoropyridin-4-yl)-6-methylpyrazin-2-yl)-8-fluorochroman-7-yl)-2-methylpropanoate Triphenylphosphine (145 mg, 0.554 mmol) was added to a solution of (2S,3R)-methyl 3-cyclopropyl-3-(4-(3-(5-(2-ethoxy-5-fluoropyridin-4-yl)-6-methylpyrazin-2-yl)-3-hydroxypropyl)-2-fluoro-3-hydroxyphenyl)-2-methylpropanoate (200 mg, 0.369 mmol) in CH$_2$Cl$_2$ (10 ml). The resulting solution was cooled to 0° C., and a solution of DIAD (0.108 ml, 0.554 mmol) of CH$_2$Cl$_2$ (1 mL) was added dropwise. The reaction mixture was stirred at 0° C. for 1 h, then evaporated. The resulting residue was purified by silica gel chromatography (24 g ISCO RediSep, gradient elution 0 to 40% EtOAc in hexanes) to give the title compound.

Step 4: (2S,3R)-3-cyclopropyl-3-(2-(5-(2-ethoxy-5-fluoropyridin-4-yl)-6-methylpyrazin-2-yl)-8-fluorochroman-7-yl)-2-methylpropanoic Acid A solution of LiOH.H$_2$O (279 mg, 6.65 mmol) in water (2 mL) was added to a stirred solution of (2S,3R)-methyl 3-cyclopropyl-3-(2-(5-(2-ethoxy-5-fluoropyridin-4-yl)-6-methylpyrazin-2-yl)-8-fluorochroman-7-yl)-2-methylpropanoate (174 mg, 0.332 mmol) in MeOH (8 ml) and tetrahydrofuran (4 ml). The reaction mixture was stirred at 55° C. overnight. then acidified with HCl (3.5 mL, 2N) and extracted with EtOAc. The combined organic layers were washed with brine, dried over anhydrous MgSO$_4$ and evaporated. The resulting residue was re-dissolved in DCM and purified by silica gel chromatography (12 g ISCO RediSep, gradient elution 0 to 100% EtOAc in hexanes) to give the title compound as a diastereomeric mixture.

Step 5: (2S,3R)-3-cyclopropyl-3-((R)-2-(5-(2-ethoxy-5-fluoropyridin-4-yl)-6-methylpyrazin-2-yl)-8-fluorochroman-7-yl)-2-methylpropanoic acid, and (2S,3R)-3-cyclopropyl-3-((S)-2-(5-(2-ethoxy-5-fluoropyridin-4-yl)-6-methylpyrazin-2-yl)-8-fluorochroman-7-yl)-2-methylpropanoic Acid The diastereomeric mixture of (2S,3R)-3-cyclopropyl-3-(2-(5-(2-ethoxy-5-fluoropyridin-4-yl)-6-methylpyrazin-2-yl)-8-fluorochroman-7-yl)-2-methylpropanoic acid (the product of Step 4) was separated by chiral SFC (Chiralcel OJ-H, 40° C., 50 mL/min, 120 bar, 30% MeOH co-solvent, 0.6 mL injection, 6 mg/mL loading concentration, UV detection at 210 nm) to give the title compounds as the free acids:

Example 11

(m/z M+H+=510.2) $^1$H NMR (500 MHz, Chloroform-d) δ 8.83 (s, 1H), 8.13 (s, 1H), 6.88 (d, J=7.8 Hz, 1H), 6.83 (d, J=4.7 Hz, 1H), 6.76 (t, J=6.6 Hz, 1H), 5.33 (d, J=8.6 Hz, 1H), 4.39 (q, J=7.0 Hz, 2H), 3.05 (m, 2H), 2.85 (d, J=16.6 Hz, 1H), 2.56 (s, 3H), 2.39 (t, J=9.7 Hz, 1H), 2.31-2.18 (m, 1H), 1.43 (t, J=7.0 Hz, 3H), 1.40-1.14 (m, 2H), 1.08 (s, 3H), 0.66 (s, 1H), 0.44 (br s, 1H), 0.38 (br s, 1H), 0.09 (m, 4H); and

Example 12

(m/z M+H+=510.2) $^1$H NMR (500 MHz, Chloroform-d) δ 8.83 (s, 1H), 8.13 (s, 1H), 6.88 (d, J=8.0 Hz, 1H), 6.83 (d, J=4.7 Hz, 1H), 6.80-6.75 (m, 1H), 5.33 (d, J=10.5 Hz, 1H), 4.39 (q, J=7.0 Hz, 2H), 3.11-2.91 (m, 2H), 2.90-2.80 (m, 1H), 2.61-2.50 (m, 4H), 2.44-2.34 (m, 1H), 2.30-2.19 (m, 1H), 1.43 (t, J=7.1 Hz, 3H), 1.25 (m, 2H), 1.08 (s, 3H), 0.68 (s, 1H), 0.45 (s, 1H), 0.39 (s, 1H), 0.09 (m, 4H).

Sodium Salt of Example 11

To a solution of Example 11 (61 mg, 0.12 mmol) in MeCN (1 mL) and water (1 mL) in a 1 dram vial was added aq. NaOH (0.12 mL, 1M). The vial was agitated to ensure a uniform solution, then frozen in a dry ice/isopropanol bath. The frozen mixture was lyophilized to afford the sodium salt of Example 11.

Sodium Salt of Example 12

To a solution of Example 12 (56 mg, 0.11 mmol) in MCN (1m) and water (1 mL in 1 dram vial was added aq. NaOH (0.11 mL, 1M). The vial was agitated to ensure uniform solution, then frozen in a dry ice/isopropanol bath. The frozen mixture was lyophilized to afford the sodium salt of Example 12.

TABLE 6

The compounds of Examples 13-22 were prepared using a method similar to the procedure of Examples 11 and 12 from the appropriate starting materials

| Example | SFC conditions | Structure | m/z |
|---|---|---|---|
| 13 | Earlier eluting isomer 0.5 mL in Vol; 120 bar; 45% EtOH w/0.1 % diisopropylamine; 35° C.; 280 mg in 32 ml; AD-H 21 × 250 mm; 50 g/min | 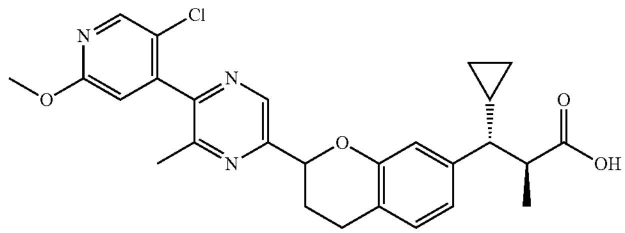 [SMILES: COc1cc(-c2ncc(C3CCc4ccc([C@H](C5CC5)[C@H](C)C(=O)O)cc4O3)nc2C)c(Cl)cn1] | 512.3 |
| 14 | Later eluting isomer | 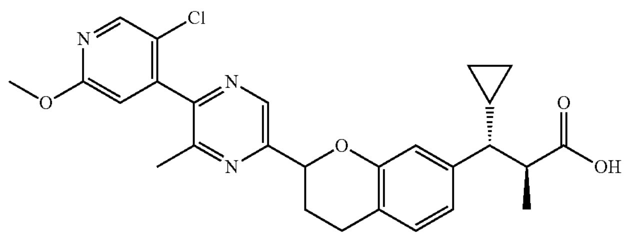 [SMILES: COc1cc(-c2ncc(C3CCc4ccc([C@H](C5CC5)[C@H](C)C(=O)O)cc4O3)nc2C)c(Cl)cn1] | 512.2 |
| 15 | Earlier eluting isomer Chiralpak AD-3 50*4.6 mm I.D., 3 um, Mobile phase: A: CO2 B: ethanol (0.05% DEA), Gradient: hold 5% for 0.2 min, then from 5% to 40% of B in 1.4 min and hold 40% for 1.05 min, then 5% of B for 0.35 min, Flow rate: 4 mL/min | 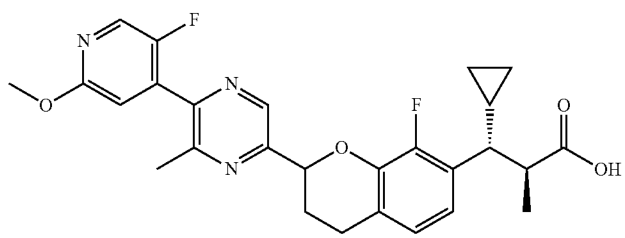 [SMILES: COc1cc(-c2ncc(C3CCc4ccc([C@H](C5CC5)[C@H](C)C(=O)O)c(F)c4O3)nc2C)c(F)cn1] | |
| 16 | Later Eluting Isomer Column: Chiralpak AD-3 50*4.6 mm I.D., 3 um, Mobile phase: A: CO2 B: ethanol (0.05% DEA), Gradient: hold 5% for 0.2 min, then from 5% to 40% of B in 1.4 min and hold 40% for 1.05 min, then 5% of B for 0.35 min, Flow rate: 4 mL/min | 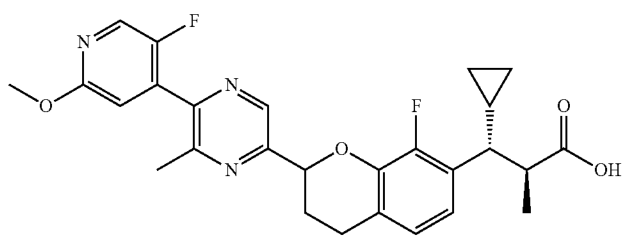 [SMILES: COc1cc(-c2ncc(C3CCc4ccc([C@H](C5CC5)[C@H](C)C(=O)O)c(F)c4O3)nc2C)c(F)cn1] | |
| 17 | Earlier eluting isomer Chiralpak AD-3 100 × 4.6 mm I.D., 3 um, Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min | 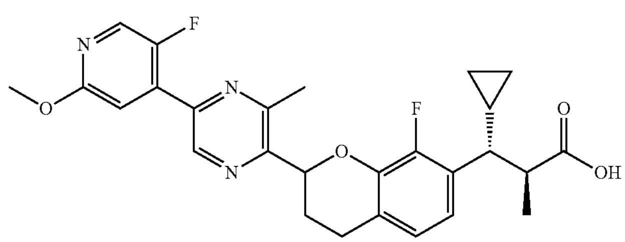 [SMILES: COc1cc(-c2cnc(C3CCc4ccc([C@H](C5CC5)[C@H](C)C(=O)O)c(F)c4O3)c(C)n2)c(F)cn1] | 496.1 |

TABLE 6-continued

The compounds of Examples 13-22 were prepared using a method similar to the procedure of Examples 11 and 12 from the appropriate starting materials

| Example | SFC conditions | Structure | m/z |
|---|---|---|---|
| 18 | Later Eluting Isomer Chiralpak AD-3 100 × 4.6 mm I.D., 3 um, Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min | 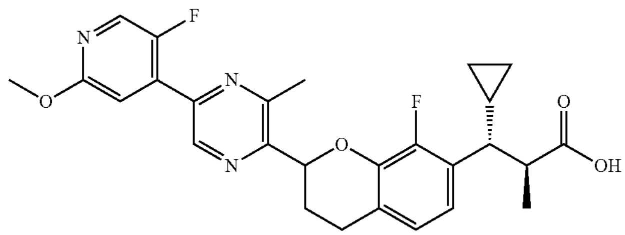 | 496.1 |
| 19 | Earlier eluting isomer 0.8 mL inj. Vol (178 mg/36 ml in 1:1MeOH:MeCN); 120 bar; 40% 1:1 MeOH:MeCN w/0.1 % diisopropylamine; 35° C.; Chiralpak AD-H 21 × 250 mm; 50 g/min | 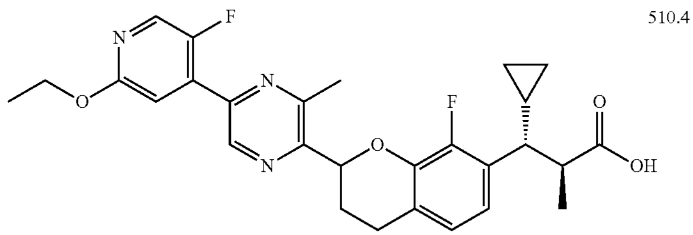 | 510.4 |
| 20 | Later eluting isomer 0.8 mL inj. Vol (178 mg/36 ml in 1:1MeOH:MeCN); 120 bar; 40% 1:1 MeOH:MeCN w/0.1 % diisopropylamine; 35° C.; Chiralpak AD-H 21 × 250 mm; 50 g/min | 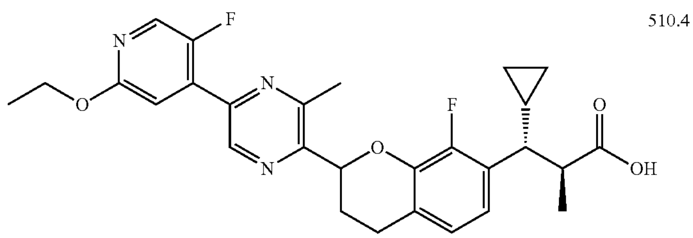 | 510.4 |
| 21 | Earlier eluting isomer Chiralpak AD-3 100 × 4.6 mm I.D., 3 um, Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min | 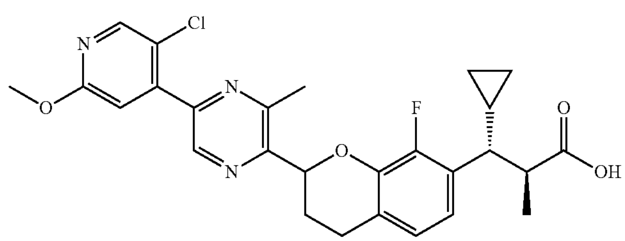 [SMILES: COc1cc(-c2cnc(C3CCc4ccc([C@H](C5CC5)[C@H](C)C(=O)O)c(F)c4O3)c(C)n2)c(F)cn1] | 496.1 |
| 22 | Later eluting isomer Chiralpak AD-3 100 × 4.6 mm I.D., 3 um, Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min | 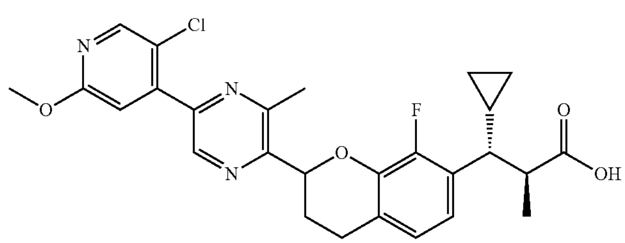 | 496.1 |

Examples 23 and 24

(2S,3R)-3-cyclopropyl-3-((R)-2-(6-ethyl-5-(5-fluoro-2-methoxypyridin-4-yl)pyrazin-2-yl)chroman-7-yl)-2-methylpropanoic acid, and (2S,3R)-3-cyclopropyl-3-((S)-2-(6-ethyl-5-(5-fluoro-2-methoxypyridin-4-yl)pyrazin-2-yl)chroman-7-yl)-2-methylpropanoic Acid

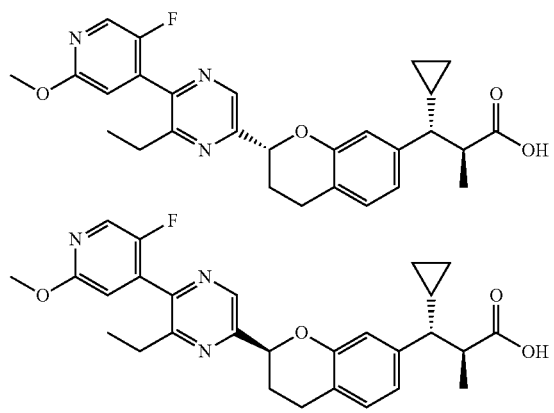

Step 1: methyl (E)-6-(2-(dimethylamino)vinyl)-5-(5-fluoro-2-methoxypyridin-4-yl)pyrazine-2-carboxylate Methyl 5-(5-fluoro-2-methoxypyridin-4-yl)-6-methylpyrazine-2-carboxylate (8 g, 28.9 mmol) was dissolved in DMF (120 ml) and N,N-dimethylformamide dimethyl acetal (120 ml). The reaction was heated at 135° C. for 24 h, then cooled to room temperature and poured into cold water (1000 mL). The resulting slurry was diluted with water and stirred for 1 h, then filtered. The filter cake was washed with water and kept under vacuum pulling air through for 1h. The resulting solid was suspended in Et$_2$O/EtOAc, concentrated, and dried in vacuo to give the title compound.

Step 2: methyl 5-(5-fluoro-2-methoxypyridin-4-yl)-6-formylpyrazine-2-carboxylate Sodium periodate (14.85 g, 69.4 mmol) was added to a stirred, room temperature mixture of (E)-methyl 6-(2-(dimethylamino)vinyl)-5-(5-fluoro-2-methoxypyridin-4-yl)pyrazine-2-carboxylate (7.69 g, 23.14 mmol) in THF (309 ml) and water (154 ml). The reaction mixture was stirred at room temperature for 7h, then poured into EtOAc (600 mL) and sat. aq. NaHCO$_3$ (600 mL) with stirring. The layers were separated and the aqueous layer was extracted with ethyl acetate (200 mL). The organic layers were combined, washed with brine (300 mL), dried over anhydrous MgSO$_4$ overnight, filtered and evaporated. The resulting residue was purified via column chromatography on silica gel (ISCO RediSep Gold 80 g silica gel column, gradient elution with 0% to 100% EtOAc in hexanes) to give the title compound.

Step 3: methyl 6-(1,3-dioxolan-2-yl)-5-(5-fluoro-2-methoxypyridin-4-yl)pyrazine-2-carboxylate Ethylene glycol (1.367 ml, 24.52 mmol) and para-toluenesulfonic acid monohydrate (0.311 g, 1.634 mmol) were added to a stirred, room temperature mixture of methyl 5-(5-fluoro-2-methoxypyridin-4-yl)-6-formylpyrazine-2-carboxylate (4.76 g, 16.34 mmol) in benzene (163 ml). The reaction mixture was stirred at reflux for 18 h, and then cooled to room temperature. The reaction was partitioned between benzene and saturated aqueous sodium bicarbonate and stirred for 3h. The organic layer was separated, washed with brine, dried over anhydrous MgSO$_4$, filtered and evaporated. The resulting residue was purified via column chromatography on silica gel (ISCO RediSep Gold 80 g silica gel column, gradient elution with 0% to 70% EtOAc in hexanes) to give the title compound.

Step 4: (6-(1,3-dioxolan-2-yl)-5-(5-fluoro-2-methoxypyridin-4-yl)pyrazin-2-yl)methanol A solution of DIBAL-H (24 ml, 24.00 mmol, 1 M in THF) was added dropwise over 10 minutes to a stirred, 0° C. mixture of methyl 6-(1,3-dioxolan-2-yl)-5-(5-fluoro-2-methoxypyridin-4-yl)pyrazine-2-carboxylate (4.32 g, 12.88 mmol) in THF (200 ml). The reaction mixture was stirred at 0° C. for 3h, then DIBAL-H (3 mL, 1 M in THF) was added. The reaction was stirred at 0° C. for 2.5 h, and then additional DIBAL-H (5 mL, 1M in THF) was added. The reaction mixture was again stirred at 0° C. for 1.5 h and then DIBAL-H (8 mL, 1 M in THF) was added. Then the reaction was stirred at 0° C. for 1 h, followed by the addition of DIBAL-H (4 mL, 1M in THF) and continued stirring at 0° C. for 0.5 h. Finally, additional DIBAL-H (5 mL, 1M in THF) was added and the reaction mixture was stirred at 0° C. for 0.5h. Then the reaction mixture was poured into a stirred solution of sodium potassium tartrate (30% aqueous). The mixture was diluted with EtOAc (300 mL) and stirred for 10 min. The layers were separated, and the aqueous layer was extracted with ethyl acetate (200 mL). The organic layers were combined, washed with brine (300 mL), dried over anhydrous Na$_2$SO$_4$, filtered and evaporated. The resulting residue was purified via column chromatography on silica gel (ISCO RediSep Gold 80 g silica gel column, gradient elution with 0% to 100% EtOAc in hexanes) to give the title compound.

Step 4: 6-(1,3-dioxolan-2-yl)-5-(5-fluoro-2-methoxypyridin-4-yl)pyrazine-2-carbaldehyde Dess-Martin Periodinane (5.28 g, 12.45 mmol) was added to a stirred, room temperature mixture of (6-(1,3-dioxolan-2-yl)-5-(5-fluoro-2-methoxypyridin-4-yl)pyrazin-2-yl)methanol (2.55 g, 8.30 mmol) in DCM (100 ml). The reaction mixture was stirred at room temperature for 4.5 h, then diluted with DCM (50 mL), quenched with Na$_2$S2O3 (150 mL, 1M aq.) and sat. aq. NaHCO$_3$ (150 mL), and stirred for 1 h. The layers were separated and the aqueous layer was extracted with dichloromethane. The organic layers were combined, washed with brine, dried over anhydrous Na$_2$SO$_4$, filtered and evaporated. The resulting residue was purified via column chromatography on silica gel (ISCO RediSep Gold 80 g silica gel column, gradient elution with 0% to 70% EtOAc in hexanes) to give the title compound.

Step 5: 1-(6-(1,3-dioxolan-2-yl)-5-(5-fluoro-2-methoxypyridin-4-yl)pyrazin-2-yl)prop-2-en-1-ol A solution of 1M vinylmagnesium bromide in THF (10 ml, 10.00 mmol) was added dropwise over 6 min to a stirred, −40° C. mixture of 6-(1,3-dioxolan-2-yl)-5-(5-fluoro-2-methoxypyridin-4-yl)pyrazine-2-carbaldehyde (2.3 g, 7.53 mmol) in THF (94 ml). The reaction mixture was stirred at −40° C. for 2 h, then poured into sodium citrate tribasic dehydrate solution (150 mL 20% aq.) with stirring. Ethyl acetate (100 mL) was added and the mixture was stirred for 2 h. The layers were separated and the aqueous layer was extracted with ethyl acetate (100 mL). The organic layers were combined, washed with brine, dried over anhydrous $Na_2SO_4$, filtered and evaporated. The resulting residue was purified via column chromatography on silica gel (ISCO RediSep Gold 80 g silica gel column, gradient elution with 0% to 100% EtOAc in hexanes) to give the title compound.

Steps 6-8: methyl (2S,3R)-3-(2-(6-(1,3-dioxolan-2-yl)-5-(5-fluoro-2-methoxypyridin-4-yl)pyrazin-2-yl)chroman-7-yl)-3-cyclopropyl-2-methylpropanoate The title compound was prepared using methods similar to Steps 1-3 of Examples 1 and 2, and substituting 1-(5-(5-chloro-2-methoxypyridin-4-yl)-3-methylpyrazin-2-yl)prop-2-en-1-ol with 1-(6-(1,3-dioxolan-2-yl)-5-(5-fluoro-2-methoxypyridin-4-yl)pyrazin-2-yl)prop-2-en-1-ol.

Step 9: (2S,3R)-methyl 3-cyclopropyl-3-(2-(5-(5-fluoro-2-methoxypyridin-4-yl)-6-formylpyrazin-2-yl)chroman-7-yl)-2-methylpropanoate HCl (2M, aq., 4.50 mL, 9 mmol) was added to a stirred, room temperature mixture of (2S,3R)-methyl 3-(2-(6-(1,3-dioxolan-2-yl)-5-(5-fluoro-2-methoxypyridin-4-yl)pyrazin-2-yl)chroman-7-yl)-3-cyclopropyl-2-methylpropanoate (380 mg, 0.691 mmol) in acetone (9 mL). Then acetone (1 mL) was added to the reaction mixture. The reaction was capped with a pressure-release cap and heated in a heating block at 60° C. overnight. Then the reaction mixture was cooled to room temperature and partitioned between ethyl acetate and saturated aqueous sodium bicarbonate. The layers were separated and the aqueous layer was extracted with EtOAc. The organic layers were combined, washed with brine, dried over anhydrous $MgSO_4$, filtered and evaporated. The resulting residue was purified via column chromatography on silica gel (ISCO RediSep Gold 24 g silica gel column, gradient elution with 0% to 100% EtOAc in hexanes) to give the title compound.

Step 10: methyl (2S,3R)-3-cyclopropyl-3-(2-(5-(5-fluoro-2-methoxypyridin-4-yl)-6-vinylpyrazin-2-yl)chroman-7-yl)-2-methylpropanoate Methyltriphenylphosphonium bromide (138 mg, 0.386 mmol) was dissolved in THF (4 ml) and KOt-Bu (0.371 ml, 0.371 mmol, 1M in THF) was added at 0° C. The reaction mixture was stirred at 0° C. for 30 min, then a solution of (2S,3R)-methyl 3-cyclopropyl-3-(2-(5-(5-fluoro-2-methoxypyridin-4-yl)-6-formylpyrazin-2-yl)chroman-7-yl)-2-methylpropanoate (150 mg, 0.297 mmol) in THF (2.00 ml) was added dropwise. The reaction mixture was stirred at 0° C. for 10 min, then warmed to RT for 30 min. Then the reaction mixture was quenched with sat. $NH_4Cl$, and extracted with EtOAc. The organic layers was washed with brine, dried over anhydrous $MgSO_4$, filtered and evaporated. The resulting residue was re-dissolved in DCM, and purified by silica gel column chromatography (12 g ISCO RediSep, 0 to 40% EtOAc in hexanes) to give the title compound.

Step 11: methyl (2S,3R)-3-cyclopropyl-3-(2-(6-ethyl-5-(5-fluoro-2-methoxypyridin-4-yl)pyrazin-2-yl)chroman-7-yl)-2-methylpropanoate (2S,3R)-Methyl 3-cyclopropyl-3-(2-(5-(5-fluoro-2-methoxypyridin-4-yl)-6-vinylpyrazin-2-yl)chroman-7-yl)-2-methylpropanoate (71 mg, 0.141 mmol) was dissolved in EtOAc (3 mL). Then palladium on carbon (15.00 mg) was added and the reaction mixture was hydrogenated under a $H_2$ balloon at RT for 20 min. The reaction mixture was purged with nitrogen, filtered and evaporated. The resulting residue was re-dissolved in DCM and purified by silica gel column chromatography (12 g ISCO RediSep, gradient elution 0 to 50% EtOAc in hexanes) to give the title compound.

Step 12: (2S,3R)-3-cyclopropyl-3-(2-(6-ethyl-5-(5-fluoro-2-methoxypyridin-4-yl)pyrazin-2-yl)chroman-7-yl)-2-methylpropanoic Acid (2S,3R)-Methyl 3-cyclopropyl-3-(2-(6-ethyl-5-(5-fluoro-2-methoxypyridin-4-yl)pyrazin-2-yl)chroman-7-yl)-2-methylpropanoate (63 mg, 0.125 mmol) was dissolved in MeOH (4 ml) and tetrahydrofuran (2 ml) and lithium hydroxide monohydrate (105 mg, 2.492 mmol) in 1 mL of water were added. The reaction mixture was stirred at 55° C. overnight, then acidified with HCl (1.2 mL, 2N, aq.), and extracted with EtOAc. The combined organic layers were washed with brine, dried over anhydrous $MgSO_4$, filtered and evaporated. The resulting residue was re-dissolved in DCM and purified by silica gel column chromatography (12 g ISCO RediSep, gradient elution 0 to 100% EtOAc in hexanes) to give the title compound as a diastereomeric mixture.

Step 13: (2S,3R)-3-cyclopropyl-3-((R)-2-(6-ethyl-5-(5-fluoro-2-methoxypyridin-4-yl)pyrazin-2-yl)chroman-7-yl)-2-methylpropanoic acid, and (2S,3R)-3-cyclopropyl-3-((S)-2-(6-ethyl-5-(5-fluoro-2-methoxypyridin-4-yl)pyrazin-2-yl)chroman-7-yl)-2-methylpropanoic Acid The diastereomeric mixture of (2S,3R)-3-cyclopropyl-3-(2-(6-ethyl-5-(5-fluoro-2-methoxypyridin-4-yl)pyrazin-2-yl)chroman-7-yl)-2-methylpropanoic acid (product of Step 12) was separated via chiral SFC (Chrialpak AD-H, 40° C., 50 mL/min, 120 bar, 40% isopropanol with 0.1% diisopropylamine co-solvent, 0.5 mL injection, 5 mg/mL loading concentration, UV detection at 210 nm) to give the title compounds as the free acids:

Example 23

(m/z M+H+=492.4) $^1$H NMR (500 MHz, Chloroform-d) δ 8.80 (s, 1H), 8.14 (s, 1H), 7.07 (d, J=7.8 Hz, 1H), 6.85-6.81 (m, 2H), 6.76 (dd, J=7.8, 1.4 Hz, 1H), 5.34-5.27 (m, 1H), 3.98 (s, 3H), 3.04 (ddd, J=16.5, 10.6, 5.9 Hz, 1H), 2.92-2.75 (m, 4H), 2.57-2.50 (m, 1H), 2.23 (ddt, J=19.4, 10.5, 5.4 Hz, 1H), 1.98 (t, J=10.0 Hz, 1H), 1.26 (dt, J=7.5 Hz, 3H), 1.21-1.09 (m, 1H), 1.05 (d, J=6.9 Hz, 3H), 0.66 (h, J=7.8, 7.4 Hz, 1H), 0.40 (q, J=7.8, 6.7 Hz, 2H), 0.09 (d, J=5.3 Hz, 2H); and Example 24 (m/z M+H+=492.4).

Sodium Salt of Example 24

To a solution of Example 24 (17 mg, 0.035 mmol) in MeCN (1 mL) and water (1 mL) in a 1 dram vial was added aq. NaOH (0.035 mL, 1M). The vial was agitated to ensure a uniform solution, then frozen in a dry ice/isopropanol bath. The frozen mixture was lyophilized to afford the sodium salt of Example 24. $^1$H NMR (500 MHz, Chloroform-d) δ 8.18 (d, J=0.9 Hz, 1H), 7.03 (d, J=7.7 Hz, 1H), 6.93 (d, J=4.7 Hz, 1H), 6.81 (d, J=1.4 Hz, 1H), 6.76 (dd, J=7.8, 1.5 Hz, 1H), 5.32 (dd, J=9.4, 2.5 Hz, 1H), 3.97 (s, 3H), 3.02 (ddd, J=16.2, 10.1, 5.7 Hz, 1H), 2.79 (q, J=7.3 Hz, 3H), 2.72-2.61 (m, 1H), 2.54-2.47 (m, 1H), 2.22 (dtd, J=15.2, 10.0, 5.4 Hz, 1H), 1.97 (t, J=10.0 Hz, 1H), 1.26 (t, J=7.5 Hz, 3H), 1.09 (ddt, J=13.3, 9.7, 4.8 Hz, 1H), 0.88 (d, J=6.9 Hz, 3H), 0.58 (ddd, J=13.7, 8.9, 5.3 Hz, 1H), 0.45 (dq, J=9.8, 4.9 Hz, 1H), 0.25 (tt, J=9.0, 4.5 Hz, 1H), −0.06 (d, J=4.9 Hz, 1H).

Example 25

(2S,3R)-3-cyclopropyl-3-(2-(5-(2-methoxy-5-methylpyridin-4-yl)-3-methylpyrazin-2-yl)chroman-7-yl)-2-methylpropanoic Acid

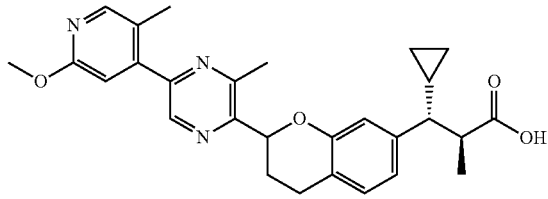 [SMILES: COc1cc(-c2cnc(C3CCc4ccc([C@H](C5CC5)[C@H](C)C(=O)O)cc4O3)c(C)n2)c(C)cn1]

Step 1: (2S,3R)-methyl 3-cyclopropyl-3-(2-(5-(2-methoxy-5-methylpyridin-4-yl)-3-methylpyrazin-2-yl)chroman-7-yl)-2-methylpropanoate To a solution of (2S,3R)-methyl 3-(2-(5-(5-chloro-2-methoxypyridin-4-yl)-3-methylpyrazin-2-yl)chroman-7-yl)-3-cyclopropyl-2-methylpropanoate (60 mg, 0.118 mmol) and trimethylboroxine (22.24 mg, 0.177 mmol) in THF (3 mL) at room temperature was added $2^{nd}$ generation XPhos pre-catalyst (9.29 mg, 0.012 mmol). The reaction mixture was degassed and purged with nitrogen. Then potassium phosphate was added (1N, aq., 0.531 mL, 0.531 mmol), and the reaction mixture was degassed and purged with nitrogen again. The reaction mixture was stirred at 85° C. for 2 h, then cooled to room temperature and diluted with EtOAc. The reaction mixture was washed with water, dried over anhydrous MgSO₄, filtered through a Celite™ plug and concentrated in vacuo. The resulting residue was purified by silica gel column chromatography (12 g ISCO RediSep, gradient elution, 0 to 40% EtOAc in hexanes) to give the title compound.

Step 2: (2S,3R)-3-cyclopropyl-3-(2-(5-(2-methoxy-5-methylpyridin-4-yl)-3-methylpyrazin-2-yl)chroman-7-yl)-2-methylpropanoic Acid (2S,3R)-methyl 3-cyclopropyl-3-(2-(5-(2-methoxy-5-methylpyridin-4-yl)-3-methylpyrazin-2-yl)chroman-7-yl)-2-methylpropanoate (54 mg, 0.111 mmol) was dissolved in MeOH (4 ml) and tetrahydrofuran (2 ml), then a mixture of lithium hydroxide monohydrate (93 mg, 2.215 mmol) in water (1 mL) was added. The reaction mixture was stirred at 55° C. overnight, then acidified with HCl ((2 N, aq, 1.5 mL) and extracted with EtOAc. The combined organic layers were washed with brine, dried over anhydrous MgSO₄, filtered and evaporated to afford a crude residue, which was re-dissolved in DCM and purified by silica gel column chromatography (12 g ISCO RediSep, gradient elution 0 to 100% EtOAc in hexanes) to the title compound.

Step 3: (2S,3R)-3-cyclopropyl-3-(2-(5-(2-methoxy-5-methylpyridin-4-yl)-3-methylpyrazin-2-yl)chroman-7-yl)-2-methylpropanoic Acid The diastereomeric mixture of (2S,3R)-3-cyclopropyl-3-(2-(5-(2-methoxy-5-methylpyridin-4-yl)-3-methylpyrazin-2-yl)chroman-7-yl)-2-methylpropanoic acid (product of Steps 1 and 2) was separated via chiral SFC (Chrialpak AS-H 21×250 mm, 40° C., 50 mL/min, 120 bar, 35% isopropanol with 0.2% diisopropylamine co-solvent, 1 mL injection, 5 mg/mL loading concentration, UV detection at 210 nm) to give the title compound (m/z M+H+=474.3, later eluting isomer). ¹H NMR (500 MHz, Chloroform-d) δ 8.62 (s, 1H), 8.13 (s, 1H), 7.10 (d, J=8.2 Hz, 1H), 6.88 (s, 1H), 6.76 (d, J=5.9 Hz, 2H), 5.39 (dd, J=10.9, 1.8 Hz, 1H), 3.99 (s, 3H), 3.10 (ddd, J=17.6, 12.1, 6.1 Hz, 1H), 2.98 (dd, J=16.6, 3.6 Hz, 1H), 2.89-2.83 (m, 1H), 2.81 (s, 3H), 2.51 (ddq, J=16.9, 10.3, 5.2 Hz, 1H), 2.34 (s, 4H), 1.94 (t, J=10.0 Hz, 1H), 1.32-1.21 (m, 1H), 1.17-1.06 (m, 1H), 1.02 (d, J=6.8 Hz, 3H), 0.63 (dq, J=12.1, 6.9, 5.3 Hz, 1H), 0.38 (q, J=7.0, 5.3 Hz, 2H), 0.11-0.03 (m, 1H).

Example 26

(2S,3R)-3-cyclopropyl-3-(2-(5-(5-cyclopropyl-2-methoxypyridin-4-yl)-3-methylpyrazin-2-yl)chroman-7-yl)-2-methylpropanoic Acid

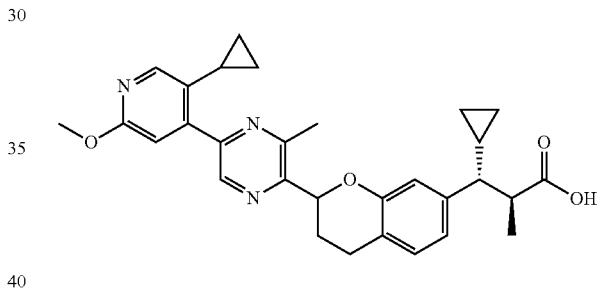

Steps 1 and 2: (2S,3R)-3-cyclopropyl-3-(2-(5-(5-cyclopropyl-2-methoxypyridin-4-yl)-3-methylpyrazin-2-yl)chroman-7-yl)-2-methylpropanoic acid Utilizing a method similar to that outlined in Steps 1 and 2 of Example 25, and substituting cyclopropane boronic acid for trimethylboroxine, the title compound was prepared and isolated as a mixture of diastereomers.

Step 3: (2S,3R)-3-cyclopropyl-3-(2-(5-(5-cyclopropyl-2-methoxypyridin-4-yl)-3-methylpyrazin-2-yl)chroman-7-yl)-2-methylpropanoic Acid The diastereomeric mixture of (2S,3R)-3-cyclopropyl-3-(2-(5-(5-cyclopropyl-2-methoxypyridin-4-yl)-3-methylpyrazin-2-yl)chroman-7-yl)-2-methylpropanoic acid (product of Steps 1 and 2) was separated via chiral SFC (Chrialpak AS-H 21×250 mm, 40° C., 50 mL/min, 120 bar, 35% isopropanol with 0.2% diisopropylamine co-solvent, 1 mL injection, 5 mg/mL loading concentration, UV detection at 210 nm) to afford the title compound (m/z M+H+=500.3, later eluting isomer). ¹H NMR (500 MHz, Chloroform-d) δ 8.80 (s, 1H), 8.05 (s, 1H), 7.10 (d, J=8.2 Hz, 1H), 6.93 (s, 1H), 6.79-6.74 (m, 2H), 5.40 (dd, J=10.9, 1.9 Hz, 1H), 3.98 (s, 3H), 3.10 (ddd, J=17.6, 12.3, 6.3 Hz, 1H), 2.98 (dd, J=16.7, 3.6 Hz, 1H), 2.89-2.81 (m, 4H), 2.52 (ddt, J=17.3, 12.1, 5.6 Hz, 1H), 2.33 (dd, J=13.8, 6.1 Hz, 1H), 2.03-1.90 (m, 2H), 1.33-1.21 (m, 2H), 1.16-1.06 (m, 1H), 1.02 (d, J=6.9 Hz, 3H), 0.94-0.81 (m, 3H), 0.68-0.58 (m, 3H), 0.38 (dt, J=9.3, 4.8 Hz, 2H), 0.11-0.03 (m, 1H).

Example 27

(2S,3R)-3-cyclopropyl-3-{(2R,4S)-2-[5-(5-fluoro-2-methoxypyridin-4-yl)pyrazin-2-yl]-4-methoxy-3,4-dihydro-2H-chromen-7-yl}-2-methylpropanoic Acid

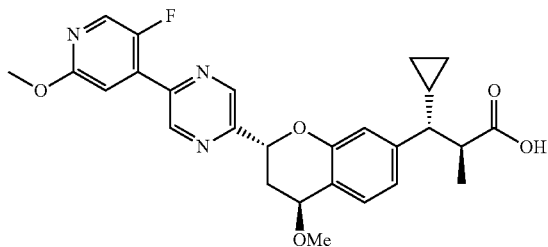 [SMILES: COc1cc(-c2cnc([C@H]3C[C@H](OC)c4ccc([C@H](C5CC5)[C@H](C)C(=O)O)cc4O3)cn2)c(F)cn1]

Step 1: (5-(5-fluoro-2-methoxypyridin-4-yl)pyrazin-2-yl)methanol

The title compound was prepared using a procedure similar to the procedure for Intermediate 3 and substituting (5-chloropyrazin-2-yl)methanol for Intermediate 1 and (5-fluoro-2-methoxypyridin-4-yl)boronic acid for 5-chloro-2-methoxypyridin-4-yl)boronic acid.

Step 2: 5-(5-fluoro-2-methoxypyridin-4-yl)pyrazine-2-carbaldehyde (5-(5-fluoro-2-methoxypyridin-4-yl)pyrazin-2-yl)methanol was converted to the title compound via a procedure similar to that described in Step 1 of Intermediate 15.

Step 3: 1-(5-(5-fluoro-2-methoxypyridin-4-yl)pyrazin-2-yl)prop-2-en-1-ol

The title compound was prepared using a procedure similar to the procedure used to prepare Intermediate 22 starting from 5-(5-fluoro-2-methoxypyridin-4-yl)pyrazine-2-carbaldehyde.

Steps 4-8: (2S,3R)-3-cyclopropyl-3-((S)-2-(5-(5-fluoro-2-methoxypyridin-4-yl)pyrazin-2-yl)chroman-7-yl)-2-methylpropanoic acid and (2S,3R)-3-cyclopropyl-3-((R)-2-(5-(5-fluoro-2-methoxypyridin-4-yl)pyrazin-2-yl)chroman-7-yl)-2-methylpropanoic Acid The title compounds were prepared using procedures similar to Steps 1-4 of Examples 1 and 2 and substituting 1-(5-(5-fluoro-2-methoxypyridin-4-yl)pyrazin-2-yl)prop-2-en-1-ol for 1-(5-(5-chloro-2-methoxypyridin-4-yl)-3-methylpyrazin-2-yl)prop-2-en-1-ol.

Step 9

The diastereomeric mixture of (2S,3R)-3-cyclopropyl-3-((S)-2-(5-(5-fluoro-2-methoxypyridin-4-yl)pyrazin-2-yl)chroman-7-yl)-2-methylpropanoic acid and (2S,3R)-3-cyclopropyl-3-((R)-2-(5-(5-fluoro-2-methoxypyridin-4-yl)pyrazin-2-yl)chroman-7-yl)-2-methylpropanoic acid was separated via chiral supercritical fluid chromatography using the following conditions: Chiralpak AD-H (21 cm×250 cm), isocratic elution: 50% isopropanol in $CO_2$, 120 bar, 50 ml/min, 210 nm detection, injection volume: 0.5 mL (3.8 mg/ml in MeOH) to give the individual diastereomers.

Step 10: (2S,3R)-3-cyclopropyl-3-{(2R,4S)-2-[5-(5-fluoro-2-methoxypyridin-4-yl)pyrazin-2-yl]-4-methoxy-3,4-dihydro-2H-chromen-7-yl}-2-methylpropanoic Acid In a 1 mL vial equipped with a stir bar, (2S,3R)-3-cyclopropyl-3-(2-(5-(5-fluoro-2-methoxypyridin-4-yl)pyrazin-2-yl)chroman-7-yl)-2-methylpropanoic acid (30 mg, 0.065 mmol) was combined with tris(bi-pyridine)ruthenium (II) chloride (2.112 mg, 3.24 µmol) in a glove box. Then MeCN and TFA (1 eq.) were added, followed by methanol (25 µL) and TBPA (1 eq). The vial was capped with a rubber septa sealed cap and the reaction was irradiated using a blue LED light overnight. The reaction mixture was purified using HTP to give the title compound. (m/z M+H+=494.5)$^1$H NMR (600 MHz, Chloroform-d) δ 9.12 (t, J=1.8 Hz, 1H), 9.05 (dd, J=1.5, 0.6 Hz, 1H), 8.17 (dd, J=2.5, 0.5 Hz, 1H), 7.43 (dd, J=5.2, 0.5 Hz, 1H), 7.26 (d, J=7.8 Hz, 1H), 6.85 (d, J=1.6 Hz, 1H), 6.82 (dd, J=7.8, 1.7 Hz, 1H), 5.49 (dd, J=12.2, 2.2 Hz, 1H), 4.36 (t, J=2.8 Hz, 1H), 3.97 (s, 3H), 3.54 (s, 3H), 2.85 (dq, J=9.9, 6.9 Hz, 1H), 2.69 (dt, J=14.2, 2.4 Hz, 1H), 2.10 (ddd, J=14.2, 12.2, 3.2 Hz, 1H), 1.98 (t, J=9.9 Hz, 1H), 1.11 (tdd, J=10.1, 7.9, 5.0 Hz, 1H), 1.02 (d, J=6.9 Hz, 3H), 0.68-0.61 (m, 1H), 0.41-0.33 (om, 2H), 0.07-0.01 (m, 1H).

Biological Assays

Generation of GPR40-Expressing Cells:
Human GPR40 stable cell-lines were generated in HEK cells. The expression plasmids were transfected using lipofectamine (Life Technologies) following manufacturer's instructions. Stable cell-lines were generated following drug selection and single cell cloning.

Inositol Phosphate Turnover (IP1) Assay:
The assay was performed in 384-well format. HEK cells stably expressing human GPR40 were plated at 7500 cells per well in growth medium (DMEM/10% fetal calf serum). Cell plates were then incubated 16 hours at 37 degrees in a 5% $CO_2$ incubator. Measurement of Inositol Phosphate Turnover (IP1) was performed using the CisBio IP-One kit (Part number 62IPAPEB). After the 16 hour incubation, the growth media was removed by centrifugation using the BlueWasher (AusWasher GUI Ver. v1.0.1.8) Protocol #21-"Light Dry" and 10 ul of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% $CO_2$ incubator. 10 ul of detection buffer (also prepared as described in the IP-One kit) was added to each well and the plates were incubated at room temperature for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Data were normalized to % activity using a reference compound and EC50s determined using a standard 4-parameter fit.

The compounds of the present invention, including the compounds in Examples 1-27, have $EC_{50}$ values less than 200 nanomolar (nM) in the Inositol Phophate Turnover Assay 1 described above. Inositol Phophate Turnover (IP1) Assay $EC_{50}$ values for specific compounds are shown in Table I.

TABLE I

Inositol Phophate Turnover (IP1) Assay $EC_{50}$ values

| Example | Human IP1 $EC_{50}$ (nM) |
| --- | --- |
| 1 | 0.6 |
| 2 | 1.3 |
| 3 | 7.8 |
| 4 | 6.9 |
| 5 | 11.2 |
| 6 | 3.3 |
| 7 | 0.9 |
| 8 | 1.0 |
| 9 | 0.7 |
| 11 | 3.5 |
| 12 | 4.3 |
| 13 | 4.1 |
| 14 | 13.8 |
| 15 | 3.0 |
| 16 | 6.6 |
| 17 | 0.3 |
| 18 | 4.2 |
| 19 | 1.1 |
| 20 | 0.4 |
| 21 | 0.3 |
| 22 | 1.6 |
| 23 | 6.5 |
| 24 | 2.3 |
| 25 | 8.1 |
| 26 | 5.4 |
| 27 | 1.7 |

Human Microsomal Binding Assay

Microsomal binding was measured via equilibrium dialysis in a 96 well Teflon block. The dialysis mixture contained 0.3 micromolar of a compound of formula I in 100 mM pH 7.4 phosphate buffer containing 10 mM $MgCl_2$ and 0.25 mg/mL human microsomes. In quadruplicate, a 0.12 mL aliquot of this mixture was loaded into the plate to be dialyzed against 0.12 mL buffer alone. The dialysis plate was shaken for 4 h at 37° C. on an orbital shaker. Aliquots (0.1 mL) were taken from both sides of the dialysis membrane and mixed with 2 volumes of MeCN with 0.1% (v/v) formic acid. The prepared samples were then analyzed by LCMS to determine the fraction unbound.

Human Hepatocyte Clearance Assay

A 2 mM stock solution of a compound of formula I in DMSO (6 L) was diluted with 8.5% DMSO in MeCN (394 μL). A 96-deep well polypropylene plate was incubated at 37 deg C., 5% $CO_2$ atmosphere and 95% humidity for 10 min. Percoll-density-gradient centrifugation was used to enrich in viable hepatocytes if the cells were <70% viable by trypan blue exclusion after thawing. The cell suspension was diluted with Williams' Medium E to $1.00 \times 10^6$ cells/mL. Negative control samples were obtained by boiling $1.0 \times 10^6$ hepatocytes/mL suspension at 100° C. for 15 min to eliminate enzymatic activity. The boiled cells were sonicated for 30 min at 37° C., mixing three times during the sonication. The hepatocytes suspension (198 μL) or boiled hepatocyte suspension in glutamine-enriched Williams' Medium E buffer was transferred to the pre-incubated polypropylene plate. After the addition of cells, the plate was pre-incubated for an additional 10 min in a 37° C. incubator at 5% $CO_2$ and 95% humidity, under constant shaking at 600 rpm. The 30 pM compound stock solution (2 L) was added into an incubation well containing hepatocytes. A homogenous suspension was obtained by pipette mixing for less than or equal to 2 min. The 0-min time point is when the mixing was completed. At the 0-min time point, 20 μL of the incubation suspension was transferred to a well in the quenching plate, followed by pipette mixing. The quenching plate wells consisted of 80 μL acetonitrile with 0.1% v/v formic acid and an internal standard cocktail. Time point samples were taken at 15, 30, 60 and 90 minutes. For the negative control samples, 20 μL of the boiled hepatocyte suspension was transferred from the incubation plate at 0 and 90 min. The quenching plates were vortexed immediately on a plate shaker, then centrifuged at 400 rpm for 20 min. The supernatants were transferred to another 96 well plate with a sample dilution solution and the plates were sealed and subjected to LC/MS/MS analysis to determine the compound concentration, which was used to determine percent remaining relative to time 0. The percent decrease in compound concentration over time was used to determine the human hepatocyte clearance of the compound. Unbound Human Hepatocyte Clearance and Human In Vivo Clearance Unbound human hepatocyte clearance was calculated using data from the Human Microsomal Binding Assay, the Human Hepatocyte Stability Assay, and the non-linear equations outlined in Kilford P J, Gertz M, Houston J B and Galetin A (2008) *Drug Metab Disp* 36:1194-1197.

The unbound human hepatocyte clearance of a compound of formula I was used to predict the human in vivo clearance of that compound as outlined in Ito K and Houston J B (2005) Pharm Res 22:103-112; Obach R S (1996) *Drug Metab Dispos* 24:1047-1049 and Rostami-Hodjegan A and Tucker GT (2007) *Nat Rev Drug Discov* 6:140-148. Using the predicted human in vivo clearance of a compound of formula I and the human GPR40 in vitro potency of that compound, a suitable human dose for the compound was predicted.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

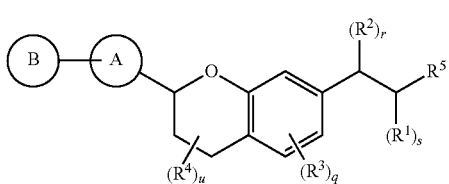

or a pharmaceutically acceptable salt thereof; wherein
A is pyrazine, wherein pyrazine is unsubstituted or substituted with one to two substituents selected from Ra, provided that one of $R^a$ and $R^4$ is not hydrogen;
B is selected from the group consisting of:
(1) aryl, and
(2) heteroaryl,
wherein B is unsubstituted or substituted with one to five substituents selected from $R^b$;
each $R^1$ is independently selected from the group consisting of:
(1) —$C_{1-10}$alkyl,
(2) —$C_{2-10}$alkenyl,
(3) —$C_{2-10}$alkynyl, and
(4) —$C_{3-6}$cycloalkyl,
wherein each alkyl, alkenyl, alkynyl and cycloalkyl is unsubstituted or substituted with 1-4 substituents selected from $C_{1-6}$alkyl, halogen, and —$OC_{1-6}$alkyl;
each $R^2$ is independently selected from the group consisting of:
(1) —$C_{1-10}$alkyl,
(2) —$C_{2-10}$alkenyl,
(3) —$C_{2-10}$alkynyl,
(4) —$C_{3-6}$cycloalkyl,
(5) —$C_{2-5}$cycloheteroalkyl,
(6) aryl, and
(7) heteroaryl,
wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;
$R^3$ is selected from the group consisting of:
(1) hydrogen,
(2) halogen, and
(3) —$C_{1-6}$alkyl;
$R^4$ is selected from the group consisting of:
(1) hydrogen,
(2) $C_{1-6}$alkyl, and
(3) $C_{1-6}$alkyl-O-;
$R^5$ is selected from the group consisting of:
(1) —$CO_2R^6$, and
(2) —C(O)$NR^cR^d$;
R6 is selected from the group consisting of:
(1) hydrogen,
(2) —$C_{1-6}$alkyl,
(3) —$C_{3-6}$cycloalkyl, and
(4) aryl—$C_{1-6}$alkyl,
wherein each alkyl, cycloalkyl and aryl is unsubstituted or substituted with one to three substituents selected from $R^h$;
$R^a$ is selected from the group consisting of:
(1) hydrogen,
(2) —$C_{1-3}$alkyl,
(3) —$CF_3$, and
(4) —$C_{3-6}$cycloalkyl,
wherein each alkyl and cycloalkyl is unsubstituted or substituted with one to three substituents selected from: —$C_{1-3}$alkyl, halogen and —$CF_3$;
$R^b$ is independently selected from the group consisting of:
(1) —$C_{1-10}$alkyl,
(2) —$CF_3$,
(3) halogen,
(4) —CN,
(5) —OH,
(6) —$OC_{1-10}$alkyl,
(7) —$O(CH_2)pOC_{1-10}$alkyl,
(8) —$O(CH_2)pC_{3-6}$cycloalkyl,
(9) —$O(CH_2)pC_{2-5}$cycloheteroalkyl,
(10) —$O(CH_2)pNR^cR^d$,
(11) —$O(CH_2)pO$—$C_{3-6}$cycloalkyl,
(12) —$OCF_3$,
(13) —$OCHF_2$,
(14) —$(CH_2)pC_{3-6}$cycloalkyl, and
(15) —$(CH_2)pC_{2-5}$cycloheteroalkyl,
wherein each CH, $CH_2$, alkyl, alkenyl, cycloalkyl, cycloheteroalkyl, aryl and heteroaryl is unsubstituted or substituted with one to five substituents selected from: —$C_{1-6}$alkyl, halogen, —O—$C_{1-6}$alkyl and —$CF_3$;
$R^c$ and $R^d$ are each independently selected from the group consisting of:
(1) hydrogen,
(2) $C_{1-10}$alkyl,
(3) $C_{3-6}$cycloalkyl,
(4) $C_{3-6}$ cycloalkyl-$C_{1-10}$alkyl-,
(5) $C_{2-5}$cycloheteroalkyl,
(6) aryl-$C_{1-10}$alkyl-, and
(7) heteroaryl-$C_{1-10}$alkyl-,
wherein each alkyl, cycloalkyl, cycloheteroalkyl, aryl and heteroaryl is unsubstituted or substituted with one to three substituents independently selected from $R^f$,
or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$;
each $R^e$ is independently selected from the group consisting of:
(1) hydrogen,
(2) —$C_{1-10}$alkyl,
(3) —$C_{3-6}$ cycloalkyl, and
(4) —$C_{2-5}$cycloheteroalkyl;
each $R^f$ is selected from the group consisting of:
(1) halogen,
(2) $C_{1-10}$alkyl,
(3) —OH,
(4) —O—$C_{1-4}$alkyl,
(5) —S(O)$_m$—$C_{1-4}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, and $C_{1-6}$alkyl;
each $R^g$ is selected from the group consisting of:
(1) hydrogen, and
(2) —$C_{1-10}$alkyl,
wherein each alkyl is unsubstituted or substituted with one to five halogens;
$R^h$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;
each m is independently selected from: 0, 1 and 2;
each p is independently selected from: 0, 1, 2, 3, 4, 5 and 6;
each q is independently selected from 0, 1, 2 and 3;
each u is independently selected from 0, 1 and 2;
each r is independently selected from 0 and 1; and
each s is independently selected from 0 and 1.

2. The compound according to claim 1 wherein A is pyrazine, wherein pyrazine is substituted with one to two substituents selected from $R^a$; or a pharmaceutically acceptable salt thereof.

3. The compound according to claim 1 wherein A is pyrazine, wherein pyrazine is substituted with one substituent selected from $R^a$; or a pharmaceutically acceptable salt thereof.

4. The compound according to claim 1 wherein B is heteroaryl, wherein heteroaryl is unsubstituted or substituted with one to five substituents selected from $R^b$; or a pharmaceutically acceptable salt thereof.

5. The compound according to claim 1 wherein B is pyridine, wherein pyridine is unsubstituted or substituted with one to five substituents selected from $R^b$; or a pharmaceutically acceptable salt thereof.

6. The compound according to claim 1 wherein $R^1$ is —$C_{1-10}$alkyl, wherein alkyl is unsubstituted or substituted with 1-4 substituents selected from $C_{1-6}$alkyl, halogen, and —$OC_{1-6}$alkyl; or a pharmaceutically acceptable salt thereof.

7. The compound according to claim 1 wherein $R^1$ is —$C_{1-3}$alkyl; or a pharmaceutically acceptable salt thereof.

8. The compound according to claim 1 wherein $R^2$ is independently selected from the group consisting of: —$C_{3-6}$ cycloalkyl, wherein cycloalkyl is unsubstituted or substituted with 1-4 substituents selected from $C_{1-6}$alkyl, halogen, and —$OC_{1-6}$alkyl; or a pharmaceutically acceptable salt thereof.

9. The compound according to claim 1 wherein $R^2$ is cyclopropyl, wherein cycloalkyl is unsubstituted or substituted with 1-4 substituents selected from $C_{1-6}$alkyl, halogen, and —$OC_{1-6}$alkyl; or a pharmaceutically acceptable salt thereof.

10. The compound according to claim 1 wherein $R^3$ is selected from the group consisting of: hydrogen and halogen; or a pharmaceutically acceptable salt thereof.

11. The compound according to claim 1 wherein $R^3$ is halogen; or a pharmaceutically acceptable salt thereof.

12. The compound according to claim 1 wherein $R^4$ is hydrogen or $C_{1-6}$alkylO—; or a pharmaceutically acceptable salt thereof.

13. The compound according to claim 1 wherein $R^5$ is —$CO_2R^6$; and $R^6$ is selected from the group consisting of: hydrogen and —$C_{1-6}$alkyl, wherein each alkyl is unsubstituted or substituted with one to three substituents selected from $R^h$; or a pharmaceutically acceptable salt thereof.

14. The compound according to claim 13 wherein $R^5$ is —$CO_2R^6$; and $R^6$ is hydrogen; or a pharmaceutically acceptable salt thereof.

15. The compound according to claim 1 of structural Formula Ik:

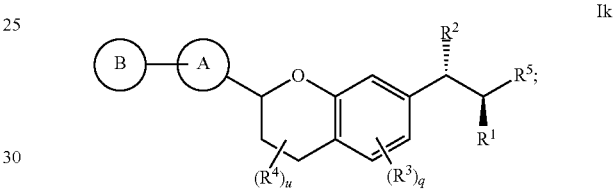

wherein
A is pyrazine, wherein pyrazine is unsubstituted or substituted with one to two substituents selected from $R^a$;
B is heteroaryl, wherein heteroaryl is unsubstituted or substituted with one to five substituents selected from $R^b$;
$R^1$ is —$C_{1-10}$alkyl, wherein alkyl is unsubstituted or substituted with 1-4 substituents selected from $C_{1-6}$alkyl, halogen, and —$OC_{1-6}$alkyl;
$R^2$ is independently selected from the group consisting of: —$C_{3-6}$cycloalkyl, wherein cycloalkyl is unsubstituted or substituted with 1-4 substituents selected from $C_{1-6}$alkyl, halogen, and —$OC_{1-6}$alkyl;
$R^3$ is selected from the group consisting of: hydrogen and halogen;
$R^4$ is hydrogen or $C_{1-6}$alkylO—; or a pharmaceutically acceptable salt thereof
$R^5$ is —$CO_2R^6$;
$R^6$ is selected from the group consisting of: hydrogen and —$C_{1-6}$alkyl, wherein each alkyl is unsubstituted or substituted with one to three substituents selected from $R^h$; and
or a pharmaceutically acceptable salt thereof.

16. The compound according to claim 1 of structural Formula Ik:

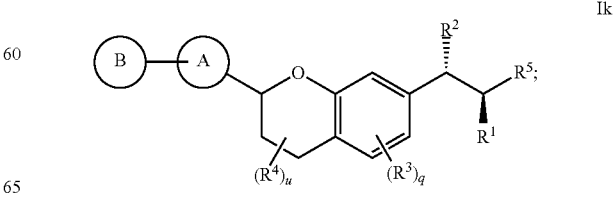

wherein

A is pyrazine, wherein pyrazine is unsubstituted or substituted with one substituent selected from $R^a$;

B is pyridine, wherein pyridine is unsubstituted or substituted with one to five substituents selected from $R^b$;

$R^1$ is —$C_{1-3}$alkyl;

$R^2$ is cyclopropyl, unsubstituted or substituted with 1-4 substituents selected from $C_{1-6}$alkyl, halogen, and —$OC_{1-6}$alkyl;

$R^3$ is halogen;

$R^4$ is hydrogen or $C_{1-6}$alkyl-O—;

$R^5$ is —$CO_2R^6$;

$R^6$ is hydrogen; and or a pharmaceutically acceptable salt thereof.

17. The compound according to claim 1 selected from:

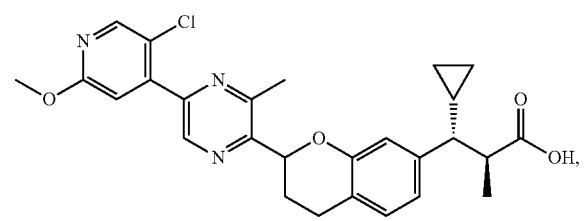

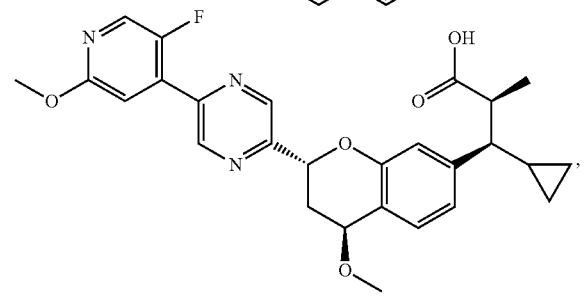

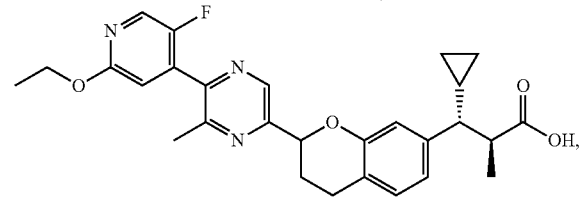

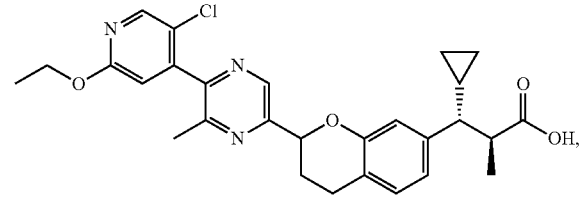

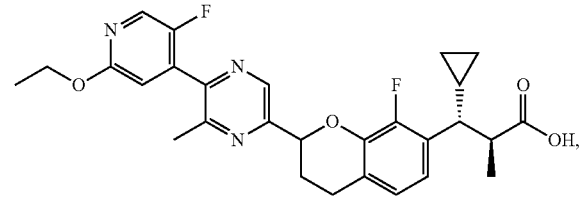

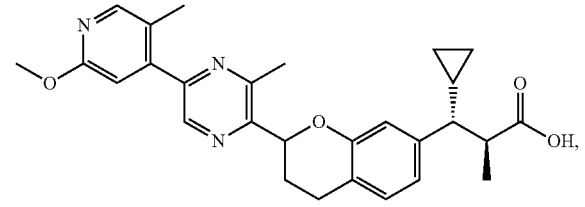

-continued

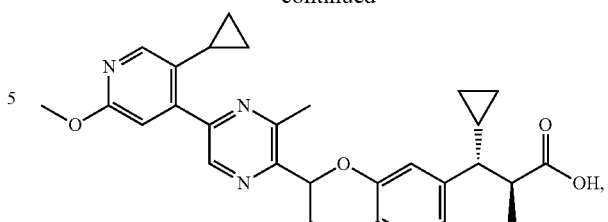

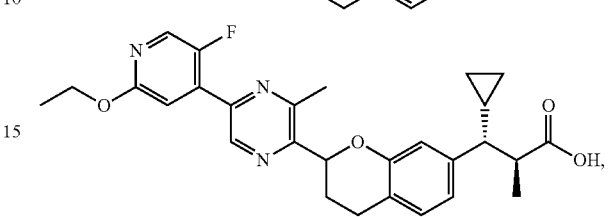

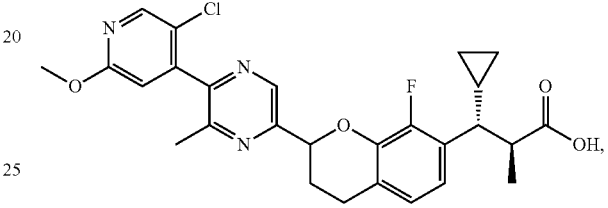

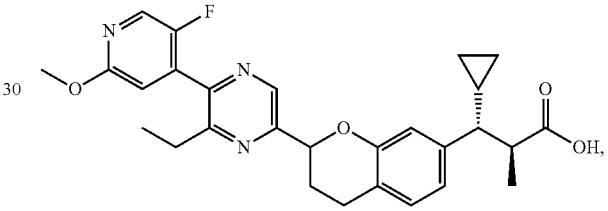

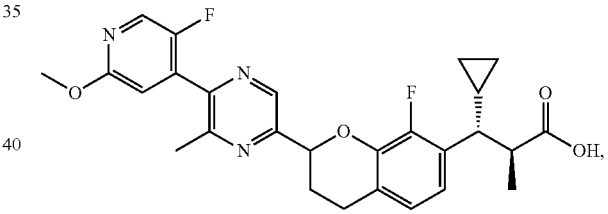

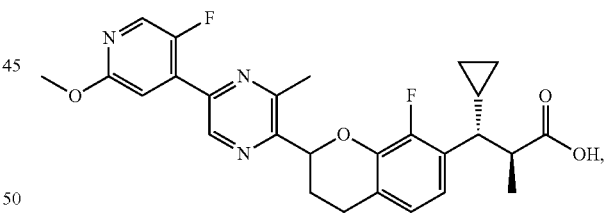

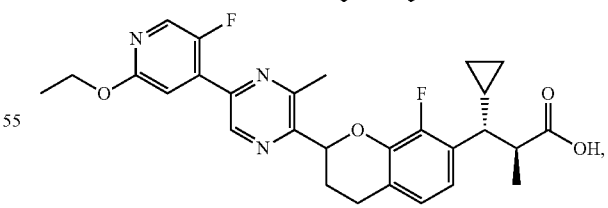

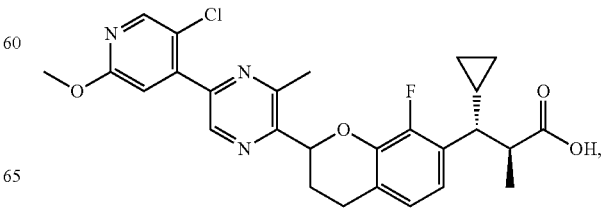

-continued

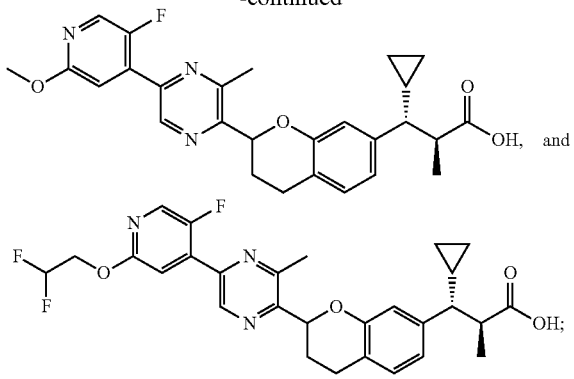

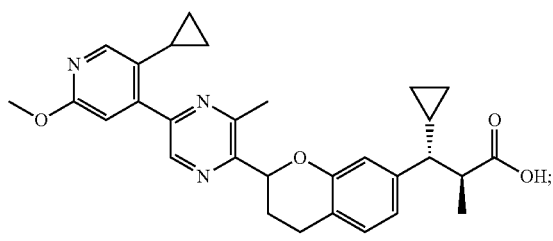 [SMILES: COc1cc(-c2cnc(C3CCc4ccc([C@H](C5CC5)[C@H](C)C(=O)O)cc4O3)c(C)n2)c(C2CC2)cn1]

or a pharmaceutically acceptable salt thereof.

18. The compound according to claim 1 which is:

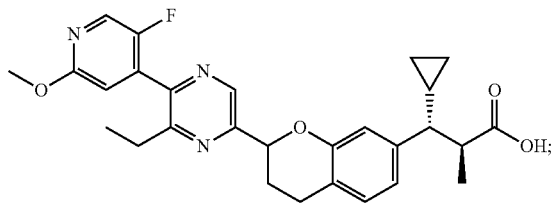 [SMILES: CCc1nc(C2CCc3ccc([C@H](C4CC4)[C@H](C)C(=O)O)cc3O2)cnc1-c1cc(OC)ncc1F]

or a pharmaceutically acceptable salt thereof.

19. The compound according to claim 1 which is:

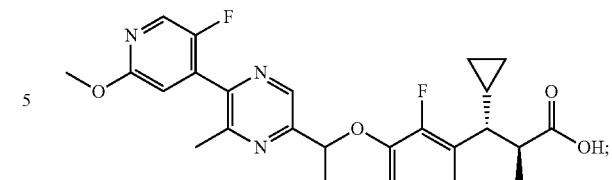

or a pharmaceutically acceptable salt thereof.

20. The compound according to claim 1 which is:

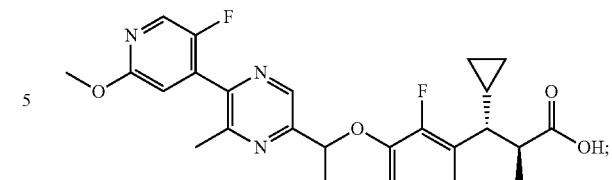

or a pharmaceutically acceptable salt thereof.

21. The compound according to claim 1 which is:

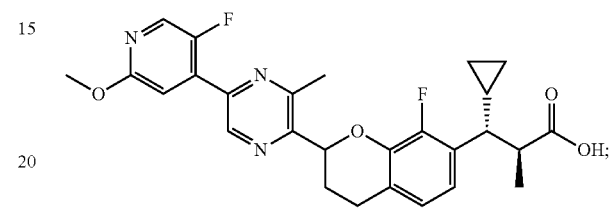

or a pharmaceutically acceptable salt thereof.

22. The compound according to claim 1 which is:

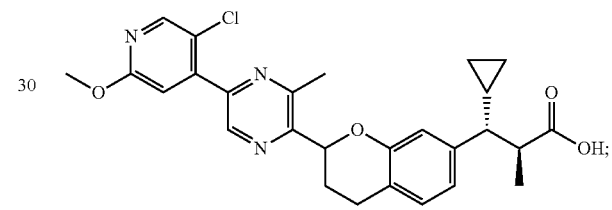

or a pharmaceutically acceptable salt thereof.

23. A pharmaceutical composition comprising a compound of claim 1, or a pharmaceutically acceptable salt thereof, and a pharmaceutically acceptable carrier.

24. A method of treating type 2 diabetes mellitus in a patient in need of treatment comprising the administration to the patient of a therapeutically effective amount of a compound of claim 1, or a pharmaceutically acceptable salt thereof.

* * * * *